(12) United States Patent
Miles et al.

(10) Patent No.: US 6,579,674 B2
(45) Date of Patent: Jun. 17, 2003

(54) METHOD FOR SELECTIVE INACTIVATION OF VIRAL REPLICATION

(75) Inventors: Vincent J. Miles, Chestnut Hill, MA (US); Michael B. Mathews, Montclair, NJ (US); Michael G. Katze, Seattle, WA (US); Julia C. Watson, San Jose, CA (US); Gary Witherell, Orinda, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 10/112,547

(22) Filed: Mar. 28, 2002

(65) Prior Publication Data

US 2002/0160977 A1 Oct. 31, 2002

Related U.S. Application Data

(63) Continuation of application No. 09/724,380, filed on Nov. 28, 2000, which is a continuation of application No. 08/925,156, filed on Sep. 8, 1997, now Pat. No. 6,156,496, which is a division of application No. 08/221,816, filed on Apr. 1, 1994, now Pat. No. 5,738,985, which is a continuation-in-part of application No. 08/042,024, filed on Apr. 2, 1993, now abandoned.

(51) Int. Cl.$^7$ .............................. C12Q 1/68; C12Q 1/70
(52) U.S. Cl. ................................ 435/5; 435/6; 435/7.1; 435/7.2; 435/7.21; 435/7.5; 435/7.92
(58) Field of Search ......................... 435/5, 6, 7.1, 7.2, 435/7.21, 7.5, 7.92

(56) References Cited

U.S. PATENT DOCUMENTS

| 5,248,670 A | 9/1993 | Draper et al. |
| 5,585,479 A | 12/1996 | Hoke et al. |
| 5,622,861 A | 4/1997 | Kaplan et al. |
| 5,738,985 A | 4/1998 | Miles et al. |
| 6,174,868 B1 | 1/2001 | Anderson et al. |
| 6,284,458 B1 | 9/2001 | Anderson et al. |

FOREIGN PATENT DOCUMENTS

| EP | 0 662 157 | 12/1995 |
| WO | WO 83/01451 | 4/1983 |
| WO | WO 92/14422 | 11/1990 |
| WO | WO 92/03456 | 3/1992 |
| WO | WO 93/03143 | 2/1993 |
| WO | WO 99/29350 | 6/1999 |
| WO | WO 00/06590 | 2/2000 |

OTHER PUBLICATIONS

Coward et al., J. Virol., 1992, vol. 66, No. 1, pp. 6312–6315.*
Agris et al., Biochem. 25:6268–6275 (1986).
Babies et al., Mol. Cell. Biol. 5:2552–2558 (1985).
Bae et al., Virology 170:282–287 (1989).
Baroudy et al., Proc. Natl. Acad. Sci. USA 82:2143–2147 (1985).
Beattie et al., Virology 183:419–422 (1991).
Beck et al., Nucleic Acids Res. 11:7873–7885 (1983).
Biegalke & Geballe Virology 177:657–667 (1990).
Black et al., Virology 67:791–800 (1993).
Boothroyd et al., Nature 290:800–802 (1981).
Boothroyd et al., Gene 17:156–161 (1982).
Borman et al.,J. Gen. Virol. 74:1775 (1993).
Borman and Jackson, Virology 188:685 (1992).
Borovjagin et al., "A Factor that Specifically Binds to the 5'–Untranslated Region of Encephalomyocarditis Virus RNA," FEBS Lett. 261:237–240 (1990).
Borovjagin et al., "RNA–Protein Interactions With the Internal ranslation Initiation Region of the Encephalomycarditis Virus RNA," Nucl. Acids Res., 19:4999–5005 (1991).
Bouloy et al., Proc. Natl. Acad. Sci. USA 75:4886–4890 (1978).
Branch, A.D., A good antisence molecule is hard to find, TIBS 23 Feb. 1998, pp. 45–50.
Brown et al., J. VIrol. 65:5828–5838 (1991).
Brown–Driver, V. et al., "Inhibition of translation of hepatitis C virus RNA by 2–modified antisense olgonucleotides." Antisense Nucleic Acid Drug Dev. 1999 Apr;9(2):145–54.
Callahan P et al., Proc. Natl. Acad. Sci. USA 82:732–736 (1985).
Campbell et al., J. Mol. Biol. 180:1–19 (1984).
Carroll & Clarke, Nucleic Acids Res. 12:2461 (1984).
Centrella and Lucas–Lenard, J. Virology 41:781–791 (1982). Centrella and Lucas–Lenard, J. Virology 41:781–791 (1982).
Chang et al., J. Gen. Virol. 70:3269–3280 (1989).
Change et al., Proc. Natl. Acad. Sci. USA 87:5158–5162 (1990). Chang et al., Proc. Natl. Acad. Sci. USA 87:5158–5162 (1990).
Chien et al., Proc. Natl. Avad. Sci. USA 88:9578–9582 (1991).
Choo et al., Proc. Natl. Acad. Sci. USA 88:2451–2455 (1991).
Christianson et al., Genetics 110:119–122 (1992).
Clarke et al., Eur. J. Biochem. 193:635–641 (1990).
Clarke et al., Nucl. Acids. Res. 19:243–248 (1991).
Cohen et al., J. Virol. 61:50–59 (1987).
Cohen et al., Proc. Natl. Acad. Sci. USA 84:2497–2501 (1987).

(List continued on next page.)

*Primary Examiner*—David Guzo
(74) *Attorney, Agent, or Firm*—James J. Diehl

(57) ABSTRACT

Method for screening for an antiviral agent, by determining whether a potential agent interacts with a virus or cellular component which allows or prevents preferential translation of a virus RNA compared to a host RNA under virus infection conditions; and determining whether any interaction of the agent with the component reduces the level of translation of an RNA of the virus.

19 Claims, 10 Drawing Sheets

OTHER PUBLICATIONS

Coward et al., "Yeast Cells are Incapable of Translating RNAs Containing the Poliovirus 5' Untranslated Region Evidence for a Translational Inhibitor," J. Virol. 1992 66(1):286–295.
Cullen, Cell 46:973 (1986).
Del Angel et al., Proc. Natl. Acad. Sci USA 86:8299–8303 (1989).
Deuchler et al., Proc. Natl. Acad. Sci. USA 84:2605–2609(1987).
Dinman and Wickner, "Ribosomal Frameshifting Efficiency and gag/gag–pol Ratio Are Critical for Yeast M.sup.1 Double Stranded RNA Virus Propagation," J. Virol. 66:3699 (1992).
Dolph et al., J. Virology 62:2059–2066 (1988).
Drug and Market Development, vol. 3. No. 9, pp. 174–180 (Feb. 15, 1993).
Duke et al., "Sequence and Structural Elements That Contribute to Efficient Encephalomyocarditis Virus RNA Translation," Journal of Virology 66:1602–1609 (1992).
Earle et al., J. Gen. Virol. 69:253–263 (1988).
Edery et al., Cell 56:303–312 (1989).
Etchison et al., J. Biol. Chem. 257:14806–14810 (1982).
Fields and Song, Nature, 340:245–246 (1989).
Fiers et al., J. Supramol Struct Cell Biochem 5:357 (1981).
Forss et al., Nucleic Acids Res. 12:6587 (1984).
Gambari et al., Int'l J. Pham. 72:251–258 (1991).
Galderisi et al., Expert Opinion on Emerging Drugs 6(1):69–79 (2001) ABSTRACT.
Galibert et al., Nature 281:646–650 (1979).
Garfinkel Katze, J. Biol Chem. 267:9383–9390 (1992).
Geary RS, Yu RZ, Levin AA, Pharmacokinetic of phosphorothioate antisense oligodeoxynucleotides, Curr Opin Investig Drugs. 2001 Apr;2(4):562–73 (ABSTRACT).
Geballe and Mocarski, J. Virology 62:3334–3340 (1988).
Grinell and Wagner, J. Virology 48:88–101 (1983).
Gunnery et al., "Tat–Respponsive Region RNA of Human Immunodeficiency Virus 1 Can Prevent Activation of the Double–Stranded–RNA–Activated Protein Kinase," Proc. Natl. Acad. Sci. USA 87:8687–8691 (1990).
Gura, Science, vol. 270, pp. 575–577, Oct. 27, 1995.
Gutierrez et al., "Transient Inhibition of Foot–and–Mouth Disease Virus Infection of BHK–21 cells by Antisense Oligonucleotides Directed Against the Second Functional Initiator AUG," Antiviral Research 22:1–13 (1993).
Halbert et al., J. Virology 86:250–257 (1985).
Hambidge SJ, and Sarnow P. "Terminal 7–methyl–guanosine cap structure on the normally uncapped 5'noncoding region of poliovirus mRNA inhibits its translation in mammalian cells." J Virol. 1991 Nov;65(11):6312–5.
Han et al., Proc. Natl. Acad. Sci. USA 88:1711–1715 (1991).
Hanecak, R. et al., J. Virol. 70(8):5203–12 (Aug 1996).
Herman, "Alternatives for the Initiation of Translation, " TIBS 14:219–222 (1989).
Hershey, "Translational Control in Mammalian Cells," Ann. Rev. Biochem. 60:717–755 (1991).
Hershey, "Introduction to Translational Initiation Factors and Their Reulation by Phosphorylation," Seminars in Virology 4:201–207 (1993).
Huang and Schneider, Cell 65:271–280 (1991).
Hughes et al., J. Gen. Virol. 69:49–58 (1988).
Hughes et al., J. Gen. Virol. 67:2093–2102 (1986).
Hughes et al., J. Gen. Virol. 70:2943–2952 (1989).
Iizuka et al., Virology 156:64.
Imani and Jacobs, Proc. Natl. Acad. Sci. USA 85:7887–7891 (1988).
Inchauspe et al., Proc. Natl. Acad. Sci. USA 88:10293 (1991).
Inglis, Mol. Cell. Biol. 2:1644–1648 (1982).
Jacks et al., "Characterization of Ribosomal Frameshifting in HIV –1 gag–pol expression," Nature 331–280 (1988).
Jackson, "Initation Without an End," Nature 353:14–15 (1991).
Jackson et al., "The Novel Mechanism of Initiation of Picornavirus RNA Translation," Trends Biochem. Sci. 15:477–482 (1990).
Jang et al., Enzyme 44:292–309 (1990).
Jang and Wimmer, Genes Dev. 4:1560–1572 (1990).
Jang et al., J. Virol. 63:1651 (1989).
Jang SK, et al., "A segment of the 5' nontranslated region of encephalomyocarditis virus RNA directs internal entry of ribosomes during in vitro translation," J. Virol 1988 Aug:62(8):2636–43.
Jean–Jean et al., J. Virology 63:5451–5454 (1989).
Jenkins, J. Gen. Virol 68:1835–1848 (1987).
Kato et al., Proc. Natl. Acad. Sci. USA 87:9524–9528 (1990).
Katze, J. Interferon Res. 12:241–248 (1992).
Katze, "Games Viruses Play: a Stretegic Intiative Against the Interfero–Induced dsRNA Activisted 68,000 M.sub.r Protein Kinase," Seminars in Virology 4:259–268 (1993).
Katze et al., J. Virology 62:3710–3717 (1988).
Kozak, "The Scanning Model for Translation: An Update," J. Cell. Biol. 108:229–241 (1989).
Kozak, "A Consideration of Alternative Models for the Intitiation of Tranlsation in Eukaryotes," Crit. Rev. Biochem. Mol. Biol. 27:385–402 (1992).
Kuhn et al., J. Virol. 64:4625 (1990).
Kwong et al., J. Virology 62:912–921 (1988).
La Monica et al., J. Virology 57:515 (1986).
Le and Zuker, J. Mol. Biol. 216–729–741 (1990).
Lee et al., Proc. Natl. Acad. Sci. USA 87:6208–6212 (1990).
Lima et al., J. Biol. Chem. 272(1):626–638 (1997)Lima et al., J. Biol. Chem. 272(1):626–638 (1997).
Lindberg et al., Virology 156:50 (1987).
Linemeyer et al., J. Virol. 54:252 (1985).
Luz and Beck, J. Virol 65:6486–6494 (1991).
Ma and Mathews, "Comparative Analysis of the Structure and Function of Adenovirus Asociated RNAs," J. Virol. 67:6605–6617 (1993).
Macejak and Sarnow. "Internal Initiation of Translation Mediated by the 5' Leader of a Cellular mRNA," 353–90–94 (1991).
Mathews, "Viral Evasion of Cellular Defense Mechanism: Regulation of the Protein Kinase DAI by RNA Effectors," Seminars in Virology 4:247–257 (1993).
Mathews and Shenk, "Adenovirus Virus–Associated RNA and Translation Control," J. Virology 65:5657–5662 (1991).
Meerovitch and Soneberg, Seminars Virol. 4:217 (1993).
Meerovitch et al., J. Virol. 67:3798 (1993).
Meerovitch et al., "A Cellular Protein That Binds to the 5'–Noncoding Region of Poliovirus RNA: Implications for Internal Translation Initiation," Gene Dev. 3:1026–1034 (1989).
Mellits & Mathews, "Effects of Mutations in Stem and Loop Regions on the Structure and Function of Adenovirus VA RNA.sub.1," EMBO J. 7:2849–2859 (1988).

Mellits, et al., "Role of the Apical Stem in Maintaining the Structure and Function of Adenovirus Virus–Associated RNA," J. Virol. 66:2369–2377 (1992).

Miller and Hinnebusch, Genes Dev. 3:1217 (1989).

Miroshnichenko, et al., "Inhibition of Adenovirus 5 Replication in COS–1 Cells by Antisense RNAs Against the Viral E1A Region," Gene 84:83–89 (1989).

Mizutani et al., J. Virol, vol. 56, No. 2, p. 628–632, Nov. 1985.

Molla et al., "Cardioviral Internal Ribosomal Entry Site is Functional ikn a Genetically Engineered Dicistronic Poliovirus," Nature 356:255–257 (1992).

Moreland et al., J. Virol. 65:1168–1176 (1991).

Najarian et al., Proc. Natl. Acad. Sci. USA 82:2627 (1985).

Najita and Sarnow, Proc. Natl. Acad. Sci. USA 87:5846–5850 (1990).

Nicholson et al., J. Virol 65:5886 (1991).

Nomoto A, et al., Complete nucleotide sequence of the attenuated poliovirus Sabin 1 strain genome, Proc. Natl Acad Sci U S A. 1982 Oct;79(19): 5793–7.

Ohara et al., Virology 164:245 (1988).

Okamoto et al., "Full–length sequence of a hepatitis C virus genome having poor homology to reported isolates: comparative study of four distinct genotypes," Virology 1992 May;188(1):331–41.

Okamoto et al., Gen. Virol 72:2697–2704 (1991).

Palmenberg et al., Nucl. Acids Res. 12:2969–29851 (1984).

Paul et al., Virus Res. 8:153–171 (1987).

Peabody DS, et al., "Effect of upstream reading frames on translation efficiency in simian virus 40 recombinants,"Mol Cell Biol. 1986 Jul;6(7):2704–11.

Peabody DS, and Berg P. "Termination–reinitiation occurs in the translation of mammalian cell mRNAs." Mol Cell Biol. 1986 Jul;6(7):2695–703.

Peaver et al., Virology 165:1 (1988).

Peaver et al., J. Virol. 61:1507 (1987).

Pelletier and Soneberg, J. Virol. 63:441 (1989).

Pelletier J. and Sonenberg N. "Internal Initiation of translation of eukaryotic mRNA directed by a sequence derived from poliovirus RNA," Nature. 1988 Jul. 28;334(6180):320–5.

Pelletier et al., Mol. Cell. Biol 8:1103–1112 (1988).

Pelletier et al., J. Virol 62:4486 (1988).

Pestova et al., "Translation of Poliovirus RNA: Role of an Essential cis–Acting Oligopyrimidine Elements Within the 5' Nontranslated Region and Involvement of a Cellular 57–Kilodalton Protein," J. Virol 65:6194–6204 (1991).

Pestova et al., "Distinct Models of Poliovirus Polyprotein Initiation in Vitro," Virus Research 14:107–118 (1989).

Pihl–Carey, K., "Isis to Restructure as Crohn's Disease Drug Fails in Phase III," BioWorld Today 10(239):1–2 (1999).

Pilder et al., Mol Cell. Biol. 6:470–476 (1986).

Pilipenko et al., "Procaryotic–like cis Elements in the Cap–Independent Internal Translation on Picornavirus RNA ," Cell 68: 119–131 (1992).

Pilipenko et al., Virology 168:201 (1989).

Plotch et al., Cell 23:847–858 (1981).

Pollard et al., J. Virol. 63:4949–4951 (1989).

Qian et al., Mol. Cell. Biol. 11:5312–5320 (1991).

Racaniello & Baltimore Proc. Natl. Acad. Sci. USA 78–4884–4891 (1981)

Remington's Pharmaceutical Sciences, Mack Published Co. A.R. Gennaro ed. (1985)

Rice and Roberts, J. Virology 47:529–539 (1983).

Robertson et al, J. Virol 54:651 (1985),

Roy et al., J. Virology 63:632–640 (1991).

Ryan et al., J. Gen Virol 71:2291–2299 (1990).

Samuel, "The elF–2.–alpha Protein Kinases, Regulators of Translation in Eukaryotes from Yeast to Human," J. Bio. Chem. 268:7603–7606 (1993).

Scheper et al., "The 5' Untranslated REgion of Encephalomyocarditis Virus Contains a Sequence For Very Efficient Binding of Eukaryotic Initiation Factor elF–2/2B," Biochem. Biophys. Acta 1089:220–226 (1991).

Schleiss et al., J. Virology 65:6782–6789 (1991).

Sen and Lengyel, "The Interferon System," J. Bio. Chem 267:5017–5020 (1992).

Shih et al., "Effects pf cDMA Hybridization on Translation of Encephalomycarditis Virus RNA," J. Virol. 61:2033–2037 (1987).

Sikorski & Heiter, Genetics 122:19–27 (1989).

Skern et al., Nucleic Acids Res. 132111 (985).

Sonenburg, "Measures and Countermeasures In the Modulation of Initation Factor Activities By Viruses," The New Biologisg 2:402–409 (1990).

Sonenberg and Meerovitch, "Translation of Poliovirus mRNA," Enzyme 44:278–291 (1990).

Stanners et al., Cell 11:273–281 (1977).

Stanway G et al., Proc Natl. Acad, Sci, USA 81:1539–1543 (1984).

Stein and Krieg, "Problems in Interpretation of Data Derived from in Vitro and in Vivo Use of Antisense Oligodeoxynucleotides," Antisense Res & Dev. 4:67–69 (1994).

Stull and Szoka, "Antigene, Ribozyme and Aptamer Nucleic Acid Drugs: Progress and Prospects," Pharma eutical Res. 21(4):465–483 (1995).

Takamizawa et al. J. Virology 65:1105–113 (1991).

Thomas and Wagner, Biochemistry 22:1540–1546 (1983).

Thompson et al., Clin, Chem. 35:1878–1881 (1989).

Toyoda et al., J. Mol. Biol. 174::561–585 (1984).

Tracy et al., Virus Res. 3,263–270 (1985

Trono et al., Science 241 :445–448.

Tsuykiyama–Kohara et al.;J. Virol. 66:1476.

Villanueva et al., Gene 23:185–194(1983)..

Wallace, R.W., "Does Antisense Make Sense?" DDT 4(1) 4–5 (1999).

Watson et al., Virology 185:206–216 (1991).

Weddell et al., Proc. Natl. Acad. Sci. USA 82:2618–2622 (1985).

Wilson et al., "HIV Expression Strategies: Ribosomal Framshifting Is Directd by a Short Sequence in Both Mammalian and Yeast Systems," Cell 55:1559 (1988).

Whiterell et al., Biochemistry 32:8268 (1993).

Wyngaarden et al., "Antisense '97: A roundtable on the state of the industry," Nature Biotechnology 15:519–514 (1997).

Yoo et al., "4' End–Dependent Translation Initiation of Hepatitis C Viral RNA and the Oresence of Putative Positive and Negative Translational Control Elements With the 5' Untranslated Reon," Virology 191:889–899 (1992).

Zhang et al., Antimicrob Agents Chemother 43(2):347–53 (Feb. 1999).

* cited by examiner ava1
5' CAC CTG GGT TCG ACA 3'
3' GUG GAC CCA AGC UGU 5'
ODN 9/15 GC
VA RNA 113-127 ava2
5' CGG TAA CCG CAT GGA 3'
3' GCC AUU GGC GUA CCU 5'
ODN 9/15 GC
VA RNA 92-106 ava3
5' AAC CCC GGT CGT CCG 3'
3' UUG GGG CCA GCA GGC 5'
ODN 11/15 GC
VA RNA 48-62 ava9
5' CAC CTG GGT TCG 3'
3' GUG GAC CCA AGC 5'
ODN 8/12 GC
VA RNA 116-127 ava15
5' TCG AAC CCC GGT CGT CCG CCA TGA TAC 3'
3' AGC UUG GGG CCA GCA GGC GGU ACU AUG 5'
ODN 17/27 GC
VA RNA 39-65

SEQUENCE LISTING (1) GENERAL INFORMATION:

(iii) NUMBER OF SEQUENCES: 33

(2) INFORMATION FOR SEQ ID NO: 1:

(i) SEQUENCE CHARACTERISTICS:
      (A) LENGTH: 1515 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

```
ATGGTGGCCC CCGGCTCTGT GACCAGCCGG CTGGGCTCGG TGTTCCCTTT CCTGCTGGTC      60

CTGGTGGACC TGCAGTACGA AGGTGCTGAA TGTGGAGTAA ATGCAGATGT TGAGAAGCAT     120
```

```
CTGGAATTGG GCAAGAAGCT GCTCGCAGCC GGACAGCTCG CGGATGCGTT ATCTCAGTTT      180

CACGCTGCAG TAGATGGTGA CCCTGATAAC TATATTGCTT ACTATCGGAG AGCTACTGTC      240

TTTTTAGCTA TGGGCAAATC AAAAGCAGCA CTTCCTGATT TAACTAAAGT GATTGAATTG      300

AAGATGGATT TCACTGCAGC AAGATTACAG AGAGGTCACT TATTACTCAA ACAAGGAAAA      360

CTTGATGAAG CAGAAGATGA TTTTAAAAAA GTGCTCAAGT CAAATCCAAG TGAAAATGAA      420

GAGAAGGAGG CCCAGTCCCA GCTTGTCAAA TCTGATGAAA TGCAGCGTCT GCGCTCACAA      480

GCACTGGATG CCTTTGAGAG CTCAGATTTT ACTGCTGCTA TAACCTTCCT TGATAAGATT      540

TTAGAGGTTT GTGTTTGGGA TGCAGAACTT CGAGAACTTC GAGCTGAATG TTTTATAAAA      600

GAAGGGGAAC CTAGGAAAGC GATAAGTGAC TTAAAAGCTT CATCAAAATT GAAAAACGAT      660

AATACTGAGG CATTTTATAA AATCAGCACA CTCTACTATG AACTAGGAGA CCATGAACTG      720

TCTCTCAGTG AAGTTCGTGA ATGTCTTAAA CTTGACCAGG ATCATAAAAG GTGTTTTGCA      780

CACTATAAAC AAGTAAAGAA ACTGAATAAG CTGATTGAGT CAGCTGAAGA GCTCATCAAA      840

GAAGGCAGGT ACACAGATGC AATCAGCAAA TATGAATCTG TCATGAAAAC AGAGCCAGGT      900

GTTCATGAAT ATACAATTCG TTCAAAAGAA AGGATTTGCC ACTGCTTTTC TAAGGATGAG      960

AAGCCTGTTG AAGCTATTCG AGTATGTTCA GAAGTTTTAC AGGTGGAACC TGACAACGTG     1020

AATGCTCTGA AGACCGAGC AGAGGCCTAT TTAATAGAAG AAATGTATGA TGAAGCTATT     1080

CAGGATTATG AAACTGCTCA GGAACACAAT GAGAATGATC AGCAGATTCG AGAAGGTCTG     1140

GAGAAAGCAC AGAGGCTACT GAAACAGTCA CAGAGACGAG ATTATTACAA AATCTTGGGA     1200

GTAAAAAGAA ATGCCAAAAA GCAAGAAATC ATTAAAGCAT ACCGAAAATT AGCACTGCAG     1260

TGGCACCCAG ACAACTTCCA GAACGAAGAA GAAAAGAAAA AAGCTGAGAA GAAGTTCATT     1320

GACATAGCAG CTGCTAAAGA AGTCCTCTCC GATCCAGAAA TGAGGAAGAA GTTTGATGAC     1380

GGAGAAGACC CCCTGGACGC AGAGAGCCAA CAAGGAGGTG GCGGCAACCC TTTCCACAGG     1440

AGCTGGAACT CATGGCAAGG GTTCAGTCCC TTTAGCTCAG GCGGACCTTT TAGATTTAAA     1500

TTCCACTTCA ATTAA                                                     1515

(2) INFORMATION FOR SEQ ID NO: 2:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:

AATAGAATTC TAATACGACT CACTATAGGG ACACTTGCTT TTGACAC                    47

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

ATAAGGTACC TCTGTCTGTT TTGGGGG                                          27
```

(2) INFORMATION FOR SEQ ID NO: 4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

AATACTGCAG TGATCATGGA AGACGCCAAA AACATAAAG                               39

(2) INFORMATION FOR SEQ ID NO: 5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

AATAAAGCTT GGGCCCTTAC AATTTGGACT TTCCGC                                   36

(2) INFORMATION FOR SEQ ID NO: 6:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

AATAGGTACC ATGGAGAAAA AAATCACTGG ATATACC                                37

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

AATAGGATCC TTACGCCCCG CCCTGCC                                              27

(2) INFORMATION FOR SEQ ID NO: 8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

AATAGGATCC TTAAAACAGC GGATGGG                                              27

(2) INFORMATION FOR SEQ ID NO: 9:

(i) SEQUENCE CHARACTERISTICS:

(A) LENGTH: 48 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

AAAACTGCAG CATGCTGATC ACAGTATATG TATATATATG CTGTGACC                48

(2) INFORMATION FOR SEQ ID NO: 10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

AGTAGTCGGT CCCGTCCCGG AATTGCGCAT TACG                               34

(2) INFORMATION FOR SEQ ID NO: 11:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO: 11:

Ala Glu Ala Tyr Leu Ile Glu Glu Met Tyr Asp Glu Ala Ile Gly Asp
 1               5                  10                  15

Tyr Glu Thr Ala
            20

(2) INFORMATION FOR SEQ ID NO: 12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

GAAGGAAGAT GTATCGATCG AAAGC                                        25

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Modified Base
        (B) LOCATION: 3
        (D) OTHER INFORMATION: WHERE N REPRESENTS INOSINE (xi) SEQUENCE DESCRIPTION: SEQ ID NO: 13:

GCNGTTCTCA GTAAGTCTCT G                                            21

(2) INFORMATION FOR SEQ ID NO: 14:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

Gln Asp Tyr Glu Thr Ala
1               5

(2) INFORMATION FOR SEQ ID NO: 15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

GACTCGAGGA TCCGAATTCT TTTTTTTTTT TTTTTT                                       36

(2) INFORMATION FOR SEQ ID NO: 16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

GACGCGACCA TCCGAATTC                                                          19

(2) INFORMATION FOR SEQ ID NO: 17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

GCTGAAGAGC TCATCAAAG                                                          19

(2) INFORMATION FOR SEQ ID NO: 18:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 18:

AGCAAAAGCA GGGUAGAUAA UCACUCACUG AGUGACAUCA AAAUC                              45

(2) INFORMATION FOR SEQ ID NO: 19:

(i) SEQUENCE CHARACTERISTICS:
    (A) LENGTH: 159 base pairs
    (B) TYPE: nucleic acid
    (C) STRANDEDNESS: single
    (D) TOPOLOGY: linear (ii) MOLECULE TYPE: RNA (xi) SEQUENCE DESCRIPTION: SEQ ID NO: 19:

GGGCACUCUU CCGUGGUCUG GUGGAUAAAU UCGCAAGGGU AUCAUGGCGG ACGACCGGGG      60

UUCGAACCCC GGAUCCGGCC GUCCGCCGUG AUCCAUGCGG UUACCGCCCG CGUGUCGAAC     120

CCAGGUGUGC GACGUCAGAC AACGGGGGAG CGCUCCUUU                            159

(2) INFORMATION FOR SEQ ID NO: 20:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 20:

GGGCACUCUU CCGUGGUCUG GUGGAUAAAU UCGCAAGGGU AUCAUGGCGG ACGACCGGGG      60

UUCGAACCCC GGAUCCGGCC GUCCGCCGUG AUCCAUGCGG UUACCGCCCG CGUGUCGAAC     120

CCAGGUGUGC GACGUCAGAC AACGGGGGAG CGCUCCUUU                            159

(2) INFORMATION FOR SEQ ID NO: 21:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

CACCTGGGTT CGACA                                                       15

(2) INFORMATION FOR SEQ ID NO: 22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 22:

GUGGACCCAA GCUGU                                                       15

(2) INFORMATION FOR SEQ ID NO: 23:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

CGGTAACCGC ATGGA     15

(2) INFORMATION FOR SEQ ID NO: 24:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 24:

GCCAUUGGCG UACCU     15

(2) INFORMATION FOR SEQ ID NO: 25:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

AACCCCGGTC GTCCG     15

(2) INFORMATION FOR SEQ ID NO: 26:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 26:

UUGGGGCCAG CAGGC     15

(2) INFORMATION FOR SEQ ID NO: 27:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 27:

CACCTGGGTT CG     12

(2) INFORMATION FOR SEQ ID NO: 28:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 28:

GUGGACCCAA GC     12

(2) INFORMATION FOR SEQ ID NO: 29:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 29:

TCGAACCCCG GTCGTCCGCC ATGATAC                                          27

(2) INFORMATION FOR SEQ ID NO: 30:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 30:

AGCUUGGGGC CAGCAGGCGG UACUAUG                                          27

(2) INFORMATION FOR SEQ ID NO: 31:

(i) SEQUENCE CHARACTERISTICS:
        (A) LENGTH: 627 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 31:

UUAAAACAGC GGAUGGGUAU CCCACCAUUC GACCCAUUGG GUGUAGUACU CUGGUACUAU        60

GUACCUUUGU ACGCCUGUUU CUCCCCAACC ACCCUUCCUU AAAAUUCCCA CCCAUAUGAA       120

ACGUUAGAAG CUUGACAUUA AAGUACAAUA GGAGGCGCCA UAUCCAAUGG UGUCUAUGUA       180

CAAGCACUUC UGUUUCCCCG GAGCAGGUAU AGGCUGUACC CACUGCCAAA AGCCUUAACC       240

GUUAUCCGCC AACCAACUAC GUAACAGUUA GUACCAUCUU GUUCUUGACU GGACGUUCGA       300

UCAGGUGGAU UUCCCCUCCA CUAGUUUGGU CGAUGAGGCU AGGAAUUCCC CACGGGUGAC       360

CGUGUCCUAG CCUCGUGGCG GCCAACAGCU UAUGCUGGGA CGCCCUUUUA AGGACAUGGU       420

GUGAAGACUC GCAUGUGCUU GGUUGUGAGU CUCCGGCCCC UGAAUGCGGC UAACCUUAAC       480

CCUGGAGCCU UAUGCCACGA UCCAGUGGUU GUAAGGUCGU AAUGCGCAAU UCCGGGACGG       540

GACCGACUAC UUUGGGUGUC CGUGUUUCUC AUUUUUCUUC AUAUUGUCUU AUGGUCACAG       600

CAUAUAUAUA CAUAUACUGU GAUCAUG                                         627

(2) INFORMATION FOR SEQ ID NO: 32:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 32:

GCGTCGACTA ATACGACTCA CTATAGGGAG TCTTATATAA TAGATATACA AAAC             54

```
(2) INFORMATION FOR SEQ ID NO: 33:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 33:

GGGAAATTTT TATTGGCGAG TAAACCTGG                                      29
```

METHOD FOR SELECTIVE INACTIVATION OF VIRAL REPLICATION

RELATED APPLICATION

This application is a continuation of U.S. Ser. No. 09/724,380, filed Nov. 28, 2000, which is a continuation of U.S. Ser. No. 08/925,156, filed Sep. 8, 1997, now U.S. Pat. No. 6,156,496, which is a divisional of U.S. Ser. No. 08/221,816, filed Apr. 1, 1994, now U.S. Pat. No. 5,738,985, which is a continuation-in-part of U.S. Ser. No. 08/042,024, filed Apr. 2, 1993, now abandoned, entitled "Method for Selective Inactivation of Viral Replication," the whole of which (including drawings, if any) is hereby incorporated by reference.

This invention relates to methods for screening for agents useful for treatment of viral infection, the novel agents identified using such screening methods, and their use as antiviral agents.

BACKGROUND OF THE INVENTION

A variety of agents are presently used to combat viral infection. These agents include interferon, which is a naturally-occurring protein having some efficacy in combat of certain selected viral diseases. In addition, agents such as AZT are used in the combat of an immunodeficiency disease, referred to commonly as AIDS, caused by the virus HIV-1.

Drug and Market Development, Vol 3. No. 9, pp. 174–180 (Feb. 15, 1993), describes antiviral drug development. It states:

The difficulties encountered in drug treatment of most infections pale when compared to viral infections. For example, it is at least theoretically (and often in practice) possible to attack a bacterium without harming the host. Unlike bacteria however, viruses replicate inside cells and utilize cellular machinery of the host for replication. As a result, development of antiviral therapeutics often represents a compromise between preferable killing, or at least arresting replication of, the virus, and not harming the host, or at worst, doing only minimal damage which can be justified by the potential gain.

It states that viral specific events can be targeted including:

Virus attachment to cell membranes and penetration in cells;

Virus uncoating;

Virus nucleic acid synthesis;

Viral protein synthesis and maturation; and

Assembly and release of infectious particles. Specifically with regard to viral protein synthesis the authors state:

In contrast to nucleic acid synthesis, viral protein synthesis utilizes host ribosomes (ribosomes are cell structures essential for translation of mRNA into protein) and mostly host-derived supplementary factors. As a result, protein synthesis inhibitors, in general, are as likely to exhibit host toxicity as they are to exert antiviral effects. Antisense oligonucleotides, however, may be of value in specifically inhibiting viral protein synthesis. Briefly, antisense oligonucleotides are short DNA fragments that are complementary to mRNA (sense strands) and can prevent mRNA-directed protein synthesis by binding to mRNA. RNA molecules have also been constructed to contain sequences complementary to those of sense DNA strands (and their corresponding mRNA). Although antisense constructs have been shown to inhibit viral protein synthesis in vitro, their effectiveness in vivo has not yet been conclusively demonstrated. Among others, current challenges for oligonucleotide therapeutics include delivery to virus-infected cells, the stability of such molecules in vivo and distribution throughout the body.

Ribosome inactivators represent another approach for viral protein synthesis inhibition. GLQ223 (Genelabs; Redwood City, Calif.) is a ribosome inactivator undergoing clinical testing (GLQ223 is a purified preparation of trichosanthin (cucumber plant derivative)). A ribosome inactivator would interfere with cellular translation machinery, effectively preventing generation of new viral proteins.

Sonenburg, 2 The New Biologist 402, 1990 describes virus host interactions at the level of initiation of translation and states that two initiation factors eIF-2 and eIF-4F play significant roles in a number of virus host interactions. He states "[a]n understanding of the mechanisms responsible for these virus-host interactions is of great significance for future therapeutic approaches to viral disease."

SUMMARY OF THE INVENTION

The present invention relates to methods for screening for agents which are effective in inhibiting the translational system used by a virus during infection of a host cell. The screening method utilizes a protocol in which potentially useful agents are brought into contact with appropriate macromolecular sequences, e.g., viral nucleic acid sequences or relevant protein sequences, in order to determine whether those agents can specifically inhibit use of those sequences. Viruses use a variety of methods for taking over a host translational system, and it is these methods that can be specifically targeted by methods of the present invention. Once isolated, the viral specific agents can be formulated in therapeutic products (or even prophylactic products) in pharmaceutically acceptable formulations, and used for specific treatment of viral disease with little or no effect on uninfected virus host cells.

Specifically, in one aspect, applicant provides a screening method in which a target virus nucleic acid sequence or domain responsible for preferential translation of viral RNA over host RNA is used in a selection protocol. While several specific examples of such viral nucleic acid sequences or domains are provided below in the form of IRES elements, 5'-untranslated regions containing specific viral sequences, and upstream open-reading frames containing such sequences, these are used only to exemplify a general method by which other virus nucleic acid sequences can be used in such protocols. Use of any one of these virus nucleic acid sequences within a cell translation system provides a means by which anti-viral agents can be discovered.

Applicant notes that the claimed method does not include targeting of agents to viral sequences involved in frame shifting (which is not a target nucleic acid that is preferentially translated as defined herein), such as described by Dinman and Wickner, 66 J. Virol. 3669, 1992; Jacke et al., 331 Nature 280, 1988; Wilson et al., 55 Cell 1159, 1988; Inglis and Brierly, WO 90/14422; and Goodchild and Zamecnik, WO 87/07300.

Any agent which binds to such viral nucleic acid and/or which causes a significant reduction in translation of viral message is potentially useful in the present invention. Such agents can be screened to ensure that they are specific to viral translation systems and have no effect on uninfected host cell translation systems such that the agent can be used in a therapeutic or prophylactic manner. If such agents have some effect on host cell systems they may still be useful in therapeutic treatment, particularly in those diseases which are life threatening, such as HIV-1 infection.

Such agents may interact either directly with the target viral nucleic acid, for example, by hybridization with the nucleic acid, e.g., antisense RNA or DNA, or may bind or interact with other components of the viral translation system (i.e., those host and/or viral components whether nucleic acid and/or protein which allow translation of viral mRNA to occur in vivo), such as proteins used by the virus to promote translation of its RNA, rather than host RNA involved in that system, e.g., antibodies. Additionally, agents may include any nucleic acid molecule which binds to viral or cellular components which otherwise would partake in preferential viral nucleic acid translation, but upon binding said nucleic acid molecule become unable to be preferentially translated. However, while antisense nucleic acid and antibodies may exemplify aspects of the present invention, applicant is particularly concerned with identification of agents of low molecular weight (less than 10,000, preferably less than 5,000, and most preferably less than 1,000), which can be more readily formulated as useful antiviral agents. Thus, in a preferred embodiment, the invention features such low molecular weight agents, and not antisense molecules or antibodies.

Thus, in a first aspect the invention features a method for screening for an antiviral agent. The method includes providing a target viral translation nucleic acid sequence which allows preferential translation of a viral RNA compared to a host RNA under virus infection conditions. The method may involve a simple assay to detect binding of an agent to this nucleic acid. Preferably, however, the target viral translation nucleic acid sequence is translationally linked to RNA encoding a reporter polypeptide. The method then further includes contacting the target viral translation nucleic acid sequence with a potential antiviral agent under conditions which allow synthesis of the reporter polypeptide in the absence of the agent. The method finally includes determining whether the agent reduces the level of translation of the reporter polypeptide. Any agent which does reduce this level is potentially a useful antiviral agent.

Specifically, the method involves determining whether a potential agent interacts with a virus or cellular component which allows or prevents preferential translation of a virus RNA compared to a host RNA under virus infection conditions; and determining whether any interaction of the agent with the component reduces the level of translation of a RNA of the virus.

By "screening" is preferably meant a process in which a large number of potentially useful agents are processed in the method of this invention. It is generally a process distinct from a single experiment in which a single agent is studied in detail to determine its method of action.

By target viral translation nucleic acid sequence is meant any nucleic acid which allows preferential translation of translationally associated RNA under viral infection conditions. Such nucleic acid is exemplified by IRES elements which allow cap-independent translation of associated ribonucleic acid, and 5' untranslated regions of influenza virus RNA which allow preferential cap-dependant translation of associated RNA.

By preferential translation is meant that the RNA is translated at a higher rate or with higher yield of protein than host cell RNA under virus-infection conditions. In addition, the host cell RNA may be translated at a slower rate or with lower protein yield than in non-infected conditions. Such preferential translation cn be readily detected as described below. In the case of most viruses, preferential expression of viral proteins means that synthesis of viral proteins represents at least 50% of total de novo protein synthesis, as may be detected, for example, by pulse-labeling experiments in viral-infected cells. In such cases, viral proteins may usually be distinguished as major bands when labeled proteins are separated by gel electrophoresis. In the case of retroviruses, preferential expression of viral proteins means that the level of viral proteins synthesized increases disproportionately beyond the level of viral RNA synthesized (Cullen, Cell 46: 973, 1986). Such a disproportionate increase can be detected by quantitating levels of viral RNA and protein synthesis in infected cells by, for example, Northern blotting and nuclease protection assays for RNA synthesis and immuno-precipitations and gel electrophoresis for labeled proteins.

By virus infection conditions is simply meant conditions within a host cell after infection with the target virus such that the viral translation system is operative. Such a viral translation system will usually include host cell proteins, nucleic acids and other components.

By reporter polypeptide is simply meant a peptide which is readily detectable, either by providing a calorimetric signal under certain environmental conditions or some other signal well known to those of ordinary skill in the art, as described below.

In preferred embodiments, the component is a protein or a nucleic acid; the component is virus encoded or host cell encoded; the component is a macromolecule selected from an RNA sequence domain, a DNA sequence domain, an initiation factor, and elongation factor, a termination factor, a transcription factor, a ribosomal protein, a glycosylase, a deglycosylase, a prenylatinq and deprenylating enzyme, a transferase, a polymerase, a synthetase, an ADP ribosylating enzyme, an ADP ribosylase, a kinase, a lipase, a myristylating or demyristylating enzyme, a phosphorylase, a protease, a rRNA, a tRNA, a ribonuclease, and a deoxyribonuclease; the viral translation signal nucleic acid sequence is selected from the group consisting of IRES elements, 5' or 3' untranslated regions, and upstream open reading frames, or any other viral target translation nucleic acid that affords preferential translation of viral mRNA over host cell mRNA when the host cells are infected by the virus; and the virus from which that signal is selected is chosen from the picornavirus family, Hepatitis viruses A, B, and C, influenza virus, HIV, Herpes virus, and cytomegalovirus.

In other preferred embodiments, the sequence domain is translationally linked to RNA encoding a reporter polypeptide, and the second determining step includes determining whether the agent alters the level of translation of the reporter polypeptide; the component is a protein or a polypeptide, and the determining steps include providing the component in a translation mixture with RNA encoding a reporter polypeptide, and determining whether the agent alters expression of the reporter polypeptide in the mix.

In more preferred embodiments, the method further includes determining whether an agent active in the above method has little or no effect on the translational machinery of an uninfected viral host cell, and further determining whether the agent is active under in vivo conditions. Such agents are then formulated in a pharmaceutically acceptable buffer.

By pharmaceutically acceptable buffer is meant any buffer which can be used in a pharmaceutical composition prepared for storage and subsequent administration, which comprise a pharmaceutically effective amount of an agent as described herein in a pharmaceutically acceptable carrier or diluent. Acceptable carriers or diluents for therapeutic use are well known in the pharmaceutical art, and are described, for example, in *Remington's Pharmaceutical Sciences,* Mack Publishing Co. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

In a second aspect, the invention features a method for treating a subject infected with a virus having a viral translation signal nucleic acid sequence, by administering to that subject a therapeutically effective amount of an antiviral agent able to selectively block translation of viral RNA naturally linked to the viral translation signal nucleic acid sequence.

By "therapeutically effective amount" is meant an amount that relieves (to some extent) one or more symptoms of the disease or condition in the patient. Additionally, by "therapeutically effective amount" is meant an amount that returns to normal, either partially or completely, physiological or biochemical parameters associated with or causative of a viral disease. Generally, it is an amount between about 1 nmole and 1 μmole of the molecule, dependent on its $EC_{50}$, and on the age, size, and disease associated with the patient.

In a third related aspect, the invention features novel antiviral agents discovered by the methods described above. It also includes novel pharmaceutical compositions which include antiviral agents, discovered as described above, and formulated in pharmaceutically acceptable formulations.

In a fourth aspect, the intention features the use of nucleic acid constructs containing isolated viral nucleic acid translationally linked to a reporter-encoding sequence to discover antiviral agents, and kits for use of these constructs in antiviral agent screening methods.

In a fifth aspect, the present invention features a screening method for antiviral agents active at modulating the activity of other, non-nucleic acid, macromolecules involved in the viral mRNA translation system. For example, the method for screening agents includes identifying those effective at inhibiting macromolecules that interfere with the activity of such macromolecules, e.g., agents which allow the p68 kinase in a cell to exhibit its activity. The invention also features a method of employing such agents for inhibiting replication of virus in eukaryotic host cells.

Thus, the invention includes a method of inhibiting viral replication in a host eukaryotic cell, e.g., where the virus produces a viral inhibitor which interferes with the activation of a host-cell interferon-induced, double-stranded RNA-activated protein kinase. The method includes administering to the cells, an agent able to block the effect of the viral inhibitor in interfering with the activation of the protein kinase.

In a related aspect, the invention features a virus which produces a viral inhibitor able to block binding of double-stranded RNA to the protein kinase, and the agent administered is one able to block the binding of the viral inhibitor to the protein kinase.

The agent may be selected, for example, by forming a mixture composed of protein kinase, the viral inhibitor, and the agent, incubating the components of the binding mixture under conditions effective to bind the protein kinase to the viral inhibitor, in the absence of the agent, and examining the mixture for the presence of binding of the protein kinase to the viral inhibitor, to determine whether the presence of the test agent has inhibited binding the protein kinase to the viral inhibitor.

Alternatively, the agent may be selected by forming a mixture composed of protein kinase, the viral inhibitor, and the agent, incubating the components of the mixture under conditions effective to autophosphorylate the protein kinase in the absence of the viral inhibitor, examining the mixture for the presence of protein kinase activity, and selecting the agent if it is able to prevent inhibition of protein kinase activity.

In specific examples, where the virus is an adenovirus, and the viral inhibitor is a VAI RNA molecule (also known as VA 1 and $VARNA_1$); the virus is human immunodeficiency virus (HIV), and the viral inhibitor is a TAR region of the HIV genome; and the virus is an Epstein-Barr virus, and the viral inhibitor is an EBER-1 RNA.

In another related aspect, the viral inhibitor is effective to activate a host-cell p58 protein which is able, in activated form, to block the activation of the protein kinase, or to block the activity of already activated protein kinase, and the agent is one which blocks the interaction of the viral inhibitor through p58 protein on the kinase. The agent may be selected, for example, by forming a mixture composed of protein kinase, the p58 protein (an active form), and the agent, and then incubating the components of the mixture under conditions effective to autophosphorylate the protein kinase, when the p58 protein is absent, examining the mixture for the presence of protein kinase activity, and selecting the agent if it is able to reduce inhibition of protein kinase activity, when p58 is present.

In another related aspect, the invention includes a method for screening agents effective to inhibit viral replication in a host eukaryotic cell, where the virus is one able to produce a viral inhibitor which interferes with the activation of the host-cell interferon-induced, double-stranded RNA-activated protein kinase. The method includes incubating a mixture containing the protein kinase, the viral inhibitor, and the agent to be tested, under conditions effective to cause viral inhibitor interference with the activation of the protein kinase, and examining in mixture for such interference.

The method of this invention can also be used for screening an agent effective to inhibit replication in a host cell of a virus which produces a viral inhibitor capable of binding to the protein kinase, to inhibit binding of double-stranded RNA to the protein kinase. In this method, the mixture is incubated under conditions effective to bind the viral inhibitor to the protein kinase, and the mixture is examined for binding of the viral inhibitor to the protein kinase. The incubating may be carried out, for example, in solution phase, and the examining step includes passing the mixture through a filter which retains the viral inhibitor only when the inhibitor is bound to the protein kinase. Alternatively, the protein kinase may be bound to a solid support, the viral inhibitor labeled with a reporter, and the examining step performed by measuring the amount of reporter bound to the solid support. In addition, the incubating may be carried out under conditions in which the protein kinase is autophosphorylated, in the absence of binding to the viral inhibitor, and the examining step performed by determining the extent of phosphorylation of the p68 kinase.

In another related aspect, the method of this invention is used for screening agents effective in blocking viral replication of a virus which produces an viral inhibitor effective to activate a p58 host-cell protein which in activated form is effective to block autophosphorylation of the protein kinase or to block activity of the phosphorylated kinase. Here the mixture formed includes the p58 host-cell protein, the incubating step is carried out under conditions in which the protein kinase would be autophosphorylated in the absence of p58, and the mixture is examined for reduction of inhibition of protein kinase activity.

In still another aspect, the protein kinase and viral inhibitor are expressed in a yeast cell which is constructed to increase the expression of a marker protein in the presence of activated protein kinase, and the yeast cells are examined for increased expression of the marker protein. This aspect concerns use of a yeast cell in screening agents effective to inhibit viral replication in a host eukaryotic cell, where the virus is able to produce a viral inhibitor which interferes with the activation of the host-cell interferon-induced, double-stranded RNA-activated protein kinase. The cell includes (a) an expressible gene encoding a mammalian interferon-induced, double-stranded RNA-activated protein kinase, (b) a reporter gene whose expression in increased by activation of the protein kinase, and (c) a viral gene for producing a viral inhibitor able to block activation of the protein kinase.

In yet other preferred embodiments, the method of this invention includes forming a protein translation mixture which includes (i) a viral mRNA construct, the mRNA construct comprising (a) an internal ribosome entry site (IRES) region and downstream of the IRES region, a first reporter protein coding region, (ii) ribosomes, and (iii) an agent to be tested, incubating the components of the translation mixture under conditions effective to produce from the first reporter protein coding region a reporter protein, and examining the mixture for the presence of reporter protein produced by such translation mixture, and the agent is a useful anti virus agent if the reporter protein produced in the presence of the test agent is less than an amount of reporter protein produced in the absence of the test agent.

Preferably, the IRES region is derived from a picornavirus IRES region sequence; the IRES sequence is selected from the group consisting of an enterovirus, rhinovirus, cardiovirus, and aphthovirus IRES sequence; the IRES region is selected from the group consisting of an hepatitis A virus IRES sequence, an hepatitis B virus sequence and an hepatitis C virus IRES sequence; the protein translation mixture is a cell-free extract; the 5'-end of the viral mRNA construct includes a eukaryotic mRNA 5'-terminal cap and untranslated region (UTR) and downstream of the cap and UTR region, a second reporter protein; and the translation mixture is contained in a cell.

In another example, the method includes forming a binding mixture comprising a cellular or viral translation initiation protein, an IRES element ribonucleotide sequence, and an agent to be tested, incubating the components of the binding mixture under conditions effective to bind the initiation protein to the IRES element, and examining the mixture for the presence of binding of the initiation protein to the IRES element. The agent is a useful antivirus agent if the extent of binding of the initiation protein to the IRES element is less than that observed in the absence of the agent.

Preferably, the cellular or viral translation initiation protein is selected from the group consisting of p52 and p57; the cellular or viral translation initiation protein is bound to a solid support, the IRES element is labeled with a reporter, and the examining includes measuring the amount of reporter bound to tile solid support; the IRES element RNA is bound to a solid support, the cellular or viral translation initiation protein is labeled with a reporter, and the examining includes measuring the amount of reporter bound to the solid support; a terminal region of the IRES element is bound to a complementary DNA sequence, and the DNA sequence is linked to the solid support; and the method further includes the step, after the incubating step, of adding to the incubation mixture an RNAase capable of cleaving free RNA but not protein bound RNA, and the binding of the initiation protein to the IRES element is detected by the presence in the mixture of uncleaved IRES element RNA.

In one example, the examining includes subjecting the mixture to a gel-shift electrophoresis assay.

In still other preferred embodiments, the incubating is carried out in solution phase, and the examining includes passing the mixture through a filter which retains the IRES element only when the element is bound to the cellular or viral translation initiation protein.

In a related aspect, the agent is effective to inhibit viral replication in a host eukaryotic cell, where the virus produces an inhibitor which interferes with the activation or activity of the host-cell interferon-induced, double-stranded RNA-activated protein kinase, and the screening method includes incubating a mixture containing the protein kinase, the inhibitor, and the agent to be tested under conditions effective to cause inhibitor interference with the activation or activity of the protein kinase, and examining the mixture for such interference; or the agent is effective to inhibit viral replication in a host eukaryotic cell, where the host cell produces an inhibitor which interferes with the activation of the host-cell interferon-induced, double-stranded RNA-activated protein kinase, and the method includes incubating a mixture containing the protein kinase, the inhibitor, and the agent to be tested under conditions effective to cause inhibitor interference with the activation of the protein kinase, and examining the mixture for such interference.

Preferably, the method is for use in screening an agent effective to inhibit replication in a host cell of a virus which produces an inhibitor able to bind to the protein kinase, to interfere with the activation of the protein kinase by double-stranded RNA, and the incubating includes incubating the protein kinase, viral inhibitor, and agent under conditions effective to bind the inhibitor to the protein kinase, and the examining includes examining the protein kinase for bound inhibitor; or the incubating is carried out in solution phase, and the examining includes passing the protein kinase, viral inhibitor, and test agent through a filter which retains the inhibitor only when the inhibitor is bound to the protein kinase; or the protein kinase is bound to a solid support, the inhibitor is labeled with a reporter, and the examining includes measuring the amount of reporter bound to the solid support; or the incubating is carried out under conditions in which the protein kinase is autophosphorylated, in the absence of binding to the viral inhibitor, and the examining includes determining the extent of phosphorylation of the p68 kinase; or the method is for use in screening agents effective in blocking viral replication of a virus which produces an inhibitor effective to activate a p58 host-cell protein which in activated form is effective to block activity or activation of the protein kinase, and the mixture formed includes the p58 host-cell protein, the incubating is carried out under conditions in which the protein kinase is activated in the absence of p58, and the examining includes examining the mixture for inhibition of protein kinase activity.

In a preferred embodiment, the protein kinase and inhibitor are expressed in a yeast cell which is constructed to increase the expression of a reporter protein in the presence of activated protein kinase, and the examining includes examining the yeast cells for increased expression of the reporter protein; and the reporter protein is fused GCN4/β-gal protein.

In another aspect, the invention features a yeast cell for use in screening agents effective to inhibit viral replication in a host eukaryotic cell, where the virus produces a viral inhibitor which interferes with the activation of the host-cell interferon-induced, double-stranded RNA-activated protein kinase. The cell includes (a) an expressed gene encoding a mammalian interferon-induced, double-stranded RNA-activated protein kinase, (b) a reporter gene whose expression in increased by activation of the protein kinase, and (c) a viral gene for producing a viral inhibitor able to block activation of the protein kinase. Preferably, the reporter gene is a fused GCN4/β-gal gene.

In a related aspect, the yeast cell for use in screening agents effective to inhibit viral replication in a host eukaryotic cell, where the virus activates or induces a cellular protein to interfere with the activation of the host-cell interferon-induced, double-stranded RNA-activated protein kinase, includes the components (a) and (b) above and (c) a gene encoding a protein which blocks activation of a cellular protein.

Other features and advantages of the invention will be apparent from the following description of the preferred embodiments thereof, and from the claims.

BRIEF DESCRIPTION OF FIGURES

FIG. 3 shows the sequences of antisense species and complementary VAI RNA regions, (SEQ ID NOS:21–30.) i.e., VAI RNA antisense oligodeoxynucleotides (ODN).

FIGS. 5A–5C show human rhinovirus 14 5' NTR sequence and predicted secondary structure (SEQ ID NO:31) (Le, S.-Y., and Zuker, M. (1990) *J. Mol. Bio.* 216, 729–741). The initiating AUG start codon for the polyprotein, at nucleotide ("nt") 625, is shown as a shaded box, non-initiating AUG codons are shown as clear boxes. The YnXmAUG motif found in all picornavirus IRES elements and the 21-base conserved sequence found in all rhinovirus and enterovirus IRES elements are underlined. Nucleotide positions on the rhinovirus genome are marked by numbers.

DESCRIPTION OF THE PREFERRED EMBODIMENTS

Antiviral Agents

Figure 1:
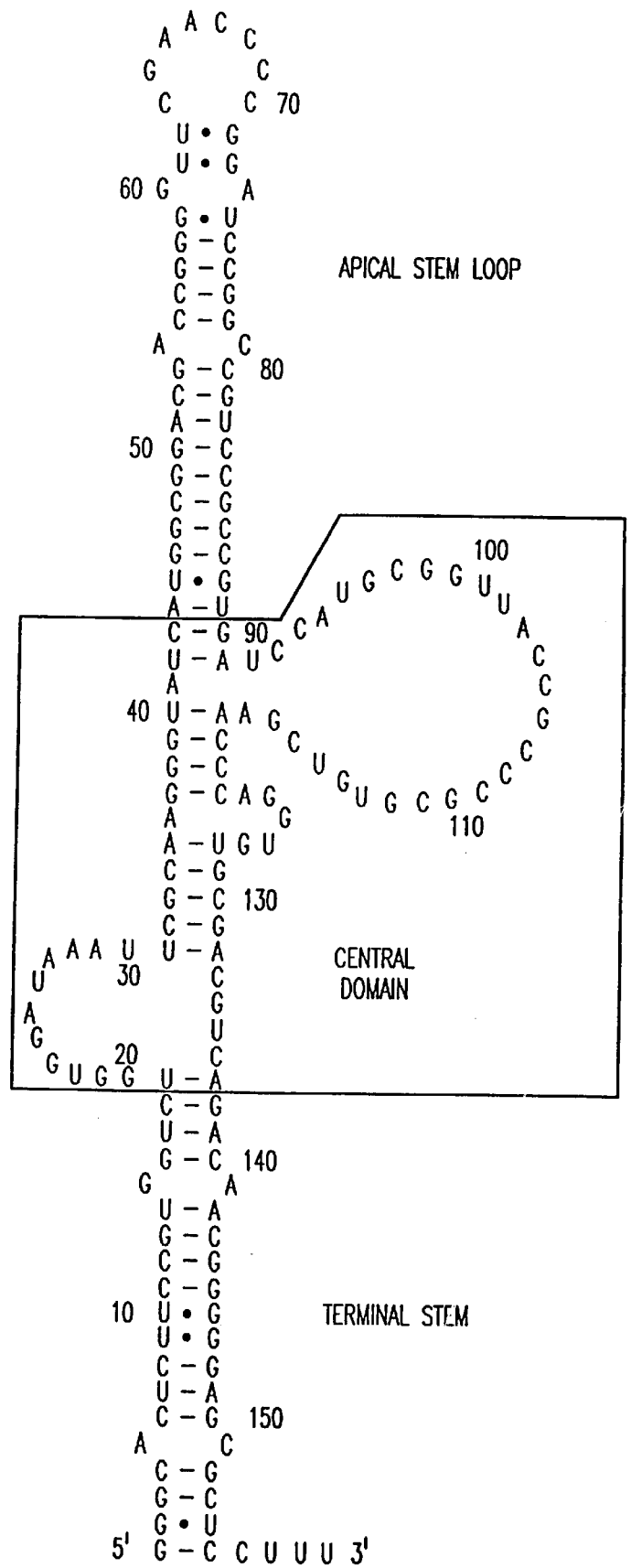
FIG. 1 shows the terminal stem, central domain, and apical stem loop of adenovirus VAI RNA (SEQ ID NO.19) (Ma, Y. and M. B. Mathews. 1993. Comparative analysis of the structure and function of adenovirus associated RNAs. J. Virol. 67:6605–6617).

Given the large number of drugs available for treating infections caused by more complex organisms such as bacteria, it is remarkable how few drugs are available for treating the relatively simple organisms known as viruses. Indeed, most viral diseases remain essentially untreatable. The major difficulty in developing anti-viral drugs is that, unlike bacteria, viruses replicate inside host cells and utilize the machinery of those cells for replication, sharing many nutritional requirements and synthetic pathways with their hosts. As a result, it is difficult to identify agents that kill or arrest replication of a virus without also harming the host. Even those anti-viral drugs that have been approved for use in humans often have side effects which limit their utility.

The majority of existing anti-viral drugs are nucleoside analogs or other agents that exert their effects through an enzyme involved in producing new copies of the viral genetic material, such as a nucleoside kinase or a polymerase or reverse transcriptase or replicase. These analogs are typically metabolized into nucleotide analogs that inhibit production of viral nucleic acid, for example by inhibiting a polymerase or by causing premature chain termination of growing viral nucleic acids. The efficacy of such drugs depends on two key factors. The first is that the target virus utilize, at least one virus-specific enzyme, encoded by the virus and used only by the virus, in the pathways which result in the copying of its genetic material. The second is that this enzyme is more sensitive to the drug or more efficient in utilizing it than any corresponding enzyme in the host. However, because viral and cellular nucleic acid metabolism are so similar, it is difficult to find anti-viral agents that are not used to some extent by host cell enzymes. This limits the dose of anti-viral drug that can be tolerated, which in turn may limit the utility of the drug.

Even in the case where a drug is tolerated at an effective dose, its effectiveness can be reduced markedly by the ability of a virus to mutate relatively rapidly, evolving new versions of the viral enzyme which do not utilize the drug as efficiently or which are less inhibited by the drug.

There is thus a clear need for novel anti-viral drugs that will be effective at doses tolerated by the host and that will be more difficult for viruses to evade by mutation.

The present invention provides novel methods for discovering such drugs and for treating illnesses with the drugs discovered. The methods of this invention are based in the observation that many viruses take over control of protein synthesis (translation of messenger RNA) in cells they infect. The viral proteins are synthesized preferentially over host proteins in infected cells. This preferential synthesis of viral proteins is important to the replication of the virus. Drugs which reduce or prevent the viral takeover of protein synthesis are therefore effective anti-viral agents.

Such drugs have significant advantages over current anti-viral agents. As noted above, the targets for the majority of the latter are enzymes involved in the synthesis of viral nucleic acids, and because host cells also contain enzymes active in the synthesis of nucleic acids it is difficult to hit the viral enzymes without also hitting the host ones. Similar problems are likely to occur for any drug target which is an active catalyst in the synthesis of a material required by both the virus and the host cell. In the methods of the present invention, these problems are avoided because the drug targets are not active catalysts in a synthetic pathway: they are devices used by a virus to secure preferential access to a synthetic pathway (protein synthesis), rather than catalysts in such a pathway. As weapons used by the virus in its attack on the host, these devices do not have any parallels within the host. Drugs which interfere with these devices therefore have minimal side effects on the host.

Such drugs are more effective than current drugs, for two reasons. First, their minimal side effects allow them to be used at higher doses. Second, it is possible for these drugs to be intrinsically more injurious to their targets than is tolerable for drugs whose targets have host homologues, because if the latter drugs are intrinsically too injurious they may harm the host homologues to some extent.

Viruses are also less able to evolve resistance to drugs which target viral translational hijacking devices. These devices must of necessity interact with host-cell components involved in protein synthesis, and the need to maintain these interactions means that the virus is limited in the extent to which it can mutate its hijacking devices. If it mutates too far to avoid a drug, it may no longer be able to hijack protein synthesis. This limitation is particularly problematic for the virus because it may need to make larger changes to evade an hijack-blocking drug than to evade a drug whose target is a synthetic enzyme with a host homologue, because, as noted above, the hijack-blocking drug may be intrinsically more injurious to its target.

In summary, the present invention provides a means to discover and utilize novel anti-viral drugs with important advantages over current such drugs, namely fewer side effects and a reduced likelihood of the evolution of resistant viruses.

The methods of this invention are based in the observation that many viruses take control over the process of protein synthesis (translation of mRNA) in cells they infect. Viruses use a variety of mechanisms to effect this takeover, including but not limited to the use of special viral nucleic acid sequences which ensure preferential translation of viral RNAs (see e.g., Pelletier et al., *Mol. Cell. Biol,*8, 1103–1112, 1988; Trono et al. *Science* 241, 445–448; Sonenberg & Meerovitch, 1990; Garfinkel & Katze, *J. Biol. Chem.* 267, 9383–9390, 1992), recruitment of cellular proteins to interact with these special sequences (see e.g., Jang S K & Wimmer E, *Genes Dev.* 4, 1560–1572, 1990), modification or degradation of host-cell components which participate in translation or its control (see e.g., Katze M G et al., *J. Virology* 62, 3710–3717, 1988, Lee et al., *Proc. Natl. Acad. Sci. USA* 87, 6208–6212, 1990), and disablement of cellular defenses mounted in response to the infection (see e.g., review by Katze M G, *J. Interferon Res.* 12, 241–248, 1992). Any such mechanism used by a virus to ensure preferential translation of viral proteins as compared to host-cell proteins in infected cells can be addressed by the methods of this invention.

These methods are exemplified herein with descriptions of two such mechanisms used by viruses, namely (i) viral interference with a host enzyme known by various names including p68 protein kinase and the interferon-induced double-stranded RNA-activated protein kinase, and (ii) viral nucleic acid sequences responsible for preferential translation of viral RNAs. The use of these examples is in no way intended to limit the scope of the invention.

The protein known as p68 protein kinase is an interferon-induced double-stranded RNA-activated protein kinase. This kinase is activated by the double-stranded RNA typically found in virus-infected cells. Once activated, the kinase phosphorylates the alpha subunit of the initiation factor eIF-2, an event which quickly leads to a block in the initiation stage of translation. The effect is to shut down protein synthesis in the cell, causing that cell to die: something which the multi-cellular infected organism can afford but which the virus cannot. To ensure continued translation in infected cells, different viruses have evolved a variety of mechanisms to prevent or counteract activation of the p68 kinase (reviewed in Katze, 1992). These include viral RNAs which bind to the kinase and prevent binding of the double-stranded RNA activator, as used by adenovirus (reviewed by Mathews M B & Shenk T, *J. Virology* 65, 5657–5662), HIV (Edery et al., *Cell* 56, 303–312, 1989; Gunnery et al., *Proc. Natl. Acad. Sci. USA* 87, 8687–8691, 1990; Roy et al., *J. Virology* 65, 632–640, 1991) and Epstein-Barr virus (Clarke et al., *Eur. J. Biochem* 193, 635–641, 1990; Clarke et al., *Nucl. Acids Res.* 19, 243–248, 1991); viral proteins which bind the double-stranded RNA and prevent it binding to the kinase, as used by vaccinia virus and reovirus (Watson et al., *Virology* 185, 206–216, 1991; Imani and Jacobs, *Proc. Natl. Acad. Sci. USA* 85, 7887–7891, 1988); viral proteins which act as pseudosubstrates of the kinase, as used by vaccinia virus (Beattie et al., *Virology* 183, 419–422, 1991); recruitment of a cellular protein, p58, to block activation of the kinase and inhibit active kinase, as used by influenza virus (Lee et al., 1990); and recruitment of a cellular protein into a complex with RNA (possibly viral double-stranded RNA) which degrades p68, as used by poliovirus (Black et al., *J. Virology,* 67, 791–800, 1993). p68, and the RNAs and proteins just described which interact with it, are examples of a broader class of macromolecules which have been shown to be involved in the seizure or retention by viruses of control of translation in infected cells. Other examples include: the host translational factors eIF2 and eIF3/4B, which are-reported to be impaired in cells infected with vesicular stomatitis virus (VSV) (Centrella and Lucas-Lenard, *J. Virology* 41, 781–791, 1982; Thomas and Wagner, *Biochemistry* 22, 1540–1546, 1983); the product of the VSV gene "P", reportedly responsible for host translational inhibition (Stanners, et al., *Cell* 11, 273–281, 1977); the poliovirus 2A protease, responsible for degrading the p220 subunit of cap-binding protein complex (eIF-4F) in infected cells, and thereby preventing cap-dependent translation of host-cell mRNAs (Etchison et al., *J. Biol. Chem.* 257, 14806–14810, 1982); the cellular protease recruited/ activated by the poliovirus protease 2A to cleave p220 (the poliovirus enzyme does not cleave p220 directly) (Lloyd et al., *Virology* 150, 299–303, 1986); the p220 protein degraded in poliovirus-infected cells; the host initiation factor eIF-4E, another component of the cap-binding protein complex which is dephosphorylated in adenovirus-infected cells to shut off host protein synthesis (Huang and Schneider, *Cell* 65, 271–280, 1991); and the cellular proteins p57 (also known as polypyrimidine tract-binding protein, pPTB), p50 and p52 implicated in the initiation of translation at internal ribosome entry sites within poliovirus and other viral RNAs (Jang and Wimmer, 1990; del Angel et. al., *Proc. Natl. Acad. Sci. USA* 86, 8299–8303, 1989; Meerovitch et al., *Genes Dev.* 3, 1026–1034, 1989; Najita and Sarnow, *Proc. Natl. Acad. Sci. USA* 87, 5846–5850, 1990).

To these examples can be added a variety of macromolecules used by viruses to cut off the supply of host-cell mRNAs and/or favor the production of viral RNAs in infected cells. These include: the vhs gene product of herpes simplex virus (HSV), a virion protein which degrades mRNAs in infected cells (Kwong and Frenkel, *Proc. Natl. Acad. Sci. USA* 84, 1926–1930, 1987; Kwong et al., *J. Virology* 62, 912–921, 1988); another HSV virion protein which binds to a sequence-specific DNA-binding protein in host cells, causing increased transcription from viral gene promoters (Campbell et al., *J. Mol. Biol.* 180, 1–19, 1984); a cap-dependent endonuclease encoded by influenza virus which cleaves nascent host-cell transcripts in the nucleus to provide primers for the synthesis of viral mRNA from the viral RNA genome (Bouloy et al., *Proc. Natl. Acad. Sci. USA* 75, 4886–4890, 1978; Plotch et al., *Cell* 23, 847–858, 1981); nucleases used by influenza virus and poxvirus to degrade host-cell mRNAS (Rice and Roberts, *J. Virology* 47, 529–539, 1983; Inglis S C, *Mol. Cell. Biol* 2, 1644–1648, 1982); viral inhibitors of host-cell RNA polymerase II (the enzyme responsible for transcription of host-cell-mRNAs) such as the "positive-strand leader RNA" believed to bind a host-cell factor and prevent its binding to host-cell promoters (Grinell and Wagner, *J. Virology* 48, 88–101, 1983); and adenovirus proteins E1B-55K and E4-34K which inhibit transport of host-cell transcripts from the nucleus to the cytoplasm (Babiss et al., *Mol. Cell. Biol.* 5, 2552–2558, 1985; Halbert et al., *J. Virology* 56, 250–257, 1985; Pilder et al., *Mol. Cell. Biol.* 6, 470–476, 1986).

The above are all examples of a broader class of macromolecules involved in translation whose concentrations and/ or activities are subject to modulation by viruses. The present invention applies equally well to other macromolecules within thin; broad class. A variety of procedures are available to those skilled in the art which enable them to identify other such macromolecules (including polypeptides, proteins, glycoproteins, lipids, carbohydrates, mucopolysaccharides, glycolipids, and nucleic acids), and to design methods for selecting compounds which can prevent or moderate the interaction between viruses and these macromolecules. In general, the steps required include: ascertaining whether translation is modulated by a given virus during infection; identifying the specific macromolecule(s) mediating the effect on translation; identifying any other cellular and/or viral components involved; characterizing the interaction between these components; and designing a screening method in which disruption or moderation of this interaction can be detected. These steps can be performed in any sequence depending on the nature of the results obtained, and not all steps may be required in order to select compounds which can have the desired effect. The specific details of these steps now follow. Many of the procedures used are collected in such reference texts as Ausubel et al., (eds) *Current Protocols in Molecular Biology*, Wiley-Interscience, New York, 1991, and Sambrook et al., *Molecular Cloning: A Laboratory Manual* (2nd Ed.), Cold Spring Harbor Laboratory Press, Cold Spring Harbor, N.Y., 1989.

Determination that Virus Affects Translation

Several methods can be used to determine whether translation is affected during infection by a particular virus. The overall rate of protein synthesis in infected and uninfected cells can be measured by incubating such cells in the presence of a labeled amino acid and measuring the incorporation of this labeled precursor into protein. The labeled amino acid may typically be one that includes a radioactive isotope, such as $[^{35}S]$methionine, $[^{35}S]$cysteine, $[^{3}H]$leucine, or $[^{14}C]$leucine, and its utilization may typically be followed by measuring the incorporation of radioactivity into trichloroacetic-acid-precipitable protein. As well as the overall rate of protein synthesis, the rates of individual stages of translation, such as initiation and elongation, can be measured using standard procedures such as polysome profiling and transit time determination. As an alternative to incubating intact cells with radiolabeled substrates, extracts can be made from uninfected and infected cells and utilized in in vitro translations with these substrates, examining the translation of endogenous mRNAs or test mRNAs added to the cell extracts.

Additional important information about the effects of viruses on translation can be obtained by examining the types and relative quantities of proteins produced in uninfected and infected cells. This can be achieved by incubating these cells in the presence of radiolabeled amino acids as described above and then using polyacrylamide gel electrophoresis to separate the radiolabeled proteins produced. The separated proteins can be detected by autoradiography or with a Phosphor Imager device, and analyzed by comparison with standard labeled proteins of known molecular weights included on the same polyacrylamide gel during electrophoresis. As in the case of rate determinations, these studies of protein synthesis can also be performed using extracts made from cells rather than intact cells themselves.

Identification of Macromolecules

Once evidence is obtained that translation is affected by infection with the virus under study, the activities and concentrations of all macromolecules known to be involved directly or indirectly in the process of translation or its regulation can be compared in uninfected and infected cells and/or in extracts made from such cells. If the evidence obtained points to an effect on a specific stage of translation such as initiation or elongation, attention might initially be directed be directed to macromolecules known to be involved at that stage.

Macromolecules which may be examined include but are not limited to known translation factors (reviewed and listed in Hershey, *Ann. Rev. Biochem.* 60, 717–755, 1991) such as initiation factors (such as eIF-1, eIF-1A, eIF-2, eIF-2A, eIF-2B, eIF-2C, eIF-3, eIF-3A, eIF-4A, eIF-4B, eIF-4F (p220), eIF-5 and eIF-5A) elongation factors (such as eEF-1a, eEF-1b, eEF-1g and eEF-2), termination factors (such as eRF), ribosomal proteins, kinases and phosphorylases and any other enzymes which act directly or indirectly to modify any of the proteins just listed or any other macromolecules involved in translation, proteases which may degrade any proteins important for translation, ribosomal RNAs (rRNAs), transfer RNAs (tRNAs), enzymes which synthesize or degrade rRNAs and tRNAs, aminoacyl-tRNA synthetases, interferons, and any other macromolecules which induce or repress the synthesis of components or regulators of the translational apparatus.

Methods which can be used to analyze components involved in translation include, but are not limited to, functional assays of enzyme activity, in vitro translations, coupled in vitro transcription-translation reactions, incubations with [gamma-$^{12}$P]ATP to allow determination of phosphorylation status, immunoprecipitation, one-dimensional and two-dimensional gel electrophoresis, Western blotting, differential centrifugation, chromatographic purification, UV-crosslinking, gel retardation assays, other DNA-binding and RNA-binding assays, and the like.

Another approach to identifying a component involved in a viral effect on translation is to make extracts from uninfected and infected cells and fractionate these extracts based on their ability to exhibit an effect on in vitro translation reactions. Thus, extracts from uninfected and infected cells are initially added to parallel but separate in vitro translation reactions, and their effects on these reactions compared. The two types of extract are then be fractionated in parallel using a variety of procedures known to those skilled in the art, and corresponding fractions from the two extracts are tested in parallel for their effects on in vitro translation reactions. Fractions found to contain a translation-affecting component from infected cells are then fractionated further in parallel with the corresponding fractions from uninfected cells, and the new fractions obtained from this next round of fractionation are also tested in in vitro translation reactions. Repeated iterations of this fractionation and testing procedure eventually provides a relatively purified fraction from infected cells which contains the component(s) involved in the observed viral effect on translation.

Fractionation methods which can be used in this approach include, but are not limited to, centrifugation, ammonium sulfate precipitation, other differential precipitations, gel filtration, ion exchange chromatography, hydrophobic interaction chromatography, reverse phase chromatography, affinity chromatography, differential extractions, isoelectric focusing, electrophoresis, isotachophoresis, and the like.

Since translation depends on the availability of mRNA templates, it may also be important to extend the analyses to cover the synthesis, processing, transport and degradation of mRNA. mRNA synthesis (transcription) can be examined in an manner analogous to protein synthesis, by utilizing the incorporation of labeled precursors into mRNA in order to determine overall rates of mRNA synthesis and to generate labeled material that can be examined by gel electrophoresis, in this case on agarose as well as polyacrylamide gels. Processing and transport of mRNA can also be examined using labeled precursors, to analyze the sizes and quantities of various labeled RNA species in nuclear and cytoplasmic extracts of cells. Alternatively, the sizes and quantities of these RNAs can be examined by the Northern blot hybridization procedure, in which RNAs that have been separated by electrophoresis and transferred to a hybridization membrane are detected by hybridization with a labeled nucleic acid probe specific for the RNAs of interest. Degradation of mRNAs can be followed by similar procedures, using radiolabeled mRNAs or Northern blot hybridizations to trace the fate of mRNAs. For all stages of mRNA synthesis, processing, and degradation it may also be useful to measure the activities and concentrations of the enzymes and other proteins involved, such as RNA polymerases, splicing enzymes, splice-junction binding proteins, and ribonucleases responsible for degrading mRNAs. Alterations in transcriptional activity may also be detected and analyzed utilizing cell extracts for in vitro transcription reactions.

Identification of Other Components Involved

Detailed investigation of viral effects on translation may often reveal one or more cellular components whose activity or concentration is modulated during viral infection. It might, for example, identify an initiation factor or elongation factor or subunit thereof which is degraded in infected cells, or which becomes phosphorylated, dephosphorylated or otherwise modified in a way that alters its activity. Once one such effect has been observed, it points the way for further investigations to identify additional cellular and/or viral components involved.

Thus, if a component of the translational apparatus has been found to be degraded, attention may turn to identifying the enzyme responsible for this degradation. This is achieved by measuring the activities of enzymes known to act upon the degraded component, or by fractionating extracts from infected and uninfected cells and measuring the component-degrading activity of each fraction. Repeated rounds of fractionation by a variety of procedures known to those skilled in the art can be used to isolate the degrading activity. Fractionation procedures which may be used include, but are not limited to, centrifugation, ammonium sulfate precipitation, other differential precipitations, gel filtration, ion exchange chromatography, hydrophobic interaction chromatography, reverse phase chromatography, affinity chromatography, differential extractions, isoelectric focusing, electrophoresis, isotachophoresis, and the like.

A similar approach can be adopted if the observation is made that a component of the translational apparatus undergoes phosphorylation, dephosphorylation or other modification during viral infection. Thus, measurements may be made of the activities of enzymes known to perform such modifications on the component in question, or extracts from uninfected and infected cells may be fractionated to isolate the enzyme(s) responsible, testing each fraction for its ability to modify the component in the manner originally observed.

Inhibitors of a given translational step or component may likewise be identified by fractionating extracts from uninfected and infected cells and testing each fraction for its ability to inhibit the step or component in question.

Translation-affecting components isolated by any of the aforementioned fractionation approaches can be utilized to help clone the gene(s) which code for these components. If, for example, the component isolated is a protein, its amino acid sequence or a part of that sequence can be determined by well known protein sequencing methods, and the sequence information obtained can be used to predict the sequence of oligonucleotides which can be used as reverse transcriptase primers for cDNA synthesis or as amplification primers for the polymerase chain reaction, or as hybridization probes for screening gene/cDNA libraries. Alternatively, the isolated component can be used as an immunogen to raise antibodies against the component, which antibodies can then be used to screen cDNA expression libraries to identify clones encoding the component. Antibodies can also be raised by synthesizing a short peptide corresponding to part or all of any amino acid sequence determined from the isolated component, and using this peptide as immunogen. The peptide-induced antibodies can be used to screen cDNA expression libraries, or to affinity-purify the component in larger quantities enabling more extensive sequence determination, and thus providing more extensive information on which to base a cloning strategy.

The identification of viral components responsible for effects on translation may be facilitated by examining mutant viruses, either naturally occurring mutants or mutants made in the laboratory. The latter may be constructed by a variety of procedures known to those skilled in the art, including but not limited to, chemical treatment with mutagens, and the use of molecular biology techniques to generate insertions, substitutions, deletions and point mutations in viral genes or the viral genome. The impact of various mutations on the interactions between the virus and host-cell translation can then be assessed. If particular mutations alter or abolish the effect(s) which a virus has on translation, this provides strong evidence that the gene or genes in which the mutations occur are important in mediating these effects.

Further evidence for the involvement of these genes and their products can be obtained in a variety of ways. One route is to use recombinant DNA techniques to produce the product(s) of the viral gene(s) implicated by the mutational analysis, and then to test the effects of these gene products on translation. The testing can be performed, for example, by adding the viral gene products to in vitro translation reactions or by expressing these gene products in intact cells.

Even without mutational analysis, in vitro transcription and translation procedures can be used to determine whether the addition of viral genomes or RNAs or subsets or fragments thereof, or the translation products of such molecules, has an impact on translation. Such genomes or RNAs or subsets or fragments can be obtained in a variety of ways, for example, by purification from virus particles, extraction from infected cells, cleavage of intact viral RNAs or DNAs using ribonucleases or deoxyribonucleases, oligodeoxynucleotide-directed cleavage of viral RNAs by ribonuclease H, cleavage of viral DNAs by restriction endonucleases, amplification of specific segments of viral RNA or DNA by the polymerase chain reaction, transcription from cloned viral genes or cDNAs, and so on.

Viral components involved in effects on translation can also be identified by introducing individual viral components or genes/cDNAs which encode them or fragments of components or genes/cDNAs into intact cells rather than in vitro translation reactions. The translational status in cells into which such an introduction had been made can then be compared with the status within cells which had received a "mock introduction" or none at all. A change in translational status would implicate the viral component or gene/cDNA or fragment thereof which had been introduced into the cell.

Another approach to identifying cellular and viral components involved in translational effects is to use labeled nucleic acids prepared from uninfected and infected cells as probes in differential hybridization screens of gene/cDNA "libraries" made from viral or cellular nucleic acids. Such libraries are often made in the Lambda gt10 vector or similar vectors. Clones which behave differently towards the labeled nucleic acid probes from infected and uninfected cells will be investigated further, since they represent sequences whose hybridization partners are either more abundant or less abundant in infected cells than in uninfected cells.

In a modification of this approach, labeled proteins rather than nucleic acids can be prepared from uninfected and infected cells, and the differential screening can be performed under conditions which favor protein-nucleic acid interactions. In this case, clones which behave differently towards the labeled protein probes represent sequences which are partners for nucleic acid-binding proteins that are either more abundant or less abundant in infected cells than in uninfected cells.

A similar approach can be adopted utilizing expression libraries made from viral or cellular nucleic acids, that is, libraries made in such a way that the protein encoded by each cloned gene is expressed within the clone that contains it. Such libraries are often made in the Lambda gt11 vector or similar vectors. In this case, differential screening with labeled nucleic acids from uninfected and infected cells will reveal clones encoding proteins that interact with nucleic acids which are either more abundant or less abundant in infected cells than in uninfected cells. Differential screening with labeled proteins on the other hand will reveal clones encoding proteins that interact with other proteins which are either more abundant or less abundant in infected cells than in uninfected cells.

Proteins involved in important interactions with other proteins can also be identified using a yeast genetic system known as the two-hybrid system (Fields & Song, *Nature*, 340, 245–246, 1989; Chien et al., *Proc. Natl. Acad. Sci. USA* 88, 9578–9582, 1991). This requires the availability of a gene or cDNA encoding one of the two proteins which interact with each other. In the present case this gene or cDNA can be obtained by any of the several methods described in the preceding text. This gene or cDNA is cloned into a specific plasmid in such a way that it is expressed fused to the DNA-binding domain of a yeast transcriptional activator such as GAL4 which has two separable and functionally essential domains, one for DNA-binding and the other for transcriptional activation. In parallel, genes or cDNAs encoding putative binding partners of the known component are cloned in such a way that each putative partner is expressed fused to the transcriptional activation domain of the same DNA-binding protein. Introduction of both types of fusion into the same yeast cell results in generation of functional DNA-binding protein only if the fusion partners of the two domains of this protein interact with one another closely enough to bring together its two separately-expressed domains. Clones which produce such functional DNA-binding protein can be selected very easily by plating them on a medium which requires the yeast to produce an enzyme that is under the control of the DNA-binding protein. The gene or cDNA for the partner which binds to the previously identified component can then be recovered from yeast clones which grow on the selective medium.

Many other methods are available for further investigation of an initial observation that some component involved in translation is modulated in infected cells. Other options include but are not limited to: using the component in question as an affinity ligand to identify viral and cellular products which bind to it; labeling this component with a detectable label and using it as a probe to detect viral and cellular products on blots of electrophoresis gels; labeling the component and using it to probe libraries of viral and cellular genes and/or cDNAs; labeling the component and using it to probe cDNA expression libraries to find clones synthesizing proteins which can bind to the component; performing UV-crosslinking studies to identify viral or cellular products which can bind to the component; using the component in gel retardation assays which would detect its ability to bind to viral or cellular nucleic acids; performing footprinting analyses to identify the regions within a nucleic acid to which the component binds; and so on.

From this description it should be evident that a wide variety of methods is available to someone skilled in the art to identify viral and cellular components which interact with a component that has been found to be modulated in viral-infected cells.

Interactions Between Components

Many different methods are available to characterize the interactions between cellular and viral components which affect translation. The susceptibility of such an interaction to changes in pH, ionic strength, temperature, the nature and mixture of anions and cations present, the relative concentrations of the two components, the absolute concentrations of these components, the availability of cofactors, the availability of an energy source, the presence or absence of lipids, of nucleic acids, of carbohydrates, of other proteins, and/or of any other additives can all provide information about the nature of the interaction between the components. So too can the susceptibility of the interaction to treatment of one or both components with alkylating agents, oxidizing agents, reducing agents, or other agents which cause chemical modifications, or with enzymes that phosphorylate, dephosphorylate, glycosylate, deglycosylate, add lipid side-chains, remove lipid side-chains, or cause other enzymatic modifications, be measured.

Also informative are the effects of truncations, additions, substitutions, deletions, inversions and point mutations in one or both components. Such structurally altered components can be generated by treatment of intact components with cleavage enzymes such as proteases, endoribonucleases and endodeoxyribonucleases, with editing enzymes such as DNA polymerases, with joining enzymes such as RNA ligases, DNA ligases, and RNA splicing enzymes, with copying enzymes such as DNA polymerases, RNA polymerases, and reverse transcriptases, with end-specific degrading enzymes such as 5'-exonucleases, 3'-exonucleases, aminopeptidases and carboxypeptidases, with enzymes that can add extensions to ends such as terminal deoxynucleotidyl transferase and poly(A) polymerase, and so on. Alternatively, structurally altered components can be generated by making appropriate alterations to cloned genes and expressing these genes in intact cells or in in vitro systems. Thus, the use of restriction enzymes, ligases, linkers, adaptors, reverse transcriptases, DNA polymerases, RNA polymerases, polymerase chain reactions, site-directed mutagenesis, and randomized mutagenesis make it possible to generate an enormous spectrum of structurally altered forms of components which interact with one another. These structural alterations can then be tested in the array of methods previously described to determine whether the alterations change or abolish the interaction between different components and/or the impact of these components on translation.

Methods to Screen Potential Agents

Methods to screen potential agents for their ability to disrupt or moderate viral effects on translation can be designed without detailed knowledge of the precise interaction between viral and cellular components, although such a knowledge can certainly be helpful. In principle, many of the numerous methods which have so far been described to identify viral and cellular components involved in effects on translation can be readily adapted to detect interference with the interaction between these components. Thus, for example, if it has been found that viral infection leads to the phosphorylation, dephosphorylation or other modification of a given component, or to a change in its catalytic activity such as the inhibition of that activity, or to enhanced synthesis or degradation of this component, or to any other observable effect described in the foregoing disclosure, then agents can be screened for their ability to prevent or moderate this effect on the component in question. The screening can be performed by adding the test agent to intact cells which have been infected by virus and then examining the component of interest by whatever procedure has been established to demonstrate the viral effect on this component. Alternatively, the screening can be performed by adding the test agent to in vitro translation reactions and then proceeding with the established analysis. As another alternative; purified or partially purified components which have been determined to interact with one another by the methods described above can be placed under conditions in which the interaction between them would normally occur, with and without the addition of the test agent, and the procedures previously established to analyze the interaction can be used to assess the impact of the test agent. In this approach, the purified or partially purified components may be prepared by fractionation of extracts from uninfected and infected cells, or they may be obtained by expression of cloned genes or cDNAs or fragments thereof, optionally followed by purification of the expressed material.

Within the broad category of in vitro selection methods, several types of method are likely to be particularly convenient and/or useful for screening test agents. These include but are not limited to methods which measure a binding interaction between two or more components, methods which measure the activity of an enzyme which is one of the interacting components, and methods which measure the activity or expression of "reporter" protein, that is, an enzyme or other detectable or selectable protein, which has been placed under the control of one of the components.

Binding interactions between two or more components can be measured in a variety of ways. One approach is to label one of the components with an easily detectable label, place it together with the other component(s) in conditions under which they would normally interact, perform a separation step which separates bound labeled component from unbound labeled component, and then measure the amount of bound component. The effect of a test agent included in the binding reaction can be determined by comparing the amount of labeled component which binds in the presence of this agent to the amount which binds in its absence.

The separation step in this type of procedure can be accomplished in various ways. In one approach, (one of) the binding partner(s) for the labeled component can be immobilized on a solid phase prior to the binding reaction, and unbound labeled component can be removed after the binding reaction by washing the solid phase. Attachment of the binding partner to the solid phase can be accomplished in various ways known to those skilled in the art, including but not limited to chemical cross-linking, non-specific adhesion to a plastic surface, interaction with an antibody attached to the solid phase, interaction between a ligand attached to the binding partner (such as biotin) and a ligand-binding protein (such as avidin or streptavidin) attached to the solid phase, and so on.

Alternatively, the separation step can be accomplished after the labeled component had been allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner, a ligand-binding protein which can interact with a ligand previously attached to the binding partner, and so on.

Test methods which rely on measurements of enzyme activity are performed in accordance with the characteristics of the enzyme in each case. As noted above, a variety of enzyme activities can be determined to be involved in the translational effect of a virus, including but not limited to kinases, phosphatases, glycosylases, deglycosylases, transferases, lipases, deoxyribonucleases, ribonucleases, proteases, synthetases, polymerases, and the like, as well as those other enzyme activities noted above. In general, measurements of enzyme activity require the ability to measure the product of the reaction in the presence of other materials, and often to distinguish or separate the product of the reaction from the substrate for the reaction. Methods which may be used to measure reaction products include but are not limited to measurement of the transfer or incorporation of a radioactive or other labeled atom or group, spectrophotometric or colorimetric measurement of the concentration of the product, measurement of light output from a luminescent or chemiluminescent reaction, measurement of fluorescence from a fluorescent product, immunoassays, other immunochemical procedures, and other competitive binding assays. Enzyme activity can also be measured using any of the procedures just mentioned to detect the product of a secondary reaction or reactions which rely on the product of the reaction of interest as a substrate or a cofactor.

In many cases the product of an enzyme reaction can be detected without separating that product from other constituents of the reaction mixture, as for example when an uncolored chromogenic substrate gives rise to a colored product or the absorption spectrum for the product is different from that of the substrate, allowing selection of a wavelength for absorbance measurements of just the product. Immunoassays, other immunochemical procedures and other competitive binding assays can also often be performed without first separating the product of interest.

In other cases it may be necessary to include a separation step or steps to separate the product from other constituents of the reaction mixture before measuring it. In such cases, the necessary separation can be accomplished by a variety of procedures, including but not limited to centrifugation, trichloroacetic acid precipitation, ethanol precipitation, ammonium sulfate precipitation, other differential precipitations, gel filtration, ion exchange chromatography, hydrophobic interaction chromatography, reverse phase chromatography, affinity chromatography, differential extractions, isoelectric focusing, electrophoresis, isotachophoresis, and the like.

In addition to methods which measure the activity of an enzyme implicated in a viral effect on translation, test methods may also be employed which have been configured such that the component(s) implicated in the viral effect controls the activity or expression of a "reporter" protein, that is, an enzyme or other detectable or selectable protein. In the case, for example, where a kinase has been implicated in the viral effect, the test method might be configured in such a way that phosphorylation of a particular protein by the kinase leads to the activation or inhibition of that protein or of some other protein controlled by that protein. In yeast, for example, phosphorylation of eIF2-α by the GCN2 protein (or by mammalian p68 kinase substituting for GCN2) leads to an inhibition of the initiation of translation, which in turn leads to an increase in the synthesis of the GCN4 protein, which in turn induces the synthesis of further proteins involved in amino acid biosynthesis. "Reporter" proteins can be readily fused to the GCN4 protein at the genetic level so that the synthesis of these reporters is effectively induced by the initial phosphorylation event catalyzed by GCN2 or mammalian p68.

Similar approaches can be used to detect modulation by test agents of the activity of a variety of other components which might be implicated in viral effects on translation. The effect of a test agent on a protease, for example, can be monitored by following the survival in an in vitro reaction of a reporter protein which is a target for that protease. Similarly, the effect of a test agent on a nuclease can be monitored by following the appearance in an in vitro translation reaction or in vitro transcription-translation reaction of a reporter protein translated from a suitably configured coding sequence provided to the reaction.

Proteins suitable for use as reporters in such assays include, but are not limited to, easily assayed enzymes such as β-galactosidase, luciferase, β-glucuronidase, chloramphenicol acetyl transferase, and secreted embryonic alkaline phosphatase; proteins for which immunoassays are readily available such as hormones and cytokines; proteins which confer a selective growth advantage on cells such as adenosine deaminase, aminoglycoside phosphotransferase (the product of the neo gene), dihydrofolate reductase, hygromycin-B-phosphotransferase, thymidine kinase (when used with HAT medium), xanthine-guanine phosphoribosyltransferase (XGPRT), and proteins which provide a biosynthetic capability missing from an auxotroph; proteins which confer a growth disadvantage on cells, for example enzymes that convert non-toxic substrates to toxic products such as thymidine kinase (when used with medium containing bromodeoxyuridine) and orotidine-5'-phosphate decarboxylase (when used with 5-fluoroorotic acid); and proteins which are toxic such as ricin, cholera toxin or diphtheria toxin.

Many of the methods so far described for selecting test agents have involved examining the impact of these agents on the interaction between two or more components in in vitro reactions. The interacting components can also be brought into contact with one another within cells rather than in in vitro reactions. In this approach, coding sequence (s) encoding part or all of a component or components would be introduced into a selected type of cell. Coding sequences for this approach include cloned genes or cDNAs or fragments of either or fragments amplified by the polymerase chain reaction or natural RNAs or transcribed RNAs or the like. Several variations of the approach are possible. In one variation, a coding sequence is introduced for a first component into a cell known to contain components with which this first component will interact. Thus, for example, a coding sequence for a viral component is introduced into a cell which is a normal target for infection by the virus in question. Agents are tested to select those which block the effect of the viral component within the cell into which the coding sequence has been introduced. In another variation, coding sequences for two or more components which interact with one another might be introduced into a cell, and agents tested for their ability to moderate the interaction between these components, this interaction being followed by the procedures previously established as suitable for the purpose. The cell into which the coding sequences are introduced can be one which would normally be a target for infection by the virus in question. Alternatively and usefully, the cell can be one which is easier to grow, manipulate and test such as a yeast cell. Indeed, there are distinct advantages to reconstructing a translation control mechanism in heterologous cells, in which the interactions between the components involved are easier to study than they are when those components are in their normal environment. In the case of yeast, in particular, the powerful genetic approaches available often make it possible to identify and isolate the yeast homologues of genes from higher eukaryotes more quickly than the corresponding genes can be identified in the higher eukaryotes.

From the foregoing it should be apparent that one skilled in the art is able to choose from a wide variety of methods at each stage in the identification of components involved in viral effects on translation, in the characterization of the interaction between these components, and in the implementation of screening tests to select compounds which moderate or abolish the interaction between these components.

Protein Kinase

The following is a more detailed outline of the specific screening and related protocols useful in this invention. This section describes a method for screening agents effective to inhibit viral replication in a host eukaryotic cell. As one detailed example, the system chosen is one in which the virus is able to produce a viral inhibitor which interferes with the activity of the host-cell interferon-induced, double-stranded RNA-activated protein kinase. As noted above, however, this example is not limiting in the invention and only exemplifies the broad scope of the invention.

The method generally includes the steps of incubating the protein kinase, the viral inhibitor, and the compound to be tested, under conditions effective to cause viral inhibitor interference with the activation of the protein kinase, and examining the mixture for interference. The invention contemplates four general embodiments, as detailed below.

The particular screening protocol will depend to some extent on the site of action of the virus inhibitor. For example, various viruses degrade the kinase (e.g., polio), others inhibit activation of the kinase (Adenovirus VA1 RNA, Epstein-Barr virus EBER-1, HIV-1 TAR RNA, and Influenza), yet others bind dsRNA (Reovirus sigma 3 and vaccinia SKIF (E3L)), and others inhibit activity of the kinase (Influenza, SV40 Tag, and Vaccinia K3L). These various mechanisms can be attacked by different inhibitory agents of this invention which can be identified by methods described below.

A. In vitro Screening for Compounds

In one example, the method is used for screening a compound effective to inhibit replication in a host cell of a virus which produces a viral inhibitor able to bind to the p68 protein kinase and block its activation by double-stranded RNA (dsRNA). Here, the incubating step includes incubating the mixture under conditions effective to bind the viral inhibitor to the protein kinase, and the examining step includes examining the protein kinase for bound viral inhibitor.

The incubating may be carried out, for example, in solution phase, and the examining step includes passing the mixture through a filter which retains the viral inhibitor only when the inhibitor is bound to the protein kinase.

Alternatively, the protein kinase may be bound to a solid support, the viral inhibitor labeled with a reporter, and the examining step performed by measuring the amount of reporter bound to the solid support.

Alternatively, the incubating may be carried out under conditions in which the protein kinase is autophosphorylated, in the absence of binding to the viral inhibitor, and the examining step performed by determining the extent of phosphorylation of the p68 kinase.

In a second example, the incubating step includes incubating the mixture under conditions effective for the p68 kinase to be activated in the absence of the viral inhibitor, and the examining step includes examining the activity of the p68 kinase in the presence of the inhibitor.

The incubating may be carried out, for example, using a purified or partially purified p68 kinase preparation, and the examining step includes measuring autophosphorylation of the kinase or phosphorylation of eIF2-alpha or histone substrates provided to the kinase.

Alternatively, the incubating may be carried out in an in vitro translation mixture containing the p68 kinase, and the examining step includes measuring the amount of a reporter polypeptide produced by translation of specific mRNA. The mRNA may be one whose translation is reduced by activation of p68 kinase, or preferably, one whose translation is increased, such as a chimeric RNA whose 5'-untranslated leader is derived from the yeast GCN4 gene.

In a third example, the method is used for screening compounds effective in blocking viral replication of a virus which produces a viral inhibitor effective to activate a host-cell component which is able in activated form to block activation of the protein kinase or inhibit the activated kinase. Here the mixture formed includes the host-cell component (in activated form), the incubating step is carried out under conditions in which the protein kinase is activated, in the absence of the activated component, and the examining step includes examining the mixture for inhibition of protein kinase activity. Alternatively, the mixture formed includes the host-cell component in non-activated form and the viral inhibitor which activates the host-cell component, the incubating step is carried out under conditions in which the protein kinase is activated, in the absence of the viral inhibitor and activated host-cell component, and the examining step includes examining the mixture for inhibition of protein kinase activity B. In vivo Screening In a fourth example, the viral or virus-activated inhibitor is expressed in a yeast cell which is constructed to increase the expression of a reporter polypeptide in the presence of activated p68 kinase, and the examining step includes examining the yeast cells for increased expression of the reporter polypeptide.

One of the yeast proteins which participates in translation control is the protein GCN2. The protein is a kinase which is activated by binding of uncharged tRNAs, which accumulate when amino acids are in short supply. The activated protein inhibits translation levels in yeast, by phosphorylating the alpha subunit of the initiation factor eIF2. Another result of GCN2 activation is increased production of a yeast GCN4 protein, which then activates anabolic pathways for the synthesis of amino acids.

A construct used in the present invention for in vivo screening is a yeast cell in which the GCN2 gene is replaced with a mammalian p68 gene under the control of a regulated promoter. The cell also includes the additional modifications described below. Introduction of the p68 gene into yeast can be carried out using standard recombinant techniques for introducing a selected coding sequence into yeast. Briefly, the p68 gene is placed under the control of a down-regulatable promoter, with cell selection occurring under down-regulated conditions. This is done because in yeast cells the p68 protein is constitutively activated, presumably by endogenous dsRNA, and if expressed at too high a level it inhibits cell translation in its activated condition.

The yeast cells are then further constructed to enable the regulation of p68 to be tested by examining the levels of a reporter polypeptide whose production is dependent on the presence of activated p68 enzyme. Such a reporter can be produced from a β-gal gene fused to the GCN4 yeast gene. The latter gene becomes expressed under conditions of GCN2 activation, and has been shown to be under the control of the p68 phosphorylation system in yeast cells in which GCN2 has been replaced with p68. Thus, the presence of activated p68 leads to a shutdown of yeast translation in general, but to enhanced production of the fused GCN4/β-gal protein. The expression of the fused protein can be measured easily by measuring β-gal activity.

The screening system is designed for screening drugs which are effective to disrupt a viral pathogen's counter-defense against the host cell's attempt to shut down cell translation, by activation of the p68 protein. The viral counter-defense may include, among others, (a) a VA1, EBER-1, or TAR viral inhibitor RNA which occupies the binding site on p68 and prevents dsRNA from binding to and activating p68, or (b) the ability of the virus, e.g., influenza virus, to induce or activate a cellular component which is effective to prevent activation of p68 or deactivate the activated enzyme, or (c) a viral protein such as reovirus σ3 protein or vaccinia virus K3L and E3L proteins which blocks the activation or activity of p68, or (d) a complex of a cellular component with a viral RNA, such as the complex used by poliovirus to degrade the p68 kinase.

In the case of a viral inhibitor, the yeast cells used in screening are further constructed to contain the gene for the viral inhibitor under the control of an inducible promoter. Under non-inducing growth conditions, in which the viral inhibitor is not expressed (but p68 protein is), the p68 protein is activated, presumably by endogenous dsRNA as noted above, and the presence of activated p68 is manifested by relatively high measured levels of the GCN4/β-gal fusion protein. Under inducing growth conditions, for example, when the growth medium includes the inducer for the inducible promoter which controls the expression of the viral inhibitor, the cells show low levels of activated p68 due to the presence of the viral inhibitor, and this is manifested by relatively low levels of the GCN4/β-gal fusion protein. Potential antiviral agents are tested by assessing their impact on the measured levels of the GCN4/β-gal fusion protein under inducing conditions for the viral inhibitor. Those agents which allow relatively high levels of fusion protein to be synthesized are selected, as being agents which prevent the viral inhibitor from interfering in activation of p68 by endogenous double-stranded RNA.

In the case of a cellular component induced or activated by a virus to prevent activation of p68 kinase or inhibit activated kinase, the gene for this cellular component is placed in the yeast cells used for screening under the control of an inducible promoter (in place of the viral inhibitor RNA gene described above). The yeast strain is then used for screening essentially as described for viral inhibitors. Thus, under non-inducing growth conditions, the cellular component is not expressed, and relatively high levels of the GCN4/β-gal fusion protein are observed, reflecting the presence of p68 activated by endogenous double-stranded RNA. Under inducing growth conditions, the levels of the GCN4/β-gal fusion protein are lower, reflecting inhibition of the activation or activity of p68 by the cellular component. Potential antiviral agents are tested by assessing their impact on the measured levels of the GCN4/β-gal fusion protein under inducing conditions for the cellular component, and agents selected which allow relatively high levels of fusion protein to be synthesized.

A similar approach is adopted in the case of a complex between a cellular component and a viral component which degrade the p68 kinase. In this case, the yeast strain would be further constructed to contain genes for both the cellular and the viral component under inducible control, and the screening would be performed essentially as described above.

The following examples illustrate the screening methods described above, but in no way are intended to limit the scope of the invention.

EXAMPLE 1

Preparing p68 Protein Kinase

A. From Interferon-Induced Human Cells p68 protein kinase is prepared from interferon-induced human tissue culture cell lines. Cells are lysed by Dounce homogenization, and nuclei and cell debris removed by centrifugation at 30,000×g for 20 minutes. 4 M KCl is added to the supernatant to a final concentration of 100 mM, and ribosomes are pelleted by centrifugation at 60,000 rpm in Beckman type 60 rotor. The ribosomal pellet is resuspended in 800 mM KCl, 20 mM HEPES (pH 7.4), 1.5 mM $MgCl_2$, 0.1 mM EDTA, 1 mM DTT and 1 µM phenylmethylsulfonyl fluoride (PMSF), then homogenized using a Dounce homogenizer. The ribosomes are then centrifuged again at 60,000 rpm for 90 min at 4° C. in a type 60 rotor. The resulting supernatant is dialyzed against 50 mM KCl, 20 mM HEPES (pH 7.4), 1.5 mM $MgCl_2$, 0.1 mM EDTA, 1 mM DTT, 10% glycerol and 1 µM PMSF. The dialysate is centrifuged again to remove solids. The resulting supernatant (ribosomal salt wash) is applied to a DEAE-cellulose column equilibrated in 50 mM KCl, 20 mM HEPES (pH 7.4), 1.5 mM $MgCl_2$, 0.1 mM EDTA, 1 mM DTT, 10% glycerol and 1 µM PMSF. p68 kinase is collected in the flow through fraction, adjusted to pH 6.8, and applied to a S-Sepharose Fast Flow (Pharmacia) column equilibrated with 50 mM KCl, 20 mM HEPES (pH 6.8), 1.5 mM $MgCl_2$, 0.1 mM EDTA, 1 mM DTT, 10% glycerol and 1 µM PMSF. p68 kinase is eluted from the column in a linear gradient of 50–500 mM KCl in 20 mM HEPES (pH 7.4), 1.5 mM $MgCl_2$, 0.1 mM EDTA, 1 mM DTT, 10% glycerol and 1 µM PMSF. The p68 kinase peak is loaded onto a hydroxyapatite HPHT (BioRad) column equilibrated in 50 mM KCl, 20 mM HEPES (pH 7.2), 50 mM potassium phosphate (pH 7.2), 1.5 mM $MgCl_2$, 0.1 mM EDTA, 1 mM DTT, 10% glycerol and 1 µM PMSF. p68 kinase is eluted in a linear gradient of 50–500 mM potassium phosphate (pH 7.2). The p68 peak is loaded to an HR 5/10 Mono S column (Pharmacia) and eluted in a linear gradient of 50–500 mM KCl in 20 mM HEPES (pH 7.4), 1.5 mM $MgCl_2$, 0.1 mM EDTA, 1 mM DTT, 10% glycerol and 1 µM PMSF. The purified p68 is stored at −70 C.

B. From Recombinant *E. coli* Cells

Alternatively, p68 is purified from *E. coli* expressing human p68 kinase, according to published methods (Barber et al., 1991, *Biochemistry* 30:10356). Briefly, *E. coli* strain BL21 (DE3) pLysS is transformed with a plasmid containing the coding sequence for wild-type p68 protein kinase under the control of an inducible promoter. The resulting *E. coli* strain is grown to log phase, then induced to express p68 kinase. Cells are harvested by centrifugation, and lysed by lysozyme. p68 kinase is purified from the lysate by affinity chromatography using a monoclonal antibody to p68 kinase coupled to Sepharose, according to published methods (Galabru et al., 1989, *Eur. J. Biochem.* 178:581).

EXAMPLE 2

Preparation of Viral Inhibitors

A. VAI RNA

VAI RNA is prepared according to published methods (Mellits et al., 1990, *Nucl. Acids Res.* 18, 5401). Briefly, plasmid pT7VA/Ad2I, abbreviated here to pT7VA, is a derivative of the cloning vector pUC119 containing the promoter for T7 RNA polymerase fused upstream of the gene for Ad2 $VA\ RNA_2$. The plasmid is linearized by digestion with Dra I to allow preparation of run-off transcripts which are exact copies of VA1 RNA. Transcription is performed in reactions containing 37.5 µg/ml T7 RNA polymerase, 50 µg/ml linearized pT7VA DNA, 40 mM Tris-HCl, pH 7.8, 14 mM $MgCl_2$, 2 mM spermidine, 5 mM dithiothreitol (DTT), 4 mM each. rNTP, and 1 unit/µl RNasin (Promega). After incubation at 40° C. for 90 minutes, the reaction is terminated by addition of EDTA to 20 mM, extracted with phenol and then chloroform, and the RNA is precipitated with ethanol. VA1 RNA is purified by denaturing the redissolved precipitate, running it on an 8% polyacrylamide/7 M urea sequencing gel, excising the major band, and recovering the RNA by standard methods. Labeled VA1 RNA is prepared by performing transcription as described but including either [alpha-$^{32}$P]UTP or biotinylated-UTP.

B. EBER-1 RNA

The EBER-1 RNA is prepared according to published methods (Clarke et al., 1990) from the plasmid pPAC-1, which contains the T7 RNA polymerase promoter sequence upstream of the EBER-1 gene. For transcription of the EBER-1 RNA, plasmid pPAC-1 is linearized with Sau3A I and used as the template in an in vitro transcription reaction with T7 RNA polymerase under the conditions recommended by the supplier. Following transcription, the RNA is extracted once with phenol/chloroform and once with chloroform, precipitated with ethanol and examined by electrophoresis on a non-denaturing agarose gel, to confirm the presence of the predicted 171-nucleotide species. The EBER-1 preparations are further purified by chromatography on CF11-cellulose (Whatman), to removed double-stranded RNA. Labeled EBER-1 RNA is prepared by performing transcription as described but including either [alpha-$^{32}$P3UTP or biotinylated-UTP

C. HIV TAR RNA

HIV TAR RNA is isolated by published methods (Gunnery et al., 1990, *Proc. Natl. Acad. Sci. US* 87, 8687), using plasmid pEM-7, which contains the T7 RNA polymerase promoter bacteriophage T7 upstream of a sequence corresponding to nucleotides +3 to +82 of the HIV LTR. The plasmid is linearized by digestion with Hind III and used as a template for transcription of TAR RNA which is then purified essentially as described in part B above. Labeled TAR RNA is prepared by performing transcription as described but including either (alpha-$^{32}$P]UTP or biotinylated-UTP.

EXAMPLE 3

Screening Method: Solid Phase Support for Immobilized p68 Kinase 100 ng–5 µg of a monoclonal antibody to human p68 kinase is immobilized in each well of a microtiter plate or on nitrocellulose in each slot of a slot-blot apparatus. After incubation for 1 hour at room temperature to allow antibody to bind, the plate or slot-blot is washed 2–4 times with phosphate buffered saline to reduce non-specific binding. p68 kinase is then bound to the immobilized antibody as follows. 10–50 µl of a cell extract containing p68 is added to each well or slot. The p68-containing extract is either a 1:20 dilution of a cell lysate from interferon-treated eukaryotic cells or from *E. coli* cells expressing human p68 kinase, or a partially purified preparation of p68 kinase from either source. After incubation for 1 hour at room temperature to allow p68 to bind, the plate or slot-blot is washed 2–4 times with phosphate buffered saline to reduce non-specific binding. If a slot-blot apparatus is being used, the nitrocellulose sheet is now removed. Binding reactions are performed by adding labeled VAI RNA or other viral inhibitor to each well or to the entire nitrocellulose sheet after its removal from the slot blot apparatus. VAI RNA is added at a concentration of about 2–3 ng/ml in phosphate buffered saline. The plate or nitrocellulose sheet is incubated for 1 hour at room temperature, and washed 2–4 times with phosphate buffered saline to reduce non-specific binding. Bound VAI RNA (or other inhibitor) is quantitated by autoradiography or liquid scintillation counting for $^{32}$P-labeled VAI RNA, or using streptavidin, biotinylated alkaline phosphatase and chemi-luminescent detection for biotinylated VAI RNA. A typical test series includes the following reactions: a) a control reaction with inhibitor but no p68 kinase; b) control reactions with test compound alone or with either p68 kinase or inhibitor; c) a reaction including p68 kinase and inhibitor without test compound; and (d) a reaction including p68 kinase, inhibitor and test compound. For test compounds which interfere with binding of viral inhibitor to p68 kinase, the amount of bound inhibitor detected in reaction (d) is less than that detected in reaction (c).

EXAMPLE 4

Slot-Blot Filter-Binding Assay

Reaction mixtures containing one or more of purified radiolabeled VAI RNA (or other viral inhibitor), purified p68 kinase, and test compound are incubated together for 15–20 minutes on ice in the presence of 75 mM KCl, 25 mM HEPES, (pH 7.4). 10 mM MgCl$_2$, 1.0 mM dithiothreitol, 0.1 mM ATP, 0.1 mg/ml bovine serum albumin, 0.1 mM tRNA and 0.1 mM EDTA. Reactions are diluted with 10 volumes of wash buffer (50 mM KCl, 1.5 mM MgCl$_2$, 20 mM HEPES (pH 7.4), 0.1 mM EDTA), and immediately filtered in a slot-blot apparatus through a 0.45 micron pore-size nitrocellulose membrane (Schleicher & Schuell, Keene, N H) that has been soaked for 1 hour at room temperature in wash buffer containing 0.1 mg each of BSA and salmon sperm DNA per ml. Each well is washed with 200 µl of ice-cold wash buffer, and the filter is dried and exposed to autoradiography. Quantitation is performed by scintillation counting of individual bands or by direct scanning of the membrane with a AMBIS Imaging System. A typical test series includes the following reactions: a) control reactions with p68 kinase alone or VAI RNA alone; b) control reactions with test compound alone or with either p68 kinase or VAI RNA; c) p68 kinase and VAI RNA; and d) p68 kinase, VAI RNA and test compound. For test compounds which interfere with binding of viral inhibitor to p68 kinase, the amount of bound inhibitor detected in reaction (d) is less than that detected in reaction (c).

EXAMPLE 5

Screening Method: p68 Autophosphorylation Assay

In this assay, p68 kinase is incubated under kinase reaction conditions with activating double-stranded RNA, gamma-$^{32}$P ATP to follow kinase autophosphorylation, VAI RNA (or other inhibitor), and a test compound. Up to 2 µl of p68 kinase fraction (the exact volume used depends on the degree of purification) is diluted to 10 µl with 50 mM KCl, 20 mM HEPES (pH 7.4), 1.5 mM MgCl$_2$, 0.1 mM EDTA, 1 mM DTT, 10% glycerol and 1 µM PMSF, 0.1 mg bovine serum albumin and 0.1 mg of tRNA per ml. The diluted kinase is added to 20-µl reaction mixtures containing, at final concentrations, 75 mM KCl, 25 mM HEPES, (pH 7.4), 10 mM MgCl$_2$, 1.0 mM dithiothreitol, 0.1 mM EDTA, 0.1 mM ATP, protease inhibitors, and 5 to 10 µCi of [gamma $^{32}$P] ATP (>3,000 Ci/mmol; Dupont, NEN). Reaction mixtures are supplemented as appropriate with reovirus double-stranded (ds) RNA or synthetic dsRNA (e.g. poly I:C) as an activator and VAI RNA as an inhibitor. When used in the same reaction, dsRNA and VAI RNA are added simultaneously to the enzyme mix. The reactions are incubated at 30 C. for 15–25 min, then filtered through nitrocellulose in a slot-blot or dot-blot apparatus, prepared as in Example 4. $^{32}$P incorporated into the p68 kinase by autophosphorylation is quantitated by liquid scintillation counting or by laser densitometry of an exposed autoradiographic film. A typical test series includes the following reactions: a) control reactions with p68 kinase alone or VAI RNA alone; b) control reactions with test compound alone or with either p68 kinase or VAI RNA; c) p68 kinase and VAI RNA; and d) p68 kinase, VAI RNA and test compound. For test compounds which interfere with binding of viral inhibitor to p68 kinase, the amount of autophosphorylated p68 kinase detected in reaction (d) is more than that detected in reaction (c).

EXAMPLE 6

Preparation of p58

I. Preparation of p58 from Bovine Cells

A. General Methods

Madin-Darby bovine kidney (MDBK) cells (Etkind & Krug, 1975, *J. Virology* 16, 1464–1475) are grown in monolayers as described (Katze, et al., 1988, *J. Virology* 62, 3710). Monolayers of MDBK cells ($2\times10^{10}$ cells; 800 T150 flasks) are infected with influenza virus at a multiplicity of infection (m.o.i.) of 10 plaque-forming units per cell for 4 hours. The infected cells are washed twice with ice-cold Hanks, balanced salt solution and lysed in buffer A:50 mM Tris-HCl, pH 7.5, 50 mM KCl, 1 mM dithiothreitol, 2 mM $MgCl_2$, aprotinin at 100 µg per ml, 1 mM phenylmethylsulfonyl fluoride, 1% Triton X-100. The cytoplasmic extracts are then centrifuged at 100,000×g for 1 hour in a Beckman Ti 70.1 rotor. The supernatant (S100) is fractionated by ammonium sulfate precipitation (40–60%). The ammonium sulfate precipitate is resuspended in buffer B: 20 mM Tris-HCl, pH 7.5, 1 mM EDTA, 0.1 mM phenylmethylsulfonyl fluoride, 5% glycerol supplemented with 100 mM KCl and dialyzed against the identical buffer. The dialyzed sample is applied to a Mono Q HR 10/10 column. Bound proteins are eluted with a 100-ml linear gradient of 100–500 mM KCl in buffer B. Kinase-inhibitory activity is assayed as described in B below. The kinase inhibitory material elutes at 280 mM KCl. Active fractions are pooled, concentrated by using a Centriprep 30 concentrator (Amicon, Danvers, Mass.), and dialyzed against buffer B containing 25 mM KCl. The dialyzed fraction is applied to a heparin-agarose column and bound material is eluted by sequential application of buffer B containing, respectively, 100, 300, and 500 mM KCl. The kinase inhibitory activity is found in the 300 mM KCl fraction, which is then concentrated and dialyzed against buffer B/25 mM KCl. The dialysate is loaded onto a Mono S HR 5/5 column, and bound material is eluted with buffer B/250 mM KCl. To achieve the final purification, the active Mono S fraction is layered onto a 10–30% glycerol gradient containing buffer B/25 mM KCl. The gradient is centrifuged at 49,000 rpm for 21 hours in a Beckman SW 55 rotor. Fractions are collected, dialyzed, and assayed for kinase inhibitory activity as described below.

B. Assay for Inhibition by p58

This assay allows purification of p58 from influenza virus-infected cells to be monitored. Fractions isolated during the p58 purification procedure are mixed with a p68-containing cell extract prepared by disruption of interferon-treated 293 cells with Triton X-100, and incubated for 20 minutes at 30 C. The p68 kinase is then immunoprecipitated using an antibody which recognizes the human p68 from 293 cells but not the bovine homologue in influenza virus-infected MDBK cells, the source of the p58. The activity of the immunoprecipitated p68 kinase is then measured using [gamma-$^{32}$P]ATP and exogenously added histones as substrates. To quantitate activity, histones are subjected to polyacrylamide gel electrophoresis and excised from the gel. In the later stages of purification, an additional assay using pure p68 kinase and its natural substrate, eIF-2, is performed as follows. Fractions from the purification are preincubated with pure p68 kinase for 10 minutes at 30 C. in buffer C (17 mM Tris-HCl, pH 7.5, 75 mM KCl, 0.1 mM EDTA, 1.0 mM diethiothreitol, aprotinin at 8 µg per ml, 0.1 mM phenylmethylsulfonyl fluoride, 2 mM $MgCl_2$, 2 mM $MnCl_2$, 0.3 mg of bovine serum albumin per ml, 8% glycerol). Activator poly(I):poly(C) (0.010 µg/ml) is then added in the presence of 1 mM [gamma$^{32}$P]ATP (424 Ci/mmol; 1 Ci=37 GBq) and incubation continued for an additional 10 minutes. Finally, 0.5 µg of purified eIF-2 is added and incubation is continued for a further 10 minutes at 30 C. The reaction is terminated by addition of 2× disruption buffer (160 mM Tris, pH 6.8, 1.0 M 2-mercaptoethanol, 4% SDS, 20% (vol/vol) glycerol), the mixture is boiled, and the phosphorylated proteins are analyzed on an SDS/14% polyacrylamide gel.

A. Screening of cDNA Library

Three tryptic peptides derived from purified p58 protein were sequenced by microsequencing. One of the sequences (AEAYLIEEMYDEAIGDYETA) (SEQ ID NO:11) was used to design a degenerate oligonucleotide probe (5'-GAA (G)GAA(G)ATGTAT(C)GAT(C) GAA(A)GC-3'). (SEQ ID NO:12) This was used to screen a cDNA library from the MDBK cell line made in the Lambda Zap II vector (Stratagene). Duplicate plaque transfers were made to nylon filters (Hybond-N; Amersham, Arlington Heights, Ill.). Filters were then prehybridized in 6× SSPE (1× SSPE=0.18 M NaCl/10 mM $NaPO_4$, pH 7.4, 1 mM EDTA, 1% SDS, 0.2% Ficoll, 0.2% bovine serum albumin, 0.2% polyvinylpyrrolidone) 100 µg of sonicated and denatured salmon sperm DNA per ml at 38 C for 4 hours and hybridized with $^{32}$P-5'-end-labeled probe in 6× SSPE, 1% SDS, 100 µg of sonicated and denatured salmon sperm DNA per ml at 38° C. for 20 hours. Filters were washed in 6× SSPE, 1% SDS twice at room temperature for 10 minutes, once at 38 C for 15 minutes and exposed at −70 C with Kodak X-Omat film with enhancing screens. Positive phage plaques were identified and purified by further rounds of plaque hybridization. The pBluescript plasmid (Stratagene) was excised out in vivo according to the manufacturer's instructions. EcoR I fragments from 4 positive clones were analyzed by Southern blot hybridization using the degenerate oligonucleotide probe p58-3-2 (5'-GCIGTT(C)TCA(G) TAA(G)TCT(C)TG-3' (SEQ ID NO:18); I represents inosine) corresponding to the antisense-strand of a partial amino acid sequence (QDYETA) (SEQ NO:14) of the p58. One positive clone containing an insert of 1400 bp was obtained and analyzed by restriction enzyme mapping. After cloning into M13mp18 and M13mp19, the sequence of the p58 cDNA was determined by the dideoxynucleotide chain-termination method using Sequenase 2.0 (United States Biochemical). Sequence data were analyzed using the Genetics Computer Group (GCG) sequence-analysis program (version 7.0). B. Isolation of the 3' End Region of p58 cDNA The initial clone isolated contained a long open-reading frame but no termination codon, suggesting that the 3' end was missing. The missing 3' end region was isolated using RACE-PCR (Rapid Amplification of cDNA ends-polymerase chain reaction) as described (Innis, et al., 1990). MDBK poly (A)+mRNA (1 µg) was reverse-transcribed using a hybrid primer (5'-GACTCGAGGATCCGAATTC-$(T)_{17}$-3'). (SEQ ID NO:15) The cDNA pool was amplified by RACE-PCR in the presence of adapter primer (5'-GACGCGACCATCCGAATTC-3') (SEQ ID NO:16) and p58 gene-specific primer P58-5 (5'-GCTGAAGAGCTCATCAAAG-3') (SEQ ID NO:17) under the conditions as described (Innis, et al., 1990). After identifying the amplified product by Southern blot, the product was isolated from an agarose gel and cloned into M13mp18 and m13mp19 to sequence the amplified region. This allowed reconstruction of the complete p58 cDNA containing 1680 bp. The original 1400 bp cDNA was also used to screen the MDBK cDNA library and pull out another clone of 3140 bp containing the full coding sequence together with 5'- and 3'-UTRs.

C. Expression of Fusion Protein in Bacteria

A unique Nde I site (CATATG) was introduced at the initiating metyionine codon of the p58 gene using an in vitro mutagenesis kit (Bio-Rad, Richmond, Calif.) according to the manufacturer's protocol. After site-directed mutagenesis, a 1.6 kb Nde l-BamH I fragment containing the p58 gene was cloned into the bacterial expression vector pET15b (Novagen, Madison, Wis.). p58 was expressed as a histidine-tagged fusion protein in E. coli BL21 (DE3)pLysS after inducing with 0.2 mM IPTG for 2 hours at 30° C. Most of the fusion protein was found in the insoluble fraction. After denaturing this fraction in 6 M Guanidium-HCl, the fusion protein was purified using a Ni(II)-column in accordance with the manufacturer's instructions. The purified protein (0.1 mg/ml) was renatured after diluting about 50-fold in the dialysis buffer (20 mM Tris-HCl, pH 7.5, 1 mM DTT, 0.1 mM EDTA, 0.15 M NaCl, 20% glycerol) containing 0.1 mg bovine serum albumin per ml and dialyzing in dialysis buffer at 4° C. for 6 hours. The renatured protein was aliquoted and stored at −70° C.

EXAMPLE 7

Screening Method: Inactivation of p68 by p58

This assay is performed in essentially the same way as the procedure in example 5. Up to 2 μl of p68 kinase fraction (the exact volume used depends on the degree of purification) is diluted to 10 μl with 50 mM KCl, 20 mM HEPES (pH 7.4), 1.5 mM $MgCl_2$, 0.1 mM EDTA, 1 mM DTT, 10% glycerol and 1 μM PMSF, 0.1 mg bovine serum albumin and 0.1 mg of tRNA per ml. The diluted kinase is added to 20-μl reaction mixtures containing, at final concentrations, 75 mM KCl, 25 mM HEPES, (pH 7.4), 10 mM $MgCl_2$, 1.0 mM dithiothreitol, 0.1 mM EDTA, 0.1 mM ATP, protease inhibitors, and 5 to 10 μCi of [gamma $^{32}P$] ATP (>3,000 Ci/mmol; Dupont, NEN). Reaction mixtures are supplemented as appropriate with reovirus double-stranded (ds) RNA or synthetic dsRNA (e.g. poly I:C) as an activator and p58 as inhibitor. When used in the same reaction, dsRNA and p58 are added simultaneously to the enzyme mix. The reactions are incubated at 30 C. for 15–25 min, then filtered through nitrocellulose in a slot-blot or dot-blot apparatus, prepared as in Example 4. $^{32}P$ incorporated into the p68 kinase by autophosphorylationis quantitated by liquid scintillation counting or by laser densitometry of an exposed autoradiographic film; A typical test series includes the following reactions: a) control reactions with p68 kinase alone or p58 alone; b) control reactions with test compound alone or with either p68 kinase or p58; c) p68 kinase and p58; and d) p68 kinase, p58 and test compound. For test compounds which interfere with binding of p58 inhibitor to p68 kinase, the amount of autophosphorylated p68 kinase detected in reaction (d) is more than that detected in reaction (c).

EXAMPLE 8

In vitro Translation Assay

The following components are added in sequence to 12 μl of micrococcal nuclease-treated rabbit reticulocyte lysate: 2.5 μl of 50 mCi/ml [$^{35}S$] methionine, 2.5 μl of an amino acid mixture containing 1 mM of all amino acids except methionine, 2.5 μl of 50 μg/ml VAI RNA, 2.5 μl of 100 ng/ml reovirus double-stranded RNA, and 2 μl of test compound or $H_2O$. The mixture is incubated at 30 C. for 15–20 min to allow activation of endogenous p68 kinase, then 1 μl of specific reporter gene mRNA is added to give a final concentration of 10 μg/ml. The translation reaction is then incubated for 30 min at 30 C. Translation is quantitated by SDS-PAGE and autoradiography, by CAT or luciferase enzyme assays, or other assay as appropriate for the mRNA used. A typical test series includes the following reactions: a) control reaction without reovirus dsRNA or VAI RNA; b) control reaction with reovirus dsRNA but without VAI RNA; c) reovirus dsRNA and VAI RNA; and d) reovirus dsRNA, VAI RNA, and test compound. For test compounds which interfere with VAI RNA function, translation in reaction (d) is reduced compared to that detected in reaction (c).

EXAMPLE 8a

Identifying Antisense Oligodeoxynucleotide Molecules that Interfere with the Function of an Adenovirus Gene Product, VAI RNA.

The following example provides compositions and methods which specifically block the function of adenovirus VAI RNA, which is known to inhibit the activation of a cellular antiviral enzyme p68. Inhibition of p68 activation is important for replication of adenovirus in vivo, and essential for viral resistance to interferon. Any compound that specifically blocks the function of VAI RNA would be expected to inhibit adenovirus replication since it would inhibit a key step in the viral life cycle.

The interferon response is a primary defense mechanism against viruses. In response to viral infection, mammalian cells secrete interferon, which in turn induces the production of several enzymes that have antiviral effects (Sen, G. C. and P. Lengyel. 1992, J. Bio. Chem. 267:5017–5020). One of these enzymes is a protein kinase designated here as p68, but also known as PKR, for Protein Kinase RNA-activated, eIF2 kinase, dsRNA-PK, DAI, P1 kinase, and dsI. This enzyme is induced in an inactive form by interferon, and is activated only after interaction with double stranded RNA (dsRNA), which is usually produced during viral infection (Hershey, J. W. B. 1993, Seminars in Virology 4:201–207. Samuel, C. E. 1993, The eIF-2a protein kinases, regulators of translation in eukaryotes from yeasts to humans. J. Bio. Chem. 268:7603–7606). Once activated, p68 phosphorylates eukaryotic initiation factor 2 (eIF2). Phosphorylation of eIF2 leads to inhibition of translation, both cellular and viral. Since viruses are obligate intracellular parasites that depend on their host cell for translation, the viral life cycle is blocked by this inhibition of translation.

Many viruses possess counterdefenses to allow them to replicate in spite of interferon and its induced antiviral enzymes. Several viruses are known to produce specific inhibitors of p68 (Katze, M. G. 1993, Seminars in Virology 4:259–268. Mathews, M. B. 1993, Seminars in Virology 4:247–257). Among these is adenovirus, which produces a specialized RNA, designated VAI RNA, that specifically inhibits p68. VAI RNA is essential for the observed resistance of adenovirus to interferon; mutants without a functional VAI RNA are sensitive to interferon. VAI RNA is a 150 base single stranded RNA molecule with internal base pairing that results in a complex structure of double stranded stems and single stranded loops (FIG. 1). The molecule is roughly divided into regions designated the terminal stem, the central domain, and the apical stem-loop. Some of these regions of secondary structure have been identified as essential to the function of VAI RNA (Mathews, M. B. and T. Shenk. 1991, J. Virol. 65:5657–5662. Mellits, K. H., T. Pe'ery, and M. B. Mathews 1992, J. Virol. 66:2369–2377).

Miroshnichenko, et al, 1989. "Inhibition of adenovirus 5 replication in COS-1 cells by antisense RNAs against the viral E1A region." Gene 84:83–89 reported that antisense RNA to the early adenovirus gene product E1A could reduce plaque yield. E1A is functionally unrelated to VAI RNA, and does not play a role in inhibition of p68. Their experiments did not use exogenously added antisense oligodeoxynucleotides, but relied on the transfection of a plasmid encoding an antisense RNA.

Figure 2:
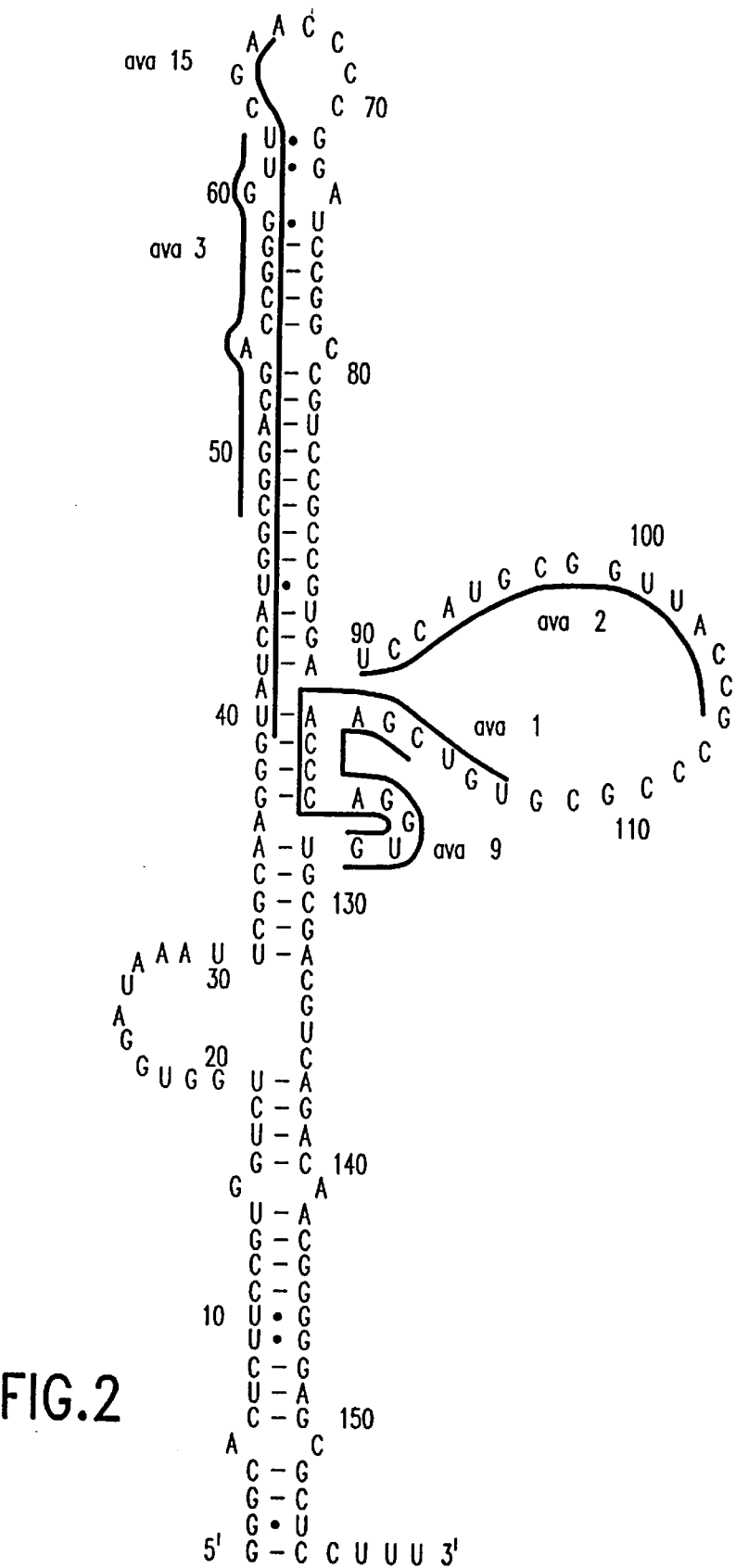
FIG. 2 shows the antisense VA (ava) oligodeoxynucleotide species ava 1, ava 2, ava 3 and ava 9 annealed to complementary sequences of VAT RNA. (SEQ ID NO.20)

Based on the known base sequence of VAI RNA, the predicted secondary structure (FIG. 1), and the relative importance of the various stems and loops to VA function, applicant designed several antisense oligodeoxynucleotide molecules (FIGS. 2,3). These antisense species were tested in the in vitro translation assay described above.

A. In vitro Translation Assay.

The in vitro translation assay was performed in a 96 well plate. Rabbit reticulocyte lysate was used as a source of. p68 as well as an in vitro translation system. p68 is present in rabbit reticulocyte lysates, and can be activated by the addition of dsRNA such as reovirus RNA. When p68 is activated, translation is inhibited. Means for monitoring levels of translation are utilized. For example, translation can easily be monitored by assaying for reporter gene expression, such as chloramphenicol acetyltransferase and others as are known in the art. In one embodiment luciferase may be used as a reporter protein since it can be quantitated in a luminometer. Compounds that activate p68 (e.g. reovirus RNA) will cause inhibition of translation and result in a decreased reporter protein, such as luciferase, signal. Addition of VAI RNA to the reaction containing reovirus RNA will result in an increase in luciferase signal as the VAI RNA inhibits activation of p68 and allows translation to continue. Antisense oligodeoxynucleotides were added to the reaction containing reovirus RNA and VAI RNA. Antisense species that interfere with VAl RNA function will lead to a decrease in luciferase signal.

VAI RNA was prepared as described in the main body of this patent (see Example 2: Preparation of viral inhibitors, A. VAI RNA). The following components were added in order and incubated as indicated in wells of a 96 well plate:

4 $\mu$l of antisense oligodeoxynucleotide (final concentration is 20 fold molar excess to VAI RNA)

2 $\mu$l of VAI RNA (final concentration=5 $\mu$g/ml)

20 $\mu$l rabbit reticulocyte lysate supplemented with 1 mM complete amino acid mixture.

Incubate at 30° C. for 15 min.

2 $\mu$l reovirus dsRNA (final concentration=10 ng/ml)

Incubate at 30° C. for 15 min.

2 $\mu$l luciferase mRNA (final concentration: 30 ng/ml)

Incubate at 30° C. for 15 min.

The wells were immediately assayed for luciferase activity using a Dynatech ML3000 luminometer and Analytical Luminescence Labs Enhanced Luciferase Assay Kit. Settings were: Enhanced Flash mode, Delay=2s, Integrate=5s, 50 $\mu$l Substrate A injected simultaneously with 50 $\mu$l Substrate B.

The following controls were included in the assay. $H_2O$ was also substituted for mRNA, reovirus RNA, or VAI RNA as indicated by (−).

Figure 4:
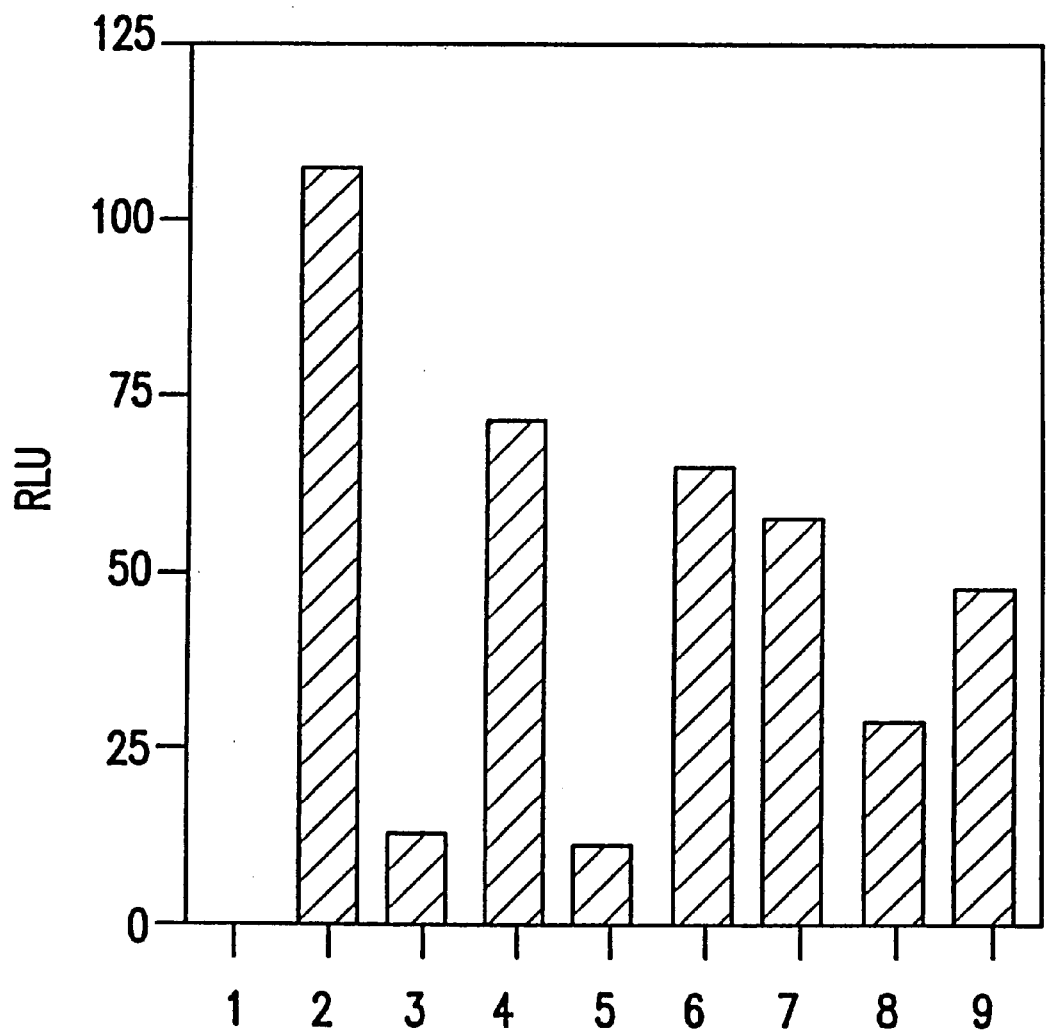
FIG. 4 shows the result of in vitro translation assay. Column 1: (−) mRNA; column 2: (+) mRNA; column 3: (+) mRNA, (+) reovirus dsRNA; column 4: (+) mRNA, (+) reovirus dsRNA, (+) VAI RNA. Columns 5–9: (+) mRNA, (+) reovirus dsRNA, (+) VAI RNA, and antisense as follows: column 5: ava 1; column 6: ava 2; column 7: ava 3; column 8: ava 9; column 9: ava 15.

1) (−) mRNA (−) reo (−) VA
2) (+) mRNA (−) reo (−) VA
3) (+) mRNA (+) reo (−) VA
4) (+) mRNA (+) reo (+) VA Control 1 tested for the presence of anything in the lysate that might give a positive luciferase signal without luciferase mRNA. Control 2 established normal level of translation for the assay. Control 3 established the level of inhibition of translation that was a result of reovirus RNA activation of p68. Control 4 determined the rescue function of VAI RNA as an inhibitor of p68 in the presence of the activator, reovirus RNA. Typical results are shown in FIG. 4. The production of Relative Light Units ("R.L.U.") is dependent on the addition of luciferase mRNA (column 1 vs. 2). When reovirus dsRNA was added to the assay, the endogenous p68 in the lysate was activated and translation was inhibited (column 3). When VAI RNA was added, translation was partially rescued (column 4).

B. Antisense Oligodeoxynucleotide Results.

Ancisense oligodeoxynucleotides species were added to the assay; these results are also shown in FIG. 4. Ava 1 was found to completely reverse the effect of VAI RNA (column 5). Ava 9, and ava 15 were partially antagonistic to VAI RNA function (columns 8, 9). Ava 2 and 3 did not significantly affect VAI RNA function (columns 6, 7). Other antisense species, including species complementary to the terminal stem region, did not interfere with VAI RNA function (data not shown). These latter results underscore the specificity of inhibition by ava 1, since antisense to some parts of the VAI RNA molecule are not effective in blocking function.

Applicant shows that the aforesaid block of VAI RNA function is not dependent on RNase H cleavage of the RNA-DNA hybrid formed by VAI RNA and ava species. Therefore, the sequences of the oligodeoxynucleotides designated ava 1, 9, and 15 synthesized as modified RNA or DNA would be expected to function effectively. By "modified DNA or RNA" is meant that nucleic acid base analogs as are known in the art may be present, for example, DNA analogs could include, but are not limited to, methylphosphonate DNA or phosphorothioate DNA. DNA analogs may provide advantages such as nuclease resistance and increased cellular uptake. Additionally, one base, for example adenine may be substituted for another base, for example, guanine; the phosphodiester linkage may be modified as is known in the art, for example by substitution of a thioester linkage; or the sugar moiety of the nucleic acid may be modified as is known in the art, for example, substitution of 2'-deoxyribose with ribose or substitution of ribose with 2'-deoxyribose. These modifications may be made to one or more bases in the nucleic acid sequence. Modifications also include changes which, for example, stabilize the nucleic acid, but do not effect the function of the nucleic acid (as can be determined by routine testing).

Not every antisense oligodeoxynucleotide interferes with VAI function, as shown by the fact that ava 2 and several other antisense species complementary to various regions of VAI RNA did not affect VAI activity. Ava 2 is complementary to part of the central domain of VAI RNA. Since this complementary region of VAI RNA is single-stranded, ava 2 would be expected to anneal readily, and since the central domain has been shown to be critical for function (Mathews, M. B. and T. Shenk. 1991. Adenovirus virus associated RNA and translation control. J. Virol. 65:5657–5662. Mellits, K. H., T. Peery, and M. B. Mathews. 1992. Role of the apical stem in maintaining the structure and function of adenovirus virus associated RNA. J. Virol. 66:2369–2377), ava 2 would be expected to interfere with VAI function. However, ava 2 did not affect VAI activity (FIG. 4).

In contrast, ava 15 is complementary to a double-stranded region of VAI RNA. This region would not be expected to easily allow binding of an oligodeoxynucleotide, and yet the antisense oligodeoxynucleotide ava 15 does in fact antagonize VAI function (FIG. 4). By utilizing Applicant's method, screening of oligonucleotides for those which are functional may be easily accomplished. More generally, the ready detection by the Applicant's screening method of the unexpected nature of the behavior of both ava 2 and ava 15 demonstrates the utility of the method for identifying antagonists of viral inhibitors of p68.

EXAMPLE 9

Monitoring p68 Activity as a Function of Translation of GCN4-reporter Gene Fusions in in vitro Extracts.

To provide a positive signal in response to activation of p68 kinase, in vitro translations are performed using an mRNA which carries part of the untranslated leader for the yeast GCN4 protein fused to the coding sequence for beta-galactosidase. Translation of such GCN4 fusions in yeast cells is increased in the presence of activated p68 kinase.

Plasmids pM23 and pM226 (Miller & Hinnebusch, 1989, Genes Dev. 3, 1217) each carry a GCN4-lacZ fusion and genes necessary for plasmid selection and maintenance in E. coli and S. cerevisiae. These two plasmids differ by a single nucleotide: whereas pM23 has the two upstream open reading frames (ORF1 and ORF4) which together confer p68-sensitive regulation, mutation of the ORF1 ATG codon leaves pM226 with only ORF4 which by itself confers constitutive, low level expression. In order to provide a T7 promoter for efficient in vitro transcription, the Sal I-Bgl II fragments of pM23 and pM226 are replaced with a PCR-generated fragment (PCR-1 or PCR-2, respectively) as follows. PCR-1 and PCR-2 are made using oligos T7-1 (5' gcg tcg act aat acg act cac tat agg gag TCT TAT ATA ATA GAT ATA CAA AAC, with lower case for a Sal I recognition site and the T7 RNA polymerase promoter, and upper case for GCN4 sequence starting with the 5' end of the native mRNA), and T7-2 (5' GGG AAA TTT TTA TTG GCG AGT AAA CCT GG, residues 503 to 475, relative to the transcription start site) as primers, plasmids pM23 and pM226, respectively, as templates, and a standard GeneAmp™ PCR kit from Perkin Elmer. The PCR-generated fragments are cloned directly using the TA-cloning kit from Invitrogen. The promoter fragments are excised with Sal I and Bgl II and subcloned into pM23 and pM226, respectively, that have been digested with the same two enzymes.

The modified plasmids are transcribed in vitro with T7 RNA polymerase and translated in vitro as described above. Beta-galactosidase activity is measured using standard assay conditions for the enzyme. If it becomes desirable to use a reporter gene other than beta-galactosidase, the lacZ gene is bracketed by two Bam HI sites, which can be used for excision and replacement with the new reporter gene.

EXAMPLE 10

Construction of Yeast Strain for Screening

The starting point for the p68 kinase assay strain is the strain designated H1895, which has the genotype: a ura3-52 leu2-3 leu2-112 trp1-Δ63 gcn2Δ[GCN4-lacZ TRP1] at trp1-Δ63 (Dever et al., 1993, Proc. Natl. Acad. Sci. US). Because this strain is deleted for GCN2, it lacks the kinase normally responsible for inducing the GCN4 pathway and is therefore dependent upon an exogenous kinase (i.e the mammalian p68 kinase) for activating GCN4. Expression of GCN4 is conveniently monitored in this strain by using a GCN4-lacZ fusion which directs the synthesis of beta-galactosidase under GCN4 control. The plasmids p1420 and p1419 (Id.) are, respectively, high and low copy number URA3 plasmids, which contain the cloned p68 kinase gene under the control of the GAL-CYC promoter.

Plasmid pMHVA (Mellits & Mathews, 1988, EMBO J., 7, 2849–2859) containing the gene encoding VAI RNA was digested with Xba I and Pst I and the fragment containing the VAI RNA gene, its promoter and transcription terminator was inserted into high- and low-copy number LEU2 plasmids p425 & p315, respectively (Sikorski & Heiter, Genetics, 122, 19–27, 1989; Christianson et al., Genetics, 110, 119–122, 1992) that had been digested with Spe I and Pst I. All restriction digestions and ligations were performed according to manufacturers' instructions.

Strain H1895 was then transformed with all pairwise combinations of the low and high copy number plasmids containing the VAI RNA and p68 kinase genes by selecting for growth on minimal medium lacking histidine and leucine. This yielded a battery of strains suitable for evaluating the interaction between p68 and VAI RNA (in the presence or absence of galactose) and for choosing which combination of plasmids is optimum for the desired assay.

EXAMPLE 11

In vitro Assays for Degradation of p68 by Poliovirus

To prepare radiolabeled p68, suspension HeLa cells are incubated in medium containing [$^{35}$S]methionine (500 μCi/ml) together with human lymphoblastoid alpha and beta interferon for 16 hours. After harvest, cells are washed in ice-cold Hank's Balanced Salt Solution (HBSS) and disrupted in lysis buffer (10 mM Tris.HCl, pH 7.5, 50 mM KCl, 2 mM MgCl$_2$, 2 mM MnCl., 0.1 mM EDTA, 0.2 mM phenylmethylsulfonyl fluoride, 1% Triton X-100). Alternatively, radiolabeled p68 is prepared by in vitro transcription of a cDNA clone followed by in vitro translation in wheat germ extracts under standard conditions and in the presence of [$^{35}$S]methionine.

To prepare test extracts from infected and uninfected cells, HeLa cells are grown in suspension and either infected with poliovirus or mock infected five hours before harvest. Cells are then harvested and extracts made as for radiolabeled cells. To test for p68-degrading activity, the extract from radiolabeled cells is mixed with extract from either infected or mock-infected cells and incubated at 30° C. for 15 minutes. Alternatively, the radiolabeled products of the in vitro transcription and translation of the p68 cDNA clone are mixed with extract from either infected or mock-infected cells and incubated at 30° C. for 15 minutes. In either case, radiolabeled p68 is immunoprecipitated after incubation with the cell extracts using a monoclonal antibody (available from A. Hovanessian, Institut Pasteur, although other antibodies are readily prepared with equivalent effect) bound to Sepharose. Immunoprecipitated material is subjected to polyacrylamide gel electrophoresis, detected by autoradiography and quantitated by laser densitometry.

EXAMPLE 12

Partial Purification of p68 Oroteolytic Activity from Poliovirus-infected Cell Extracts 2×10' HeLa cells grown in suspension are infected with poliovirus for 5 hours at a multiplicity of infection (m.o.i.) of 20 plaque-forming units (pfu) per cell. As a control, a similar number of cells are mock-infected for the same period. Cells are harvested and washed in ice-cold Hank's Balanced Salt Solution (HBSS) and then disrupted in lysis buffer (10 mM Tris.HCl, pH 7.5, 50 mM KCl, 2 mM MgCl$_2$, 2 mM MnCl$_2$, 0.1 mM EDTA, 0.2 mM phenylmethylsulfonyl fluoride, 1% Triton X-100). Nuclei and membranes are removed by centrifugation at 4,000×g for 10 minutes. Pooled extracts from infected or mock-infected cells are subjected to sequential differential precipitations using ammonium sulfate at 20%, then 40%, then 60%, and finally at 80% saturation. Pellets are resuspended and dialyzed against lysis buffer containing 5% glycerol. The pellet and supernatant from each precipitation is tested in the p68 degradation assay described above (Example 9).

Nucleic Acid Targets

One particularly useful macromolecule target is a nucleic acid. There now follows a detailed review of useful methods of this invention which are based upon targeting agents of this invention to such nucleic acids.

Viruses are believed by Applicant to employ nucleic acid sequences responsible for preferential translation of viral RNAs. Viruses whose RNAs are believed to be preferentially translated because of specific viral nucleic acid sequences currently include picornaviruses, hepatitis B virus, hepatitis C virus, influenza virus, adenovirus and cytomegalovirus.

Picornaviruses are an important class of viruses responsible for a broad array of human and animal diseases (reviewed in Chapters 20–23 in Fields BN, Knipe D M (eds): *Fields Virology*, ed. 2, Raven Press, New York, 1990). They include polioviruses, rhinoviruses (the most frequent cause of respiratory tract infections), coxsackie viruses (a cause of gastrointestinal illnesses, myocarditis and meningitis), hepatitis A virus, and foot-and-mouth disease viruses. Picornaviruses are single-stranded RNA viruses whose RNA genomes are positive-sense and nonsegmented. The genomic RNA strand inside each virus is translated when the virus enters a host cell. One of the proteins translated from the incoming RNA genome is an RNA-dependent RNA polymerase which copies the viral genome to produce additional full-length viral RNAs. Some of these RNAs are translated to produce additional viral proteins, and some are packaged as RNA genomes into a new generation of viruses. Each RNA is translated into a single "polyprotein" which is cleaved as it is translated to yield individual viral proteins.

One of the early effects of infection with a picornavirus is a shutoff of host protein synthesis. At least in the case of poliovirus infection, this appears to be due to cleavage of a host cell protein known as p220, one of three polypeptide constituents of the initiation factor eIF-4F, also known as cap-binding protein complex. eIF-4F is required for initiation of protein synthesis from host cell mRNAs, which bear a structure known as a cap at their 5'-ends. eIF-4F is believed to bind to the cap structure and participate in the unwinding of secondary structure adjacent to the cap in the 5'-untranslated leader (5'-UTR) of mRNAs. This unwinding is necessary for ribosomes to bind to the mRNA and migrate along it to the AUG codon which represents the start of the coding sequence. Thus, by cleaving one of the subunits of eIF-4F, picornaviruses prevent cap-dependent initiation of translation of host-cell mRNAs, and thereby disable host-cell protein synthesis. Viral RNAs can be translated, however, because they utilize a cap-independent mechanism for initiation; indeed, picornaviral RNAs do not have caps at their 5'-ends. Some but not all scientists in the field believe that the cap-independent mechanism involves sequences within the 5'-UTR of the viral RNAs known as internal ribosomal entry sites (IRES, or IRES elements) or ribosomal landing pads (RLPs) (reviewed in Sonenberg & Meerovitch, 1990). As their names imply, these are sequences which enable ribosomes to bind to viral RNAs at internal sites rather than at the 5'-ends of these RNAs; having bound, the ribosomes can then migrate to the AUG initiator codon and begin translation. Such binding at internal sites allows the ribosomes to bypass the virus-induced defect in the normal cap-dependent mechanism of initiation.

The existence of IRES elements in picornaviral RNAs was inferred from several different types of observation (see Sonenberg & Meerovitch, 1990). So, for example, viruses with mutations in the 5'-UTR were found to make significant amounts of viral RNA but very little viral protein. More direct evidence came from the studies with dicistronic mRNAs in which the poliovirus 5'-UTR (for example) was positioned between the coding sequences for two separate proteins in a single mRNA. Experiments both in vivo and in vitro demonstrated that the second-cistron could be translated under conditions in which the first was not, for example, in virus-infected cells or in the presence of an inhibitor of cap-dependent translation, but that in the absence of the viral 5'-UTR from the intercistronic space, translation of the second cistron depended on translation from the first. Further refinement of such experiments, involving for example progressive deletions from either end of the 5'-UTR, permitted more precise definition of the region within the 5'-UTR which constitutes the IRES element. Proteins which interact with IRES elements were then identified by gel-retardation assays and UV-cross-linking studies.

Evidence that IRES elements are indeed important for translation has been obtained by demonstrating that the 5'-UTR of encephalomyocarditis virus (EMCV) or fragments thereof can act as competitive inhibitors of translation in vitro (Pestova et al. (1991) *J. Virol,* 6194–6204) and that short DNAs complementary to the EMCV IRES element can also block translation in vitro. (Shih et al., (1987) *J. Virol.* 2033–2037, Pestova et al. (1989) *Virus Research,* 107–118 Borovjagin et al., (1991) *Nucl. Acids Res.,* 4999–5005).

Despite these studies there is still controversy about whether translational initiation at IRES elements really occurs, and some evidence to suggest that it does not. Thus, one authority in the field has argued strongly that important controls were omitted from crucial experiments supporting the existence of IRES elements, characterizing these experiments as flawed or inconclusive and IRES elements as artifacts (Kozak (1989) *J. Cell Biol.* 229–241; Kozak (1992) *Crit. Rev. Biochem. Mol. Biol.* 385–402). It has also been demonstrated that if a cap is added to poliovirus RNA, which does not normally have such a structure, translation of the poliovirus RNA is inhibited (Hambridge S J & Sarnow P, (1991) *J. Virology* 65, 6312–6315). This observation is at odds with the purported ability of ribosomes to initiate translation of poliovirus RNA by binding to IRES elements downstream of the 5'-cap.

Even if IRES elements do function as their proponents claim, the mechanism may not be unique to viruses. Thus it has been reported that internal ribosome entry sites exist within cellular mRNAs (Macejak & Sarnow (1991) *Nature,* 90–94; Jackson (1991) *Nature,* 14–15). The existence of such sites within cellular mRNAs would suggest that it may be difficult to identify compounds which prevent translational initiation at viral IRES elements without adversely affecting the translation of at least some cellular mRNAs.

Picornaviruses may not be the only viruses which utilize special sequences to enable ribosomes to bind at internal sites within RNAs and thus ensure preferential translation of viral proteins. Evidence for a similar mechanism has also been found in the case of hepatitis B virus and hepatitis C virus. Note that since hepatitis A virus is a picornavirus, this means that virtually all clinically significant hepatitis disease is caused by viruses which utilize internal ribosome entry sites.

Hepatitis B virus is a hepatovirus which can cause severe liver disease and which is very widespread (reviewed in chapter 78 of Fields B N, Knipe D M (eds): *Fields Virology,* ed. 2, Raven Press, New York, 1990). The virus has a very unusual genome and an equally unusual method of replication. In brief, the viral genome consists of partially double-stranded DNA. The negative-sense strand is a full circle, but the two ends of this circle are not covalently joined. The positive-sense strand is incomplete and its length is not the same in all molecules, so that the single-stranded region of the genome varies in length from approximately 15%–60% of the circle length in different molecules. When the virus infects a cell, the infecting genome appears to be converted to closed circular (cc) viral DNA which can be detected in the cell nucleus. This DNA is transcribed into (positive-sense) viral mRNAs, one of which encodes a reverse transcriptase which makes negative-sense DNA copies of viral RNA to produce further viral genomes. The (incomplete) positive-sense DNA strand of the genome is produced by partial copying of the negative-sense strand, with synthesis primed by a short viral oligoribonucleotide. The viral reverse transcriptase (P protein) is encoded within a long mRNA which also includes the coding sequence for the major viral core protein (C protein). The C-protein sequence is upstream of the P-protein sequence in the mRNA and partially overlaps it, in a different reading frame. Data from gene fusions which place a reporter gene downstream of the C-P overlap region suggest that translation of the P protein involves initiation at an internal ribosome entry site within the C-protein coding sequence (Chang et al., (1990), *Proc. Natl. Acad. Sci. USA* 87, 5158–5162). This interpretation is supported by the observation that defined fragments of the C-protein sequence increase translation of the downstream cistron when placed between the two cistrons of a dicistronic mRNA or in the 5'-UTR of a monocistronic mRNA (Jean—Jean et al., (1989) *J. Virology* 63, 5451–5454). Thus, the ability to translate a crucial viral protein is highly dependent upon the presence of a specific viral nucleic acid sequence translationally linked to the coding sequence.

Hepatitis C virus also appears to utilize specific viral nucleic acid sequences to bypass the normal cellular method for initiation of translation. As its name implies, hepatitis C is a causative agent of the diseases formerly known as non-A, non-B hepatitis. Like picornaviruses it has a positive-sense, single-strand genome which is translated as a single open-reading frame, presumably into a polyprotein precursor which is then cleaved to provide mature viral proteins. Given the much more recent discovery of hepatitis C virus, much less is known about it than the picornaviruses, and the evidence supporting its use of IRES-like elements is unclear. Thus on the one hand, experiments based on in vitro translation reactions led to the conclusion that translation of viral RNAs can be initiated at internal ribosome entry sites, but on the other hand, experiments in vivo found no evidence for such a mechanism of initiation (Yoo et al. (1992) Virology 889–899)

Influenza viruses also cause a dramatic inhibition of host cell protein synthesis during infection, while viral proteins are synthesized selectively and efficiently. Influenza viruses are of course the etiologic agents of the eponymous disease (for a review of these viruses see chapters 39 & 40 of Fields B N, Knipe D M (eds): *Fields Virology*, ed. 2, Raven Press, New York, 1990). They too have single-stranded RNA genomes, but in their case the genome consists of negative-sense RNA and each gene exists on a separate RNA segment which is encapsidated separately into the virion; the viruses are thus of the type known collectively as segmented negative-strand RNA viruses. After infection the separate RNAs are copied into positive-sense RNAs for translation. This copying is catalyzed by a virus-coded RNA-dependent RNA polymerase protein, but requires short capped pieces from the 5'-ends of cellular mRNAs to act as primers. These primers are derived from cellular mRNAs through the action of a virus-encoded endoribonuclease. Thus, the first 10–13 nucleotides of each positive-sense, translatable, influenza viral RNA is derived from cellular mRNA.

In cells infected with an influenza virus, newly synthesized cellular mRNAs do not reach the cytoplasm (Katze & Krug, (1984) *Mol. Cell. Biol.* 4, 2198–2206), and translation of pre-existing mRNAs is blocked at both the initiation and elongation stages (Katze et al.,(1986) *J. Virology* 60, 1027). Evidence that specific RNA sequences in influenza virus mRNA ensure its preferential translation came from the fact that influenza mRNAs were selectively translated in cells infected by another virus, adenovirus, despite the shutdown of host protein synthesis in these cells (Katze et al. 1986). Further progress in understanding the preferential translation of influenza RNAs came with the development of a transfection-infection assay (Garfinkel & Katze, (1992) *J. Biol. Chem.* 267, 9383 -9390). This was used to show that an exogenously introduced influenza viral gene was not subjected to the same translational blocks in infected cells as an exogenously introduced cellular gene. It was also concluded that translation of influenza mRNAs occurs in a cap-dependent manner, because such translation was inhibited by poliovirus infection, which blocks cap-dependent translation. Given that the 5'-ends of viral mRNAs are capped and derived from cellular mRNAs, this is not unexpected. For the same reason, it would not be expected that the 5'-UTR would play an important role in the preferential translation of influenza nRNA. Indeed, it was observed that there is nothing remarkable about the primary/secondary structure or length of the influenza 5'-UTR used for the transfection-infection assays described above. Unexpectedly, however, it has now been demonstrated that preferential translation of influenza mRNAs does depend on the 5'-UTR, and that the selectivity-determining region is surprisingly small, as small as 12 nucleotides. For comparison, a typical IRES element in a picornavirus has a length of about 400 nucleotides.

Most of the viruses so far described have been RNA viruses, but DNA viruses also appear to utilize special nucleic acid sequences which mediate preferential translation of viral RNAs. Adenovirus is an example of such a DNA virus (reviewed in chapters 60 & 61 of Fields B N, Knipe D M (eds): *Fields Virology*, ed. 2, Raven Press, New York, 1990). Adenovirus is responsible for various disorders including respiratory tract infections, conjunctivitis, hemorrhagic cystitis and gastroenteritis. The replicative cycle of adenovirus is significantly more complicated than that of the smaller picornaviruses and influenza viruses. Viral RNAs are transcribed from viral DNA by the host RNA polymerase II in two main phases, early and late transcription, with the late stage by definition starting with the onset of viral DNA synthesis, which is usually 6–9 hours after infection. That there is preferential translation of viral RNAs is demonstrated by a variety of observations. Host-cell protein synthesis is dramatically reduced in infected cells, even though cellular mRMA synthesis continues and there is no rapid breakdown of existing cellular mRNAs. Early in infection, early viral mRNA constitutes less than 0.1% of the total mRNA in the cell, but 5–18% of the mRNA in polysomes, that is, 5–18% of the mRNA which is being actively translated.

The mechanisms by which adenovirus accomplishes its takeover of protein synthesis are not fully understood, but it has been demonstrated that dephosphorylation of a component-of the cap-binding protein complex, eIF-4E, may play a role in this takeover (Huang & Schneider, (1991), *Cell* 65, 271–280). In support of this, it has also been shown that adenovirus mRNAs containing special sequences known as tripartite leader sequences are translated in a cap-independent manner (Dolph et al., (1988) *J. Virology* 62, 2059–2066). Thus, preferential translation of adenovirus mRNAs also appears to depend upon specific viral nucleic acid sequences.

A DNA virus belonging to the herpes family, cytomegalovirus, may also utilize specific viral nucleic acid sequences to ensure preferential translation of viral RNAs. Cytomegalovirus is endemic in many populations, but many infections are subclinical in normal healthy individuals (reviewed in chapter 69 of Fields B N, Knipe D M (eds): *Fields Virology*, ed. 2, Raven Press, New York, 1990). The virus can cause serious illness, however, in immunosuppressed individuals, and has become a significant pathogen in recent years as a result of the rapid growth in the number of such individuals, some of them transplant recipients on immunosuppressive regimens, many of them sufferers from AIDS.

As viruses go, cytomegalovirus has a very large genome, and its replicative cycle and, interactions with host cells are complex. Several observations suggest an important role for translational control of the production of important viral proteins (Geballe A P & Mocarski E S (1988), *J. Virology*. 62, 3334–3340; Biegalke B & Geballe A P (1990) *Virology* 177, 657–667; Schleiss et al., (1991), *J. Virology* 65, 6782–6789). Thus, several cytomegalovirus proteins, including the glycoprotein gp48, are not synthesized efficiently until late in infection, although their mRNAs accumulate at earlier stages. Further investigations revealed an unusual cis-acting sequence in the 5'-UTR of gp48 that inhibits downstream translation in transfection assays and may mediate regulation of gp48 translation during infection, possibly be delaying such translation until conditions for it are most favorable. An essential element of the cis-acting sequence is an upstream open-reading frame in the 5'-UTR, that is, a short coding sequence beginning with an AUG that is not the initiator AUG for the gp48 protein. Further evidence suggests that a cellular factor may be activated during cytomegalovirus infection and alleviate the inhibitory effects of the upstream open-reading frame. The latter may thus represent another viral nucleic acid sequence which at the correct stage of the viral replicative cycle is responsible for preferential translation of a viral RNA.

IRES elements and the influenza virus 5'-UTR are discussed in detail herein but are only examples of a broader class of viral nucleic acid sequences responsible for preferential translation of viral RNA over host RNA. The present invention applies equally well to other viral nucleic acid sequences within this broad class. A variety of procedures are available to those skilled in the art which enables them to identify other such viral nucleic acid sequences and to design methods for selecting agents which can prevent these sequences from mediating preferential translation of viral RNAs. In general, the steps involved include: to ascertain whether viral RNAs are being preferentially translated during infection by a given virus; to determine whether specific viral nucleic acid sequence(s) mediate the preferential translation; to identify other cellular and/or viral components involved; to characterize the interaction between the viral nucleic acid sequence(s) and these components; and to design a screening method in which disruption or moderation of the effect of the viral nucleic acid sequence(s) can be detected. Not all of these steps may be required, and the steps may be performed in any order depending on the nature of the results obtained. The specific details of these steps now follow. Many of the procedures used are collected in such reference texts as Ausubel F et al. (eds) *Current Protocols in Molecular Biology*, Wiley-Interscience, New York, 1991, and Sambrook et al., *Molecular Cloning: A Laboratory Manual* (2nd Ed.), Cold Spring Harbor Laboratory Press, Cold Spring Harbor, N.Y., 1989.

Preferentially Translated Viral RNAs

Several methods can be used to determine whether viral RNAs are preferentially translated during infection by a particular virus. One approach is to incubate uninfected and infected cells in the presence of a labeled amino acid, and to examine the labeled proteins synthesized in the two different types, of cell. The labeled amino acid may typically be one that includes a radioactive isotope, such as [$^{35}$S]methionine, [$^{35}$S]cysteine, [$^{3}$H]leucine, or [$^{14}$C]leucine. As an alternative to incubating intact cells with radiolabeled substrates, extracts can be made from uninfected and infectel cells and utilized in in vitro translations with these substrates, examining the translation of endogenous mRNAs or test mRNAs added to the cell extracts. A test viral RNA and a test cellular mRNA can for example be added to extracts made from either uninfected or infected cells and the translation of each type of RNA in each type of extract be studied.

Whether the experiments are performed in cells or in cell extracts, uptake of the labeled precursor into protein may be followed by measuring the incorporation of label into trichloroacetic-acid-precipitable protein. The types and relative quantities of proteins synthesized can also be assessed by using polyacrylamide gel electrophoresis to separate these proteins. The separated proteins can be detected by autoradiography or by fluorography, for example with a Phosphor Imager™ device, and analyzed by comparison with standard labeled proteins of known molecular weights included on the same polyacrylamide gel during electrophoresis. Viral proteins can be recognized in this analysis from a knowledge of their molecular weights. If these are not known, it may be possible to infer which of the proteins observed are viral proteins from the pattern of bands on the gels from uninfected and infected cells (or cell extracts): bands which are absent in the pattern from uninfected cells but significant in the pattern from infected cells are likely to represent viral proteins. Indeed, significant changes in band pattern are usually strongly indicative of the preferential translation of viral RNAs.

Viral proteins in electrophoresis gels can also be identified by other means, for example by Western blotting. This involves transferring the band pattern from the electrophoresis gel to a solid support and then exposing the transferred pattern to an antibody or antibodies specific for a viral protein or proteins, detecting bound antibody with any of several antibody-detecting procedures known to those skilled in the art. By performing a parallel Western blot using an antibody or antibodies specific for a known cellular protein or proteins, it is possible to compare the synthesis of viral and cellular proteins in uninfected and infected cells. If viral proteins are synthesized in significantly greater quantity than cellular proteins in infected cells, and/or if any or many or all cellular proteins are synthesized in reduced quantities in infected cells compared with uninfected cells, this indicates preferential translation of viral RNAs.

In an alternative approach using antibodies, antibodies specific for viral and cellular proteins can be used to immunoprecipitate or otherwise separate their respective antigens prior to electrophoresis or a quantitative measurement such as measurement, of incorporated radioactivity or enzyme activity or binding activity or agglutination activity can be used. Such determinations are informative to establish whether preferential translation of viral RNAs is occurring in infected cells.

The functions of viral and cellular proteins can also be assayed without prior immunoseparation of these proteins. The concentrations of such proteins can also be determined by immunoassays or other competitive binding assays.

Another approach to identifying whether viral RNAs are preferentially translated in infected cells is to perform what is known as a transfection-infection assay. In an assay of this sort, a gene or complementary DNA (cDNA) which encodes a protein capable of being assayed or detected is introduced into a cell by transfection, and the cell is also infected with the virus under study. In some assays the transfected gene is a cellular gene or cDNA whose transcription will provide an mRNA containing normal cellular translation sequences such as 5'- and 3'-untranslated leaders and a poly(A) tail. In other assays the transfected gene is a viral gene or cDNA whose transcription or replication will provide an RNA containing normal viral translation sequences. If the protein encoded by the transfected viral gene is produced in greater quantities in infected cells than the protein encoded by the transfected,cellular gene, relative to the amounts of these proteins produced in uninfected cells, this indicates preferential translation of viral RNAs in infected cells. It is also possible to perform these assays by transfecting both the cellular and the viral genes into the same cell and infecting this cell with the virus under study.

It will be evident to one skilled in the art that transfection-infection assays can be replaced by similar assays in which stable cell lines are used which express cellular or viral reporter gene constructs. Such cell lines can be developed using selectable marker genes such as neo. With such a cell line the transfection step would be eliminated, and assays would simply involve infection of the stable cell line with the virus.

Examination of the RNAs present in uninfected and infected cells may also for it a part of any investigation into whether viral RNAs are being preferentially translated. The presence and relative concentrations of viral and cellular RNAs can be studied by a variety of procedures known to those skilled in the art, such as Northern blot hybridizations, nuclease protection assays, primer extension reactions, and the like.

Specific Viral Nucleic Acid Sequences Mediating Preferential Translation

Various approaches are available to determine whether specific viral nucleic acid sequences are responsible for the preferential translation of viral RNAs. These include, but are not limited to, studies with chimeric RNAs having a detectable reporter polypeptide translationally linked to a viral nucleic acid sequence potentially responsible for the preferential translation; studies of naturally occurring and laboratory mutants of viral nucleic acid sequences; and transfection-infection assays.

A fruitful initial approach is often to construct chimeric RNAs having the coding sequence for a detectable reporter polypeptide linked to a viral nucleic acid sequence potentially responsible for the preferential translation of viral RNAs. Production of the detectable reporter polypeptide is then examined in translation conditions under which this reporter will not be produced unless the viral nucleic acid sequences ensure its translation. As a control, production of the detectable reporter polypeptide will also be examined under the same translation conditions from parallel constructs in which the reporter is not linked to the viral nucleic acid sequences under test. As an additional control, the chimeric RNA, or alternatively a second RNA added to each test, may include the coding sequence for a second detectable reporter polypeptide distinguishable from the first and translationally linked to RNA sequences responsible for ensuring normal translation of cellular mRNAs.

In some cases the translation conditions used for the test will be the translation conditions present in infected cells. In such cases the test can be performed by introducing the chimeric RNA or a DNA sequence encoding it into cells which previously, concurrently or subsequently are also infected with the virus under study. The transfection-infection assay described in more detail below is an example of such a test. As an alternative to performing the test in intact cells, the translation conditions present in infected cells can be reproduced in vitro by preparing extracts from infected cells and adding these to, or using them for, in vitro translations of the chimeric RNAs.

In other cases it may not be necessary to work with infected cells or extracts made from them. In some cases the chimeric RNA can be constructed in such as way that there will be limited or no production of the detectable reporter polypeptide in uninfected cells or in vitro translation extracts from such cells unless the test sequence linked to the coding sequence for the reporter allows preferential translation of the reporter. An example would be a chimeric RNA in which production of the detectable reporter polypeptide requires initiation of translation at an internal site within the RNA. In other cases it may be possible to add an inhibitor to uninfected cells or extracts made from them which blocks a step or pathway normally blocked during viral infection. An example would be the addition of cap analogs to inhibit cap-dependent initiation of translation.

Detectable reporter polypeptides suitable for use in chimeric RNAs or control RNAs include, but are not limited to, easily assayed enzymes such as β-galactosidase, luciferase, β-glucuronidase, chloramphenicol acetyl transferase, and secreted embryonic alkaline phosphatase; proteins for which immunoassays are readily available such as hormones and cytokines; proteins which confer a selective growth advantage on cells such as adenosine deaminase, aminoglycoside phosphotransferase (the product of the neo gene), dihydrofolate reductase, hygromycin-B-phosphotransferase, thymidine kinase (when used with HAT medium), xanthine-guanine phosphoribosyltransferase (XGPRT), and proteins which provide a biosynthetic capability missing from an auxotroph; proteins which confer a growth disadvantage on cells, for example enzymes that convert non-toxic substrates to toxic products such as thymidine kinase (when used with medium containing bromodeoxyuridine) and orotidine-5'-phosphate decarboxylase (when used with 5-fluoroorotic acid); and proteins which are toxic such as ricin, cholera toxin or diphtheria toxin.

Viral nucleic acid sequences responsible for preferential translation of viral RNAs can also be identified by studies of naturally occurring and laboratory mutants. The latter may be constructed by a variety of procedures known to those skilled in the art, including but not limited to chemical treatment with mutagens, and the use of molecular biology techniques to generate insertions, substitutions, deletions and point mutations in viral nucleic acid sequences. The impact of various mutations on the preferential translation of viral proteins can then be assessed by the methods described above for studying such preferential translation.

In a related approach, the mutational analysis can be performed on viral nucleic acid sequences that are translationally linked to coding sequences for detectable reporter polypeptides within chimeric RNAs of the type described above. The impact of mutations within the viral nucleic acid sequences can be assessed by examining the production of the detectable reporter polypeptide under translation conditions which require a functioning viral nucleic acid sequence for the reporter to be synthesized. This approach can be particularly productive for detailed mapping and characterization of the regions within a viral nucleic acid sequence which are important for its function in ensuring preferential translation of viral RNAs.

Transfection-infection assays are another tool which can be used to identify viral nucleic acid sequences which ensure preferential translation of viral RNAs. As explained above, such assays involve the introduction into a cell by transfection of a gene or complementary DNA (cDNA) which encodes a reporter protein that can be assayed or detected, and infection of this cell with the virus under study. To use this type of assay to identify a viral nucleic acid sequence conferring preferential translation, different chimeric constructs would be made with the same reporter gene/protein. In some constructs the RNAs transcribed from this gene will contain normal cellular translation sequences, and in others they would contain viral nucleic acid sequences believed to be responsible for preferential translation of viral RNAs. If production of the reporter protein in infected cells is lower from RNAs containing cellular translation sequences than it is from RNAs containing viral nucleic acid sequences, this indicates that the viral sequences in question are capable of mediating preferential translation.

It will be evident to one skilled in the art that this type of transfection-infection assay can also be used to analyze mutations made in viral nucleic acid sequences in order to map and characterize the precise regions of these sequences responsible for mediating preferential translation.

5'-untranslated leader sequences potentially containing sequence elements useful in the practice of this invention are known for a number of viruses and viral strains, as detailed in the following publications:

Coxsackievirus
Jenkins O., 1987, *J. Gen. Virol* 68, 1835–1848
Ilzuka et al., *Virology* 156, 64.
Hughes et al., 1989, *J. Gen. Virol.* 70, 2943–2952.
Chang et al., 1989, *J. Gen. Virol.* 70, 3269–3280.
Chang et al., 1989, *J, Gen. Virol.* 70, 3269–3280.
Lindberg et al.,1987 *Virology* 156, 50.
Tracy et al., 1985 *Virus Res.* 3, 263–270.
Hepatitis A Virus
Cohen JI et al.,1987 *Proc. Natl. Acad. Sci. USA* 84, 2497–2501.
Paul et al., 1987, *Virus Res.* 8, 153–171.
Cohen et al., 1987, *J. Virol.* 61, 50–59.
Linemeyer et al.,1985 *J. Virol.* 54, 252.
Najarian et al., 1985 *Proc. Natl. Acad. Sci. USA* 82, 2627
Baroudy B M et al., 1985 *Proc. Natl. Acad. Sci. USA* 82, 2143–2147.
Poliovirus
Racaniello & Baltimore 1981 *Proc. Natl. Acad. Sci. USA* 78, 4887–4891;
Stanway G et al.,1984 *Proc. Natl. Acad. Sci. USA* 81, 1539–1543.
La Monica N et al., 1986 *J. Virology* 57, 515.
Hughes P J et al., 1986 *J. Gen. Virol.* 67, 2093–2102.
Hughes P J et al., 1988 *J. Gen. Virol.* 69, 49–58.
Ryan M D et al.,1990 J. Gen. Virol 71, 2291–2299.
Pollard et al., 1989, J. Virol.,63, 4949–4951.
Nomoto et al., 1982 *Proc. Natl. Acad. Sci. USA* 79, 5793–5797.
Toyoda et al., 1984, *J. Mol. Biol.* 174, 561–585.
Rhinovirus
Deuchler et al., 1987 *Proc. Natl. Acad. Sci. USA* 84, 2605–2609.
G. Leckie, Ph.D.thesis University of Reading, UK.
Skern T et al., 1985, *Nucleic Acids Res.* 13, 2111.
Callahan P et al., 1985 *Proc. Natl. Acad. Sci. USA* 82, 732–736.
Stanway et al.,1984 *Nucl. Acids Res.* 12, 7859–7875.
Bovine Enterovirus
Earle et al., 1988, *J. Gen. Virol.* 69, 253–263.
Foot-and Mouth Disease Virus
Forss et al., 1984, *Nucleic Acids Res.* 12, 6587.
Beck et al., 1983, *Nucleic Acids Res.* 11, 7873–7885.
Villanueva et al., 1983, *Gene* 23, 185–194.
Beck et al., 1983, *Nucleic Acids Res.* 11, 7873–7885.
Carroll A R et al., 1984 Clarke *Nucleic Acids Res.* 12, 2461.
Boothroyd et al., 1982, *Gene* 17, 153–161.
Boothroyd et al., 1981 *Nature,* 290, 800–802.
Robertson et al., 1985, *J. Virol.* 54, 651.
Wendell et al., 1985 *Proc. Natl. Acad. Sci. USA* 82, 2618–2622.
Enterovirus Type 70
Ryan, M D et al. 1989 *J. Gen. Virol.*
Theiler's Murine Encephalomyelitis Virus
Ohara et al., 1988, *Virology*164, 245.
Peaver et al., 1988, *Virology* 165, 1.
Peaver et al., 1987, *J. Virol.* 61, 1507.
Encephalomyocarditis Virus.
Palmenberg et al., 1984 *Nucl. Acids Res.* 12, 2969–2985.
Bae et al., 1989 *Virology* 170, 282–287.
Hepatitis C Virus
Inchauspe et al., 1991 *Proc. Natl. Acad. Sci. USA* 88, 10293.
Okamoto et al., 1992, v 188, 331–341
Kato et al., 1990, *Proc. Natl. Acad. Sci. USA* 87, 9524–9528
Takamizawa et al., 1991, *J. Virology* 65, 1105–1113
Okamoto et al., 1991, *J. Gen. Virol* 72, 2697–2704
Choo et al., 1991, *Proc. Natl. Acad. Sci. USA* 88, 2451–2455
Han et al., 1991 *Proc. Natl. Acad. Sci. USA* 88, 1711–1715
Influenza Virus
Fiers W et al., 1981,*J. Supramol Struct Cell Biochem* (*Suppl* 5), 357.

The sequence of the 5'-UTR is AGCAAAAG-CAGGGUAGAUAAUCACUCAC UGAGUGACAU-CAAAAUC (SEQ ID NO:18) The 12 nucleotides underlined are conserved in all influenza mRNAs. A Also known is the sequence of hepatitis B virus: Galibert et al., 1979 *Nature* 281, 646–650.

Identification of Other Components

Once a viral nucleic acid sequence has been identified as responsible for preferential translation of viral RNAs, a variety of procedures are available to identify cellular and/or viral components involved in the action of this viral nucleic acid sequence.

Proteins or other macromolecules which bind directly to this viral nucleic acid sequence are clearly of particular interest. One method to identify such proteins or macromolecules is to use gel retardation assays. In such assays, an RNA species consisting of or containing the viral nucleic acid sequence would be prepared in labeled form, for example by transcription in the presence of labeled nucleotides from an appropriate DNA constructed for the purpose. Samples of the labeled RNA would then be brought into contact with cell extracts, for example extracts made from infected and uninfected cells, and subjected to electrophoresis alongside samples of the labeled RNA which had not been placed in contact with such cell extracts. A decrease in mobility of the labeled RNA which had been in contact with cell extracts would indicate the presence in those extracts of proteins or macromolecules which bind to the RNA.

Another method to identify such proteins is UV-cross-linking. This also utilizes labeled RNA consisting of or containing the viral nucleic acid sequence of interest. The labeled RNA is first incubated with cell extracts from uninfected or infected cells, and any RNA-protein complexes which form are then cross-linked by exposure to ultraviolet light, for example light of wavelength 254 nm. RNA not involved in cross-linked complexes is removed by nuclease treatment, and the complexes are subjected to SDS-polyacrylamide gel electrophoresis followed by autoradiography or fluorography to determine the molecular weights of proteins/macromolecules involved in the complexes. The proteins which become cross-linked to labeled RNA can also be examined by immunochemical procedures such as Western blotting or immunoprecipitation.

If an antibody is made or available against a protein suspected of involvement in the action of a viral nucleic acid sequence which mediates preferential translation, evidence for the involvement of this protein can also be gained by testing the effect of this antibody on translation mediated by the viral sequence.

Another approach to identifying cellular or viral proteins which interact with a specific viral nucleic acid sequence is to prepare this sequence in labeled form and use it as a probe to screen "expression libraries" of cellular or viral genes/cDNAs. Such libraries are constructed in such a way that the protein encoded by each cloned gene or cDNA is expressed within the clone that contains it; they are often made in the Lambda gt11 vector or similar vectors. In the present case, if a clone is producing a protein which interacts with the viral nucleic acid sequence then labeled probe should adhere specifically to that clone.

Labeled viral nucleic acid sequences can also be used as probes to analyze proteins which have been separated by electrophoresis and transferred to a membrane support such as a nitrocellulose membrane. Bands to which the labeled probe adheres represent proteins capable of binding the viral nucleic acid sequences.

In a further approach, a viral nucleic acid sequence known to be responsible for mediating preferential translation can be used as an affinity ligand to separate proteins which bind to it. Thus, the viral nucleic acid sequence can be attached to a chromatography support and used to separate proteins of interest from a cell extract by affinity chromatography. Alternatively, the viral nucleic acid sequence can be labeled with a capture group enabling it to be captured from solution using an appropriate capture reagent. Proteins which bind to the viral nucleic acid sequence can then be captured along with this sequence. The capture group used to label the viral nucleic acid sequence can, for example, be biotin (in which case the capture reagent would be avidin or streptavidin) or digoxigenin (in which case the capture reagent would be an antibody specific for this hapten). Labeling of the nucleic acid with the capture group can be achieved by incorporation of label-bearing ribonucleotides during transcription of the nucleic acid from an appropriate template, or if the capture group is biotin by labeling with a photoactivable reagent such as photobiotin.

Sucrose density gradients can also be used to identify individual proteins or complexes of proteins and/or other macromolecules involved in the preferential translation of viral RNA mediated by a viral nucleic acid sequence. Thus, for example, a viral RNA can be incubated with a ribosomal salt-wash or other fraction prepared from a cell extract, and complexes detected by sedimentation on a sucrose density gradient. To determine whether such a complex is involved in preferential viral translation, it can be formed in the presence of unlabeled viral RNA, collected from the sucrose gradient, dissociated from the RNA by treatment with micrococcal nuclease, and further treated with ethyleneglycol-bis-(B-aminoethyl ether) N,N'-tetra acetic acid (EGTA) to inhibit the micrococcal nuclease. The dissociated components can then be used to supplement an in vitro translation system to determine whether they improve or enhance the translation of viral RNA under appropriate conditions.

To determine whether proteins are required for the formation of complexes so identified, the cell extract can be mixed with labeled viral RNA and the mixture treated with proteinase K immediately prior to sedimentation on the sucrose gradient. If protease-sensitive components are required for the integrity of the complex the labeled RNA in an untreated sample will sediment more quickly than the RNA in a sample treated with proteinase K before loading on the gradient.

To determine whether specific proteins such as known translation factors are involved in the formation of a complex, antibodies specific for known proteins can be added to the complex-formation mixture and their impact on complex formation examined by analysis on sucrose gradients. Other protein components of the particle can be identified by forming the complex with labeled viral RNA, sedimenting it on a sucrose gradient, collecting the radioactive fractions corresponding to the complex, cross-linking the proteins to the RNA using ultraviolet light, degrading the RNA, and separating any labeled proteins on a SDS/polyacrylamide gel. The complex may be treated with an iodination reagent prior to cross-linking to provide cross-linking sites on proteins which otherwise would not become cross-linked. As an alternative to cross-linking, it is usually possible because of the high capacity of sucrose gradients to isolate a complex in sufficient quantity to recover its protein components by precipitation with acetone or trichloroacetic acid, prior to analysis by polyacrylamide gel electrophoresis.

It is also possible that a complex formed with viral RNA will contain other nucleic acids in addition to the viral RNA used to form it. Such nucleic acid components in the complex can be detected by forming the complex with unlabeled viral RNA, collecting the fractions corresponding to the complex from a sucrose gradient, extracting them with phenol, precipitating nucleic acids with ethanol, end-labeling them at the 5'-end using [gamma-$^{32}$P]ATP or at the 3'-end using [5'-$^{32}$P]pCp or [a-$^{32}$P]ddATP, and identifying labeled nucleic acids by electrophoresis on a 10% denaturing polyacrylamide gel (for shorter molecules) and a 1% agarose gel (for longer nucleic acids). Any end-labeled nucleic acid found, other than the viral RNA, can then be sequenced by enzymatic or chemical methods.

Protein-protein interactions play an important role in the regulation of translation and in the preferential translation of viral RNAs. Proteins involved in important interactions with other proteins can be identified using a yeast genetic system known as the two-hybrid system (Fields & Song, 1989, Chien et al., 1991). This requires the availability of a gene or cDNA encoding one of the two proteins which interact with each other. In the present case this gene or cDNA can be obtained by any of the several methods described in the preceding text. This gene or cDNA would be cloned into a specific plasmid in such a way that it is expressed fused to the DNA-binding domain of a yeast transcriptional activator such as GAL4 which has two separable and functionally essential domains, one for DNA-binding and the other for transcriptional activation. In parallel, genes or cDNAs encoding putative binding partners of the known component are cloned in such a way that each putative partner is expressed fused to the transcriptional activation domain of the same DNA-binding protein. Introduction of both types of fusion into the same yeast cell results in generation of functional DNA-binding protein only if the fusion partners of the two domains of this protein interact with one another closely enough to bring together its two separately-expressed domains. Clones which produce such functional DNA-binding protein can be selected very easily by plating them on a medium which requires the yeast to produce an enzyme that is under the control of the DNA-binding protein. The gene or cDNA for the partner which binds to the previously identified component can then be recovered from yeast clones which grow on the selective medium.

The power of yeast genetics can also be harnessed in a rather different approach to identifying components which interact with viral nucleic acid sequences of interest. In this approach, a construct would be made initially in which a sequence encoding a reporter polypeptide easily detectable in yeast would be coupled to the viral sequence of interest. This construct would be introduced into a suitable yeast strain and conditions established under which the reporter polypeptide is synthesized. The yeast strain would then be subjected to mutagens, and mutants isolated in which the reporter polypeptide is no longer synthesized. Each such mutant would then be used as the host in the construction of a complete library of yeast genes, and the library would be screened to identify clones which express the reporter polypeptide because the cloned gene they contain is complementing the mutation in the mutant host strain. This cloned gene is then analyzed to determine whether it encodes a product that interacts with the viral sequence coupled to the coding sequence for the reporter polypeptide. This can be achieved, for example, by using the cloned gene to direct the synthesis of its product from a transcription or expression vector and then examining the interaction of the gene product with the viral nucleic acid sequence, for example by any of the methods described above. The cloned gene can also be used as a means to identify homologous human or viral gene(s). It can, for example, be labeled and used as a hybridization probe to screen a human or viral gene/cDNA library, or sequenced in order to provide the sequences for amplification primers which can be used to amplify the corresponding gene or mRNA from human cells or viruses or viral-infected cells by the polymerase chain reaction. Isolation of human or viral gene(s) can also be accomplished directly, by making a library of human or viral genes in the mutated yeast strain which no longer produces the reporter polypeptide, and looking for complementation of the mutation by a human or viral gene.

Reporter polypeptides suitable for use in this genetic approach include, but are not limited to, easily assayed enzymes such as β-galactosidase, luciferase, and chloramphenicol acetyl transferase; proteins for which immunoassays are readily available such as hormones and cytokines; proteins which confer a selective growth advantage on cells, and in particular proteins that provide a biosynthetic capability missing from an auxotroph, such as the products of the LEU2, URA3, HIS3 and TRP1 genes; and proteins which confer a growth disadvantage on cells, for example, enzymes that convert non-toxic substrates to toxic products, such as the URA3 gene product (orotidine-5'-phosphate decarboxylase) when supplied with 5-fluoroorotic acid.

An alternative but related approach using reporter gene constructs in yeast is to introduce defined mutations in the viral nucleic acid sequence which is translationally linked to the reporter polypeptide, such that this reporter is no longer produced in a given strain of yeast. By plating these yeast on a selective medium requiring production of the reporter polypeptide for growth, spontaneous mutants can be selected which are able to overcome the mutation within the viral nucleic acid sequence. Gene libraries can then be made from these mutant yeast using the original strain as host, and complementation used to select the genes responsible for overcoming the defect in the viral nucleic acid sequence.

Another approach to identifying cellular or viral components involved in the preferential translation of viral RNAs is to fractionate extracts from uninfected and infected cells based on their ability to inhibit or stimulate the translation in vitro of a detectable reporter polypeptide from a chimeric RNA containing the coding sequence for this reporter polypeptide linked to viral nucleic acid sequences responsible for preferential translation. Thus, extracts from uninfected and infected cells are initially added to parallel but separate in vitro translation reactions and their effects on these reactions compared. The two types of extract are then fractionated in parallel using a variety of procedures known to those skilled in the art, and corresponding fractions from the two extracts is tested in parallel for their effects on in vitro translation reactions. Fractions found to contain a translation-affecting component from one type of cell (infected or uninfected) are then fractionated further in parallel with the corresponding fractions from the other type of cell (uninfected or infected), and the new fractions obtained from this next round of fractionation are also tested in in vitro translation reactions. Repeated iterations of this fractionation and testing procedure will eventually provide a relatively purified fraction containing a component(s) involved in the preferential translation of viral RNAs.

A similar approach to fractionation can be adopted using gel retardation assays as described above rather than in vitro translations to monitor the progress of the fractionation.

Fractionation methods which can be used in this approach include, but are not limited to, centrifugation, ammonium sulfate precipitation, other differential precipitations, gel filtration, ion exchange chromatography, hydrophobic interaction chromatography, reverse phase chromatography, affinity chromatography, differential extractions, isoelectric focusing, electrophoresis, isotachophoresis, and the like.

Cellular or viral components involved in preferential translation of viral RNAs and isolated by any of the aforementioned fractionation approaches can be utilized to help clone or identify the gene(s) which code for these components. If, for example, the component isolated is a protein, its amino acid sequence or a part of that sequence can be determined by well known protein sequencing methods, and the sequence information obtained can be used to predict the sequence of oligonucleotides (which can be used as reverse transcriptase primers for cDNA synthesis or as amplification primers for the polymerase chain reaction, or as hybridization probes for screening gene/cDNA libraries). Alternatively, the isolated component can be used as an immunogen to raise antibodies against the component, which antibodies can then be used to screen cDNA expression libraries to identify clones encoding the component. Antibodies can also be raised by synthesizing a short peptide corresponding to part or all of any amino acid sequence determined from the isolated component, and using this peptide as immunogen. The peptide-induced antibodies can be used to screen cDNA expression libraries, or to affinity-purify the component in larger quantities enabling more extensive sequence determination, and thus providing more extensive information on which to base a cloning strategy.

From this description it should be evident that a wide variety of methods are available to someone skilled in the art to identify cellular or viral components which interact with a viral nucleic acid sequence responsible for preferential translation of viral RNAs.

Characterization of Interactions

Many different methods are available to characterize the interactions between cellular and/or viral components and viral nucleic acid sequences responsible for preferential translation. The methods described above for detecting these interactions can, for example, be used to analyze their susceptibility to changes in pH, ionic strength, temperature, the nature and mixture of anions and cations present, the relative concentrations of the cellular and/or viral components and the test nucleic acid, the absolute concentrations of these components and nucleic acid, the availability of cofactors, the availability of an energy source, the presence or absence of lipids, of nucleic acids, of carbohydrates, of other proteins, and/or of any other additives. Similarly, these methods can be used to examine the susceptibility of the interaction to treatment of one or more of the interacting materials with chemicals or enzymes that cause modifications. A protein found to interact with a viral nucleic acid sequence can, for example, be treated with alkylating agents, oxidizing agents, reducing agents, or other agents which cause chemical modifications, or with enzymes that phosphorylate, dephosphorylate. glycosylate, deglycosylate, add lipid side-chains, remove lipid side-chains, or cause other enzymatic modifications.

Also informative is the effects of truncations, additions, substitutions, deletions, inversions and point mutations in the viral nucleic acid sequence and/or cellular components and/or viral components which interact with it. Such structural alterations can be generated by treatment of the respective materials with cleavage enzymes such as proteases, endoribonucleases and endodeoxyribonucleases, with editing enzymes such as DNA polymerases, with joining enzymes such as RNA ligases, DNA ligases, and RNA splicing enzymes, with copying enzymes such as DNA polymerases, RNA polymerases, and reverse transcriptases, with end-specific degrading enzymes such as 5'-exonucleases, 3'-exonucleases, aminopeptidases and carboxypeptidases, with enzymes that can add extensions to ends such as terminal deoxynucleotidyl transferase and poly(A) polymerase, and so on. Alternatively, structurally altered viral nucleic acid sequences and/or viral components and/or cellular components can be generated by making appropriate alterations to cloned genes and expressing these genes in intact cells or in in vitro systems. Thus, the use of restriction enzymes, ligases, linkers, adapters, reverse transcriptases, DNA polymerases, RNA polymerases, polymerase chain reactions, site-directed mutagenesis, and randomized mutagenesis make it possible to generate an enormous spectrum of structurally altered forms of biomolecules which interact with one another. These structural alterations can then be tested in the array of methods previously described to determine whether the alterations change or abolish the interaction between different sequences and components and/or the impact of these sequences and components on translation.

The interaction between a cellular or viral protein and a viral nucleic acid sequence can also be studied using methods known as footprinting. In such methods, the nucleic acid sequence and protein are allowed to interact with one another, and a reagent capable of cleaving the nucleic acid, such as a nuclease, is then added. Regions of the nucleic acid which interact with the protein will be inaccessible to the cleavage reagent and thus protected from its action. In a typical footprinting procedure, the nucleic acid is labeled at one end with a detectable label, such as a phosphate group containing $^{32}P$, and the outcome of the procedure is assessed by denaturing the products of the cleavage reaction, subjecting them to electrophoresis in a polyacrylamide sequencing gel, and detecting them by autoradiography or fluorography. The results obtained are compared with those from a control experiment in which the labeled nucleic acid had not been subjected to interaction with the protein. In the latter case, cleavage sites should be distributed relatively evenly throughout the nucleic acid and a "ladder" of bands will be observed, each rung on the ladder representing cleavage at a particular nucleotide in the sequence of the nucleic acid. In the test sample, however, some of the potential cleavage sites should have been inaccessible to the cleavage reagent because of the binding of the protein to the viral nucleic acid, and bands corresponding to the protected sites should be missing from or under-represented in the ladder of bands. The sections of the ladder with under-represented bands can then be compared with the known sequence of the viral nucleic acid to determine which regions of this nucleic acid were interacting with the protein.

The cleavage reagents used in such procedures may be nucleases, more particularly ribonucleases when the test nucleic acid is RNA, or chemical reagents such as methylating reagents which predispose nucleotides they modify to subsequent cleavage with a second reagent, or free radicals generated by reagents such as $Fe^{2-}$ ions or the reagent known as MPE.

Interactions between viral nucleic acid sequences and cellular or viral proteins can also be studied by a procedure known as an interference assay which has some similarities to footprinting and yields similar information. This procedure utilizes a reagent which can chemically modify the nucleic acid sequence of interest so as to attach new groups, such as methyl groups, to individual nucleotides in the nucleic acid. The procedure relies upon the attachment of such a group to a specific nucleotide having two effects on that nucleotide: disruption of its ability to participate in an interaction with the test protein, and predisposition of the nucleotide to cleavage with a second reagent. To perform the procedure, the test nucleic acid sequence is end-labeled at one end and treated with the chemical modification reagent under conditions such that only one nucleotide will be modified within each nucleic acid molecule, but that the position of this modification within the length of the nucleic acid molecule will be random (subject to any specificity of the modification reagent for specific types of nucleotide, such as purines in general). The modified nucleic acid is then allowed to interact with the test protein, and protein-bound nucleic acid is separated from free nucleic acid, for example by taking advantage of the reduced mobility of protein-bound compared with free nucleic acid on electrophoresis gels. The nucleic acid associated with the test protein is then released and treated with the second reagent, which cleaves this nucleic acid at sites modified with the first modification reagent. If the latter is a reagent which methylates purine bases, for example, such as dimethyl sulfate, the cleavage can be accomplished with piperidine. The cleaved nucleic acid is then electrophoresed on a polyacrylamide sequencing gel, and the banding pattern compared with that obtained by cleavage of labeled and modified nucleic acid which was not subjected to interaction with the test protein. Bands corresponding to cleavage at nucleotides involved in the interaction with the test protein will be missing or under-represented in the pattern obtained from the test sample, because the modification carried by these nucleotides prevented or reduced their ability to form complexes with the test protein.

From this description it should be evident that a variety of methods is available to someone skilled in the art to characterize the interaction between a cellular or viral protein or component and a viral nucleic acid sequence responsible for preferential translation of viral RNAs.

Design of Methods to Screen Agents

Methods to screen agents for their ability to disrupt or moderate preferential translation of viral RNAs can be designed without detailed knowledge of the precise interaction between the viral and cellular materials involved, although such a knowledge can certainly be helpful. Many of the numerous methods described above to identify the presence of viral nucleic acid sequences which mediate preferential translation of viral RNAs, to identify cellular or other viral components involved, and to characterize the interactions between these components and the viral nucleic acid sequences, can be readily adapted to detect interference with the aforementioned interactions or with the effects of these interactions.

Thus, for example, agents can be screened for their ability to prevent or reduce the binding between a cellular and/or viral protein and a viral nucleic acid sequence as detected by a gel retardation assay. More generally, binding interactions between two or more partners can be measured in a variety of ways. One approach is to label one of the partners with an easily detectable label, place it together with the other partner(s) in conditions under which they would normally interact, perform a separation step which separates bound labeled partner from unbound labeled partner, and then measure the amount of bound labeled partner. The effect of a test agent included in the binding reaction can be determined by comparing the amount of labeled partner which binds in the presence of this agent to the amount which binds in its absence.

The separation step in this type of procedure can be accomplished in various ways. In one approach, the unlabelled partner, or one of the unlabeled partners to the interaction is immobilized on a solid phase prior to the binding reaction, and unbound labeled partner is removed after the binding reaction by washing the solid phase. Attachment of the unlabeled partner to the solid phase is accomplished in various ways known to those skilled in the art, including but not limited to chemical cross-linking, non-specific adhesion to a plastic surface, interaction with an antibody attached to the solid phase, interaction between a ligand attached to the unlabeled partner (such as biotin) and a ligand-binding protein (such as avidin or streptavidin) attached to the solid phase, and so on.

Alternatively, the separation step can be accomplished after the labeled partner had been allowed to interact with unlabeled binding partner(s) in solution. One example of such an approach is the gel retardation assay described earlier. Thus, in this case the labeled partner is an RNA species consisting of or containing the viral nucleic acid sequence of interest, and the unlabeled partner is a preparation containing cellular and/or viral protein(s) which bind (s) to this nucleic acid. The two partners is allowed to interact in solution, and any complexes of labeled RNA bound to unlabeled protein is detected by their slower mobility relative to unbound labeled RNA in electrophoresis gels. The amount of these complexes formed can be determined by quantitating the label associated with them. Test agents are judged by their ability to reduce or increase the amount of complexes formed.

Many other configurations are possible for binding assays in which the interaction between labeled and unlabeled partners occurs in solution and is followed by a separation step. In some cases size differences between the labeled partner and the unlabeled partner can be exploited. Thus, for example, the separation can be achieved by passing the products of the binding reaction through an ultrafilter whose pores allow passage of unbound labeled partner, but not of the unlabeled partner or of the labeled partner once bound to its unlabeled partner. Alternatively, the products of the binding reaction can be passed through a gel filtration matrix which separates unbound labeled partner from the unlabeled partner and from the labeled partner once bound to the unlabeled partner. This can be achieved very conveniently by choosing a gel filtration matrix whose exclusion limit is greater than the molecular size of one partner and less than the molecular size of the other; the larger partner will pass through the gel filtration set-up in the void volume, while the smaller partner is eluted significantly later.

In another type of approach, separation can be achieved using any reagent capable of capturing the unlabeled partner from solution, such as an antibody against the unlabeled partner, a ligand-binding protein which can interact with a ligand previously attached to this partner, and so on.

For any of the binding assays just described, the viral nucleic acid sequences can be provided by isolation and if necessary fragmentation and/or fractionation of natural viral nucleic acids, or by copying of such nucleic acids or fragments in vitro. A preferred route for the provision of viral RNAs is to transcribe these from cloned viral genes/cDNAs or fragments thereof, including labeled nucleotides during the transcription if the viral RNA is to be the labeled partner in the binding reaction. The cellular and/or viral components for these binding assays can be provided by preparation of extracts from uninfected and/or infected cells, by partial or complete purification of the components from such extracts, by expression of the components from cloned genes, with or without purification of these components from the cells or in vitro translation reactions in which they were expressed, and so on. Labeling of these components can be accomplished by a variety of methods, including but not limited to incorporation of labeled substrates such as radiolabeled amino acids during synthesis in cells or in vitro translation reactions, or by treatment with labeling reagents such as N-hydroxy succinimidyl esters containing biotin or other haptens or detectable ligands. Detection of the labeled partner in such assays can be accomplished by a variety of procedures known to those skilled in the art, including but not limited to autoradiography, fluorography, attachment of reporter polypeptides to ligands on one of the binding partners by means of antibodies, avidin, streptavidin or other ligand-binding proteins, and so on.

Binding assays are only one example of the types of assays which can be developed to screen agents for their ability to interfere in the interactions between cellular or viral proteins or components and viral nucleic acid sequences responsible for preferential translation of viral RNAs. In another and preferred type of assay, agents is tested to determine their impact on the translation of a detectable reporter polypeptide from an RNA in which the coding sequence for the reporter is translationally linked to a viral nucleic acid sequence responsible for preferential translation of viral RNAs. Such assays were described in some detail above. Production of the detectable reporter polypeptide is examined under translation conditions in which such production is dependent upon the viral nucleic acid sequence. As a control, the chimeric RNA or a second RNA included in each test can include the coding sequence for a second detectable reporter polypeptide distinguishable from the first and translationally linked to RNA sequences responsible for ensuring normal translation of cellular mRNAs. Test agents is examined for their ability to interfere with the production of the reporter polypeptide linked to the viral nucleic acid sequence without affecting production of the reporter polypeptide linked to cellular translation sequences.

In some cases the translation conditions used for the test can be the translation conditions present in infected cells. In such cases the tests can be performed by introducing the chimeric RNA or a DNA sequence encoding it into cells which previously, concurrently or subsequently are also infected with the virus under study. The transfection-infection assay described in more detail below is an example of such a test. As an alternative to performing the test in intact cells, the translation conditions found in infected cells can be reproduced in vitro by preparing extracts from infected cells and adding these to or using them for in vitro translations of the chimeric RNAs.

In other cases it is not necessary to work with infected cells or extracts made from them, as for example in cases where the chimeric RNA can be constructed in such a way that production of the detectable reporter polypeptide is dependent on a viral nucleic acid sequence even in uninfected cells or in vitro translation extracts from such cells. This is the case for a chimeric RNA in which production of the detectable reporter polypeptide requires initiation of translation at an internal site within the RNA. In other cases it may be possible to add an inhibitor to uninfected cells or extracts made from them which blocks a step or pathway normally blocked during viral infection. An example is the addition of cap analogs to inhibit cap-dependent initiation of translation.

Whichever approach is used, the tests can be performed in intact cells containing the chimeric RNAs, for example as the result of transcription of an appropriate DNA introduced into the cells, or by in vitro translation of these chimeric RNAs.

Detectable reporter polypeptides suitable for use in chimeric RNAs or control RNAs include, but are not limited to, easily assayed enzymes such as β-galactosidase, luciferase, β-glucuronidase, chloramphenicol acetyl transferase, and secreted embryonic alkaline phosphatase; proteins for which immunoassays are readily available such as hormones and cytokines; proteins which confer a selective growth advantage on cells such as adenosine deaminase, aminoglycoside phosphotransferase (the product of the neo gene), dihydrofolate reductase, hygromycin-B-phosphotransferase, thymidine kinase (when used with HAT medium), xanthine-guanine phosphoribosyltransferase (XGPRT), and proteins which provide a biosynthetic capability missing from an auxotroph; proteins which confer a growth disadvantage on cells, such as enzymes that convert non-toxic substrates to toxic products such as thymidine kinase (when used with medium containing bromodeoxyuridine) and orotidine-5'-phosphate decarboxylase (when used with 5-fluoroorotic acid); and proteins which are toxic such as ricin, cholera toxin or diphtheria toxin.

Transfection-infection assays can also be used to identify agents which interfere in the interactions between cellular or viral proteins or components and viral nucleic acid sequences responsible for preferential translation of viral RNAs. As described above, such assays involve the introduction into a cell by transfection of a gene or complementary DNA (cDNA) which encodes a detectable reporter polypeptide translationally linked to either a viral or a cellular translation sequence, and infection of this cell with the virus under study. Polypeptides linked to viral translation sequences are produced in greater quantities in infected cells than polypeptides linked to cellular translation sequences. Test agents can be screened for their ability to reduce or abolish this disparity without affecting the production of the reporter polypeptide linked to the cellular translation sequences.

It will be evident to one skilled in the art that transfection-infection assays can be replaced by similar assays in which stable cell lines are used which express appropriate reporter gene constructs. Such cell lines can be developed using selectable marker genes such as neo. With such a cell line the transfection step is eliminated, and assays would simply involve infection of the stable cell line with the virus.

In some cases the translation advantage conferred by a viral nucleic-acid sequence may be so significant that it is observed even without viral infection, when that sequence is introduced artificially into a cell without other viral sequences. This is evidenced by superior translation in uninfected cells of a reporter polypeptide linked to the viral nucleic acid sequence as compared to the translation of the same polypeptide linked to a cellular translation sequence. In such cases, test agents may be screened in uninfected cells by determining their ability to reduce the enhanced translation of the reporter polypeptide linked to the viral sequence.

The above descriptions are provided by way of example and in no way limit the scope of the invention. It should be apparent that one skilled in the art is able to choose from a wide variety of methods to identify viral nucleic acid sequences responsible for preferential translation of viral RNAs, to identify other cellular and viral components involved, to characterize the interactions between the various partners which enable preferential translation of viral RNAs, and to develop tests which can be used to screen agents for their ability to disrupt or abolish such interactions.

The following are examples of methods used to screen for agents that block activity of translational control elements.

Screening IRES Elements

Developing assays to screen for agents that block IRES element activity preferably requires constructing a dicistronic mRNA characterized by the presence of two different reporter genes, wherein the translation of one gene is under IRES element control and translation of the other gene is under the control of the host-cell cap structure ($m^7$GpppG) and cellular 5'-UTR sequence. Such a construct makes it possible to identify agents, using either cell-free or cell-based assays, that block IRES element activity without adversely affecting the process that cells use to initiate translation of their own mRNA. Thus, the preferred embodiment of this invention enables the user to identify agents that have the desired mechanism of action while simultaneously eliminating nonspecific and possibly toxic agents.

The reporter genes can be any genes that encode products that can be conveniently and reliably detected. Commonly used detection methods include, but are not limited to, incorporation of radioisotopes, chemiluminescence, bioluminescence, colorimetric techniques and immunological procedures. Examples of appropriate reporter genes include luciferase, chloramphenicol acetyl transferase, secreted embryonic alkaline phosphatase, β-galactosidase, and dihyrodofolate reductase. This list is merely illustrative and in no way limits the scope of the invention since other suitable reporter genes will be known by those ordinarily skilled in the art. The method(s) for detecting the reporter gene products in the assay are preferably applied directly to the reactions or cells used to screen potential drug activity but, in a lesser embodiment, can also be used in conjunction with techniques for first fractionating the reaction mixtures.

Said techniques, used either singly or in combination, may include chromatography, electrophoresis, filtration, ultrafiltration, centrifugation, precipitation, extraction, complex formation or digestion.

The dicistronic reporter gene construct can be used for either in vitro or in vivo agent screens. In the in vitro (cell-free) assay format, the dicistronic mRNA construct is encoded by a plasmid DNA molecule which directs transcription of the construct under the control of a strong promoter, exemplified by the bacteriophage T7 or SP6 promoters. When purified and transcribed in vitro with the homologous RNA polymerase (e.g. T7 or SP6) in the presence of pre-formed cap structures, the plasmid directs the synthesis of large amounts of "capped" dicistronic reporter construct that can be purified using commonly practiced techniques. This dicistronic mRNA is then used as a template in a eukaryotic in vitro translation system either purchased from a commercial supplier or prepared according to procedures available in the scientific literature.

Agents may also be tested in whole cells that contain the above dicistronic reporter construct. Said construct is modified for use in cultured eukaryotic cells by: 1) placing the transcription of the construct under the control of a strong eukaryotic viral promoter, such as SV40, CMV or other promoters commonly used by those skilled in the art; 2) including splice signals such as SV40 splice signals to ensure correct processing and transport of RNAs made in the nucleus; and 3) including a polyadenylation signal such as the SV40 signal at the 3' end of the construct so that the reporter mRNA will be synthesized as a 3' polyadenylated molecule.

A plasmid encoding the dicistronic construct can be used to establish a transient expression assay for screening agents that block IRES activity or, in the preferred embodiment, to establish a stable cell line for screening agents. The latter may be accomplished by incorporating into the plasmid harboring the dicistronic reporter gene construct any of several commonly used selectable markers, such as neo, in order to select and maintain those cells containing the assay plasmid. Alternatively, a stable cell line can be generated by co-transfecting the desired host cells with two plasmids, one containing the selectable marker and the other containing the dicistronic reporter gene construct. Selecting for cells in a co-transfection procedure that have acquired one plasmid with a selectable marker is a commonly used way known to those skilled in the art to purify cells which have taken up a second plasmid which lacks the benefit of a selectable marker.

Screening Viral 5'-UTRs

The assays to screen for agents that block 5'-UTR element activity preferably require constructing a test plasmid that directs the synthesis of 2 mRNAs each representing a different reporter gene. More specifically, the synthesis of one reporter gene is under the control of the capped viral 5'-UTR and the synthesis of the second reporter gene is under the control of the capped cellular 5'-UTR sequence. Such a construct makes it possible to identify agents, using either cell-free or cell-based assays, that block viral 5'-UTR element activity without adversely affecting the process that cells use to initiate translation of their own mRNA. Thus, the preferred embodiment of this invention enables the user to identify agents that have the desired mechanism of action while simultaneously eliminating nonspecific and possibly toxic agents from consideration.

The reporter genes can be any genes that encode products that can be conveniently and reliably detected. Commonly used detection methods include, but are not limited to, incorporation of radioisotopes, chemiluminescence, bioluminescence, colorimetric techniques and immunological procedures. Examples of appropriate reporter genes include luciferase, chloramphenicol acetyl transferase, secreted embryonic alkaline phosphatase, β-galactosidase, and dihyrodofolate reductase. This list is merely illustrative and in no way limits the scope of the invention since other suitable reporter genes will be known by those ordinarily skilled in the art. The method(s) for detecting the reporter gene products in the assay are preferably applied directly to the reactions or cells used to screen potential drug activity but, in a lesser embodiment, can also be used in conjunction with techniques for first fractionating the reaction mixtures. Said techniques, used either singly or in combination, may include chromatography, electrophoresis, filtration, ultrafiltration, centrifugation, precipitation, extraction, complex formation or digestion.

The reporter gene construct can be used for either in vitro or in vivo agent screens. In the in vitro (cell-free) assay format, a chimeric plasmid encodes each reporter gene under the control of a strong promoter, exemplified by the bacteriophage T7 or SP6 promoters. When purified and transcribed in vitro with the homologous RNA polymerase (e.g. T7 or SP6) and in the presence of pre-formed cap structures, the plasmid directs the synthesis of large amounts of "capped" reporter mRNAs that can be purified using commonly practiced techniques. The capped mRNAs encoding each reporter gene are then used as templates in a eukaryotic in vitro translation system either purchased from a commercial supplier or prepared according to procedures available in the scientific literature.

Agents may also be tested in whole cells that contain the above construct carrying two reporter genes. Said construct is modified for use in cultured eukaryotic cells by: 1) placing the transcription of the reporters under the control of strong eukaryotic viral promoters, such as SV40, CMV or other promoters commonly used by those skilled in the art; 2) including splice signals, such as SV40 splice signals, for each reporter to ensure correct processing and transport of RNAs made in the nucleus; and 3) including a polyadenylation signal, such as the SV40 signal, at the 3' end of each reporter gene so that the reporter mRNA will be synthesized as a 3' polyadenylated molecule.

The plasmid can be used to establish a transient expression assay for screening agents that block viral 5'-UTR activity or, in the preferred embodiment, to establish a stable cell line for screening agents. The latter may be accomplished by incorporating into the plasmid harboring the two reporter genes any of several commonly used selectable markers, such as neo, in order to select and maintain those cells containing the assay plasmid. Alternatively, a stable cell line can be generated by co-transfecting the desired host cells with two plasmids, one containing the selectable marker and the other containing the two reporter genes. Selecting for cells in a co-transfection procedure that have acquired one plasmid with a selectable marker is a commonly used way known to those skilled in the art to purify cells which have taken up a second plasmid which lacks the benefit of a selectable marker.

Thus, as discussed above, some viruses contain 5' untranslated regions which include sequences providing a selective translational advantage to the associated RNA. These regions can be readily identified as exemplified herein, and used in assays for detection of specific antiviral agents. The following is an example of detection of such a 5'-UTR in 'flu virus, and is not limiting in this invention.

Influenza Virus

The 'flu virus ensures selective translation of its own mRNAs by causing host protein synthesis to undergo a rapid and dramatic shutoff soon after 'flu virus infection, but with 'flu mRNAs still being translated. One mechanism used to achieve this end (at least in the case of a truncated 'flu nucleocapsid protein (NP-S)) is a specific sequence in the 5'-untranslated region (UTR) of the mRNA. Translational initiation for the 'flu mRNAs is still cap-dependent.

This sequence was identified using an assay termed a transection-infection assay. In this assay cells are transfected with cDNAs (genes) encoding a cellular protein which can be easily assayed, e.g., SEAP (secreted embryonic alkaline phosphatase), and then infected with 'flu virus. If the SEAP has a normal cellular 5'-UTR, the subsequent infection with 'flu virus leads to a significant reduction in the production of SEAP. If, however, the cellular 5'-UTR is replaced with the 5'-UTR from the 'flu mRNA encoding the NP-S protein, SEAP production continues unabated after 'flu infection. This demonstrates that the 'flu 5-UTR contains some sequence ensuring translation of mRNA which contains it. By placing progressively smaller pieces of the 'flu 5'-UTR upstream of the SEAP gene, it is evident that as few as 12 nucleotides are required to mediate the protective effect.

EXAMPLE 13

Plasmid Construction

Plasmid pNP-UTR/SEAP contains the region encoding the 5'-UTR for the nucleocapsid protein of influenza virus strain A/PR/8/34 linked to the coding sequence and 3'-untranslated region for secreted embryonic alkaline phosphatase (SEAP). The 5'-UTR of the modified influenza NP-S gene (Garfinkel and Katze, 1992) was amplified by the polymerase chain reaction, using primers that placed a Hind III site at one end of the amplified product and a Sph I site at the other. The amplified product was electrophoresed on an agarose or polyacrylamide gel, stained with ethidium bromide, visualized by ultraviolet light, then excised and purified from the gel fragment. The purified product was ligated into plasmid pBC12/CMV/SEAP (Berger et al., 1988, Gene 66, 1) which had previously been digested with Hind III and Sph I. The resulting plasmids were introduced into E. coli and clones selected which contained the desired construct. Plasmid pSEAP-UTR/NP-S contains the region encoding the 5'-UTR for the SEAP protein linked to the coding sequence and 3'-untranslated region for the influenza NP-S protein. The latter is a derivative of the nucleocapsid (NP) protein of influenza virus strain A/PR/8/34 obtained by deleting 255 nucleotides from within the NP gene (Garfinkel and Katze, 1992). The deletion creates a modified NP-S protein which can be distinguished from the native NP protein in influenza virus-infected cells. pSEAP-UTR/NP-S was prepared using the same basic outline described above for the pNP-UTR/SEAP construct, amplifying the SEAP-UTR by the polymerase chain reaction and placing it upstream of the NP-S coding sequence using appropriate restriction sites. Plasmid pSEAP-UTR/SEAP is the pBC12/CMV/SEAP of Berger et al., 1988.

EXAMPLE 14

Cells and Transfections

COS-1 cells are grown in monolayers in Dulbecco's modified Eagle's medium (DMEM) containing 10% fetal calf serum, and transfected using the DEAE-dextran/chloroquine method (Cullen, 1987, Methods Enzymol. 152, 684). Monolayers are washed once with prewarmed, serum-free DMEM. DNA is added in the same medium containing 250 μg/ml DEAE-dextran. After 2 hours incubation of the cells, chloroquine is added to a final concentration of 80 μM, and the cells incubated for a further 2 hours. The transfection mixture is then removed and replaced with a solution of 20% glycerol in HEPES-buffered saline. After 2 minutes at room temperature, the cells are washed twice with Hanks' balanced salt solution (HBSS), then incubated in DMEM containing 10% fetal calf serum at 37° C.

EXAMPLE 15

Virus Infection

The WSN strain of influenza A virus are grown in Madin-Darby bovine kidney cells and titrated by plaque assay in Madin-Darby canine kidney cells (Etkind & Krug, 1975). Monolayers of COS-1 cells are infected with influenza virus at a multiplicity of infection of approximately 50 plaque-forming units per cell. Cells transfected as described in Example 2 are infected 40 hours after transfection. In all cases control cells are mock-infected with virus buffer at the same time that test cells are infected with virus.

EXAMPLE 16

SEAP Assays

The activity of SEAP is assayed from the culture medium of cells containing the SEAP gene. Each assay is performed to measure the amount of SEAP secreted into the medium in a 30-minute period following a change of medium. Thus, to measure SEAP production at times 1 hour, 2 hours, 3 hours, 4 hours, and five hours after infection, at each time point the medium in which the cells were infected is removed by aspiration, the cells are washed two to three times gently with warm medium, and fresh serum-free medium (DMEM) is added. Incubation of the cells is continued for between 10 and 60 minutes, at which point 250 μl of medium is collected into a microcentrifuge tube and assayed for SEAP as described (Berger et al., 1988). The sample is heated to 65° C. for 5 minutes and then centrifuged in a microfuge at top speed for 2 minutes. 100 μl is removed to a fresh microcentrifuge tube, an equal volume of 2× SEAP assay buffer is added (this buffer is 20 mM L-homoarginine, 1 mM MgCl, 2 M diethanolamine pH 9.8; 1 ml is prepared fresh each time by mixing 200 μl of 100 mM L-homoarginine, 5 μl of 0.2 M $MgCl_2$, 500 μl of 2 M diethanolamine pH 9.8 which is stored in the dark, and 295 μl of $H_2O$), the sample is vortexed, and transferred to one well of a 96-well microtiter plate. The plate is incubated at 37° C. for 10 minutes, after which 20 μl of substrate solution (120 mM p-nitrophenylphosphate (Sigma, cat. no. N-2765) made up in 1× SEAP assay buffer) is added to each well and mixed with its contents by pipetting up and down. $A_{206}$ readings are taken at times zero, 30", 1', and at 1' intervals thereafter. The plate is held at 37° C. between readings. The maximum linear rate of the reaction is determined by plotting $A_{206}$ against time post-substrate addition. Depending on the experiment, the maximum rate may be reached anywhere between 2 minutes and 20 minutes after substrate addition.

EXAMPLE 17

NP-S Assays

To determine whether NP-S is being synthesized at a particular time after infection, cells are labeled by incubation for 30 minutes with [$^{35}$S]methionine (1200 μCi/ml) in methionine-free DMEM. After labeling, cells are washed with ice-cold HBSS and lyzed in lysis buffer (10 mM Tris.HCl, pH 7.5, 50 mM KCl, 2 mM $MgCl_2$, 1 mM dithiothreitol, 0.2 mM phenylmethylsulfonyl fluoride, 100 units/ml aprotinin, 1% Triton X-100). The clarified lysate is diluted in buffer A (20 mM Tris.HCl, pH 7.5, 50 mM KCl, 400 mM NaCl, 1 mM EDTA, 1 mM dithiothreitol, 0.2 mM phenylmethylsulfonyl fluoride, 100 units/ml aprotinin, 20% glycerol, 1% Triton X-100) and reacted twice, for 30 minutes each time, with protein G-agarose that has been preloaded with monoclonal antibody 4F5 (from J. Yewdell, National Institutes of Health, although equivalent antibodies are readily prepared). This antibody reacts with native NP protein but not NP-S. The lysate is then reacted with protein A-agarose that has bee preloaded with pooled monoclonal antibody against NP (from R. Webster, St. Jude Children's Research Hospital, although equivalent antibodies are readily prepared), which recognizes both NP and NP-S proteins. Precipitated products are washed four times in buffer A then three times in buffer B (10 mM Tris.HCl, pH 7.5, 100 mM KCl, 0.1 mM EDTA, 100 units/ml aprotinin, 20% glycerol), boiled in an equal volume of electrophoresis buffer, and separated by electrophoresis on a gel containing 8% polyacrylamide, 0.3% bis and 4M urea. Radiolabeled proteins are then detected by autoradiography and quantitated by laser densitometry.

EXAMPLE 18

Screening of Test Compounds

A concentrated solution of each test compound is prepared and various dilutions are made to produce test solutions at a range of different concentrations. Each test solution is then tested in the series of experiments tabulated below by introducing it into the culture medium at the time of infection, or at the equivalent time in controls for which no infection is performed:

| Experiment | Plasmid used to transfect cells | Infection | Agent |
| --- | --- | --- | --- |
| 1 | None | No | No |
| 2 | None | No | Yes |
| 3 | pNP-UTR/SEAP | No | No |
| 4 | pNP-UTR/SEAP | No | Yes |
| 5 | pNP-UTR/SEAP | Yes | No |
| 6 | pNP-UTR/SEAP | Yes | Yes |
| 7 | pSEAP-UTR/NP-S | No | No |
| 8 | pSEAP-UTR/NP-S | No | Yes |
| 9 | pSEAP-UTR/NP-S | Yes | No |
| 10 | pSEAP-UTR/NP-S | Yes | Yes |
| 11 | pSEAP-UTR/SEAP | No | No |
| 12 | pSEAP-UTR/SEAP | No | Yes |
| 13 | pSEAP-UTR/SEAP | Yes | No |
| 14 | pSEAP-UTR/SEAP | Yes | Yes |

Samples are taken at various time points after infection and assayed for SEAP and NP-S as described in examples 16 and 17.

Screening Viral uORFs

This invention also encompasses methods for identifying agents that block viral uORF activity. These methods are essentially identical to the viral uORF test systems except that they use leader sequences containing the target viral uORFs in place of the viral 5'-UTR sequences.

Libraries for screening

The assays encompassed by this invention can be used to screen agent libraries to discover novel antiviral drugs. Such libraries may comprise either collections of pure agents or collections of agent mixtures. Examples of pure agents include, but are not necessarily limited to, proteins, polypeptides, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. In the case of agent mixtures, the assays are not only used to identify those crude mixtures that possess the desired antiviral activity, but also the assays provide the means to purify the antiviral principle from the mixture for characterization and development as a therapeutic drug. In particular, the mixture so identified can be sequentially fractionated by methods commonly known to those skilled in the art which may include, but are not limited to, precipitation, centrifugation, filtration, ultrafiltration, selective digestion, extraction, chromatography, electrophoresis or complex formation Each resulting subfraction can be assayed for antiviral activity using the original assay until a pure, biologically active agent is obtained.

In preferred embodiments, the assays designed for detecting antiviral activity are used for automated, high-throughput drug discovery screens in conjunction with the above mentioned libraries. The assays are performed in any format that allows rapid preparation and processing of multiple reactions such as in, for example, multi-well plates of the 96-well variety. Stock solutions of the test agents as well as assay components are prepared manually and all subsequent pipetting, diluting, mixing, washing, incubating, sample readout and data collecting is done using commercially available robotic pipetting equipment, automated work stations, and analytical instruments for detecting the signal generated by the assay. Examples of such detectors include, but are not limited to, spectrophotomers, calorimeters, luminometers, fluorometers, and devices that measure the decay of radioisotopes.

In another embodiment, the assays may be used to screen vast libraries of random peptides or oligonucleotides produced by any of the techniques already in the public domain or otherwise known to those skilled in the art. Because of their large size, these libraries are likely sources of lead agents since they can contain from $10^7$–$10^{10}$ chemical entities. Screening libraries of this size requires allowing test agents to bind to a molecular target in vitro, trapping the resulting complex in order to identify the specific lead agents that have been bound, and then producing the lead) agents in greater quantities for further development.

In the present invention, the molecular targets of choice comprise those segments of viral RNA that insure preferential translation of viral mRNA in virus-infected cells, as well as any viral or cellular protein(s) required by the viral RNA segment for this function. Either the assay target or the library agents are immobilized on a solid support so that the complexes formed between the molecular target and putative lead agents can be trapped and conveniently separated from unbound molecules. Amplification of the lead agents can be done chemically (peptide or oligonucleotide synthesis, respectively, once the sequence of the test agent has been deduced), enzymatically (PCR amplification reactions in the case of oligonucleotides) or biologically (propagation in E. coli of bacteriophage display vectors in the case of peptides). The lead peptide or oligonucleotide agents may be ultimately developed as drugs in and of themselves, or used for structural modeling studies to develop small molecule mimics which become the final drug.

The following broadly summarizes the main screening methods useful in this portion of the invention:

I. In vitro Binding Assays

Binding assays, described below, are biochemical methods that measure the extent of interaction between any desired IRES element and viral and cellular proteins which bind to the IRES element to mediate translation under its influence. These techniques provide a basis for screening libraries of synthetic, semi-synthetic, natural products or any mixtures thereof to identify potential anti-viral compounds. Such compounds, which interact with the IRES element and/or the IRES-binding protein(s), will block the formation of the requisite complex between the IRES element and the viral or cellular protein(s) and thus will reduce or abolish IRES element activity. Compounds having such properties can be identified using a variety of in vitro binding assays. In these assays, is incubated with the IRES-binding protein and test compound under conditions previously established to allow a stable complex to form between the IRES element and the binding protein in the absence of the test compound. As described below, various methods are used to detect the extent of complex formation in the presence and absence of the test compound.

A. In vitro IRES Element Binding

In this configuration, the selected IRES-binding protein, either viral or cellular, is first immobilized on a solid support using any of the techniques commonly used by those skilled in the art. These techniques include, but are not limited to, contacting the purified binding protein with a filter material made of nitrocellulose or a small reaction vessel made of polystyrene whereupon the protein will be retained on these surfaces. In another embodiment, cell extracts or mixtures of proteins containing impure binding protein may be contacted with a solid support to which is previously bound an antibody specific for the IRES element-binding protein. The antibody traps the binding protein on the solid support such that washing the surface of the support with a buffered wash solution removes all unwanted proteins from the starting sample. Thus in one step the impure binding protein is not only purified for assay purposes, but also is immobilized and ready for use in the assay.

In order to measure the amount of complex formed between the IRES element and the binding protein, IRES element preparations are used wherein the element has been labeled in such a fashion to allow convenient and sensitive detection of the element. Routine labeling procedures may include chemical, enzymatic synthesis or biosynthesis of the IRES element in the presence of labeled precursors leading to the incorporation of the isotope throughout the IRES element. Also methods for end-labeling RNA molecules at their 5' or 3' ends with [$^{32}$P] are well-known to those skilled in the art as are methods for derivatizing the molecule with other readily detectable tags such as biotin. Whereas radio-isotopically labeled IRES elements are detected by standard methods including liquid scintillation spectrometry and radiographic imaging, immobilized IRES labeled with, for example biotin, can be detected colorimetrically or luminometrically by reacting the biotinylated molecule with a biotin-binding protein, such as streptavidin, and a second biotinylated reporter molecule, such as alkaline phosphatase or luciferase, and incubating the resulting tripartite complex in the presence of a substrate that is cleaved by the reporter molecule to form a colored or luminescent substance that can be detected spectrophotometrically or with a luminometer.

In one form of the binding assay, the materials and techniques described above are employed to directly measure complex formation between the labeled IRES element and the binding protein in the presence and absence of test compounds. More specifically, in one variation, the labeled IRES element, binding protein, and test compound are incubated in solution and the mixture is then passed through a nitrocellulose filter which retains the binding protein because of the affinity of the filter material for proteinaceous substances. Any labeled IRES element bound to the binding protein will likewise be retained by the filter as part of a binding protein-IRES element complex, whereas all unbound IRES element will pass though the filter. Aliquots of buffered wash solution may be drawn through the filter several times to thoroughly wash the filter free of unbound labeled IRES elements. Measurement of the amount of bound IRES element is achieved using any of the above detection methods. In a second variation, the binding protein is first immobilized on the surface of a solid support which is typically configured as multiple small reaction vessels (e.g. 96-well microtiter plate). A buffered solution containing the labeled IRES element and test compound is then added to the reaction vessel, incubated, and then the liquid contents of the vessel are removed, and the vessel is finally rinsed several times with a wash buffer to remove the last traces of unbound IRES element. Measurement of the amount of bound IRES element in the presence and absence of the test compounds is achieved using any of the above detection methods.

The third form of the assay differs from the first two in that the IRES element RNA is itself immobilized on a solid support, which may comprise a 96-well microtiter plate, and in this form is incubated with the labeled binding protein and test compound under conditions which allow formation of a stable complex between the IRES element and the binding protein in the absence of the test compound. The IRES RNA may be bound directly to the solid support using methods commonly known to those skilled in the art, or it may be attached to the surface with the aid of a polymeric linker which may support the IRES molecule at a distance from the surface of the support and in so doing may make the IRES RNA more accessible to binding by its recognition protein. Polymeric linkers may also comprise complementary DNA sequences linked to the solid support which bind a terminal region of the IRES RNA. For purposes of detecting the binding between the IRES RNA and its binding protein, the IRES binding-protein can be labeled using any standard method known to those skilled in the art including, but not limited to, incorporation of radioactive isotopes or modification by attachment of ligands such as biotin. The latter method enables the practitioner to detect the formation of an immobilized complex using a variety of commercially-available biotin detection systems, many of which employ a biotin-binding protein such as streptavidin which in turn traps a biotinylated reporter protein as part of the complex. The reporter protein may be an enzyme that reacts with a substrate to produce a substance that can be detected with a spectrophotometer or luminometer. In practice, the test compound and labeled binding protein are incubated with the immobilized IRES RNA on the solid support, solution containing unreacted binding protein is washed from or otherwise removed the solid support and the support is analyzed for retained binding protein. Test compounds which interfere with binding will reduce the amount of labeled binding protein retained on the support.

In a second embodiment, assays are used that indirectly measure binding between the IRES element and its binding protein in the presence and absence of test compound. In one configuration, the assay relies on the ability of the binding protein to protect the IRES element RNA from degradation by incubation with ribonucleases in vitro ("footprint" assay). More specifically, IRES elements labeled with [$^{32}$P] at either their 5' or 3' ends are incubated in solution with the purified IRES element binding protein and test compound under conditions where the IRES element and binding protein form a stable complex in the absence of the test compound. Enzymes which cleave RNA, such as ribonuclease T1 or S1, are then added to the assay mixture under predetermined conditions of temperature and concentration so as to normally cleave each RNA molecule once in a random fashion. The ribonuclease digestion is halted by quick chilling and the addition of a chaotropic agent such as urea which denatures the ribonuclease and strips bound IRES-binding protein from its RNA. The RNase reaction products (i.e., digested IRES RNA) are fractionated by polyacrylamide gel electrophoresis in the presence of urea. Cleavage of any IRES RNA not bound to and therefore unprotected by an IRES-binding protein will result in the appearance of a "ladder" of RNA fragments on the gel which are visualized by commonly used radiographic imaging methods. In contrast, the digestion pattern of an IRES element bound to an IRES-binding protein resembles a ladder with missing rungs. Potential antiviral compounds which block the interaction between the IRES element and its binding protein(s) will restore the ladder-like appearance to the digestion profile.

A second configuration of the indirect binding assay relies on the well-known ability of nucleic acid binding proteins to alter the gel electrophoretic migration of nucleic acid fragments to which they are bound. In this assay, IRES RNA labeled, for example, at the 5' or 3' end with [$^{32}$P] is incubated in solution with the IRES-binding protein and test compound under conditions which allow formation of a stable complex between the IRES element and its binding protein in the absence of test compound. The reaction mixture is then fractionated electrophoretically on a polyacrylamide gel and the position of the IRES element is visualized using routine radiographic imaging methods. An IRES element complexed with its binding protein usually migrates more slowly than an unbound IRES element because of the retarding influence of the bulky binding protein (although in some cases the complex migrates more quickly, presumably because of charge or conformation effects). Potential antiviral compounds which block the interaction between the IRES element and its binding protein(s) will confer a normal rate of migration to the IRES element. Any of the above means can be used to identify compounds in vitro which block the interaction between an IRES element and its binding protein(s), such interaction being required for IRES element translational activity both in vitro and in vivo. Compounds identified in this manner can be further screened as viral translation inhibitors in cell-free translation and whole cell assay systems.

II. Cell-Free Translation System Assays

Developing assays to screen for compounds that block IRES element activity requires constructing a mRNA molecule characterized by the presence of a reporter gene the translation of which is under IRES element control. The level of reporter gene translation is used to monitor the effect of test compounds on the activity of the controlling IRES element. Preferably, however, the diagnostic mRNA contains not one but two different reporter genes, wherein the translation of one reporter is under IRES control and translation of the other reporter is under the control of the host-cell cap structure (m$^7$GpppG) and cellular 5'-UTR sequence. Such a dicistronic construct makes it possible to use translation-based assays to identify compounds that block IRES element activity but do not adversely affect the process that cells use to initiate translation of their own mRNA. In other words, this form of the invention enables the practitioner to identify compounds that have the desired mechanism of action while simultaneously eliminating non-specific and possibly toxic compounds.

The reporter genes employed for either the monocistronic or dicistronic configurations can be any genes that encode products that can be conveniently and reliably detected. Commonly used detection methods include, but are not limited to, incorporation of radioisotopes, chemiluminescence, bioluminescence, colorimetric techniques and immunological procedures. Examples of appropriate reporter genes include luciferase, chloramphenicol acetyl transferase, secreted embryonic alkaline phosphatase, β-galactosidase, and dihyrodofolate reductase. This list is merely illustrative and in no way limits the scope of the invention since other suitable reporter genes will be known by those ordinarily skilled in the art. The method(s) for detecting the reporter gene products in the assay are preferably applied directly to the reactions or cells used to screen potential drug activity but, in a lesser embodiment, could also be used in conjunction with techniques for first fractionating the reaction mixtures. Said techniques, used either singly or in combination, may include chromatography, electrophoresis, filtration, ultrafiltration, centrifugation, precipitation, extraction, complex formation or digestion.

The monocistronic or dicistronic reporter gene constructs can be used for either in vitro or in vivo compound screens. In the in vitro (cell-free) assay format, the desired mRNA construct is encoded by a plasmid DNA molecule which directs transcription of the construct under the control of a strong promoter, exemplified by the bacteriophage T7 or SP6 promoters. When purified and transcribed in vitro with the homologous RNA polymerase (e.g. T7 or SP6), the plasmid directs the synthesis of large amounts of the desired reporter-containing mRNA. For the monocistronic assay this mRNA may be transcribed without a cap structure, but for the dicistronic assay, which requires that the translation of one of the reporter genes be under the control of cellular translational signals, preformed cap structures should be present during the transcription to ensure that the mRNA synthesized carries a cap-structure at the 5' end. Either the uncapped monocistronic mRNA or the capped dicistronic mRNA is then used as a template in a eukaryotic in vitro translation system purchased from a commercial supplier or prepared according to procedures available in the scientific literature. These mRNAs may be purified prior to use as translation templates but, more commonly, purification is not necessary.

III. Cellular Assays

Assays that rely on whole cells can be used as primary screens or to screen compounds that pass the in vitro binding assays and cell-free translation assays. The cells to be used are first modified either stably or transiently (e.g. transfected) with selected reporter gene constructs. Either the monocistronic or dicistronic construct described in the preceding section is modified for use in cultured eukaryotic cells by: 1) placing the transcription of the construct under the control of a strong eukaryotic viral promoter, such as SV40, CMV or other promoters commonly used by those skilled in the art, 2) including splice signals such as SV40 splice signals to ensure correct processing and transport of RNAs made in the nucleus, and 3) including a polyadenylation signal such as the SV40 signal at the 3' end of the construct so that the reporter mRNA will be synthesized as a 3' polyadenylated molecule.

A plasmid encoding the construct can be used to establish a transient expression assay for screening compounds that block IRES activity or, in the preferred embodiment, to establish a stable cell line for screening compounds. The latter may be accomplished by incorporating into the plasmid harboring the desired reporter gene construct any of several commonly used selectable markers, such as neo, in order to select and maintain those cells containing the assay plasmid. Alternatively, a stable cell line could be generated by co-transfecting the desired host cells with two plasmids, one containing the selectable marker and the other containing the dicistronic reporter gene construct. Selecting for cells in a co-transfection procedure that have acquired one plasmid with a selectable marker is a commonly used way known to those skilled in the art to purify cells which have taken up a second plasmid which lacks the benefit of a selectable marker.

Also for the stable cell line assay, a reporter gene could be chosen and used, either for the monocistronic or dicistronic construct, that confers a growth advantage to cells exposed to a test compound that inhibits IRES element activity. More specifically, the reporter gene placed under IRES element control could be a gene that encodes a product that inactivates, for example, a drug-resistance pathway in the cell or a pathway that confers resistance to any number of otherwise lethal environmental stresses (e.g. temperature, alcohol, heavy metals etc.). Cells containing this reporter gene construct grow poorly or not at all in the presence of the drug or stress, but if the same cells are treated with a test compound that inactivates the IRES element activity responsible for expression of the reporter gene, this gene product will not be made. Consequently, the pathway under its control will become active and enable the cells to grow in the presence of the environmental or drug insult.

The following examples illustrate, but in no way are intended to limit the present invention.

EXAMPLE 19
Making/Isolating IRES Element RNA Constructs
A. In Vitro Transcription Reactions Oligoribonucleotides are prepared by in vitro transcription from PCR templates amplified using a 5' primer containing a T7 promoter by procedures previously described (Milligan et al., 1987, Nucleic Acids Res. 15, 8783–8798.). RNAs are labeled by the addition of [a-$^{32}$P]-UTP (5 µCi) into the transcription reaction. Transcription reactions are purified using Stratagene NucTrap push columns and eluted with 5 mM Hepes pH 7.6, 25 mM KCl, 5 mM MgCl$_2$ and stored at −20 C.

B. PCR Reaction

Amplify selected IRES element from available plasmids using polymerase chain reaction (PCR) and primers designed to place T7 promoter on 5'end of PCR fragment. Reaction mixture contains the following: 1 µM primer #1, 1 µM primer #2, 40 µM dATP, 40 µM dGTP, 40 µM dCTP, 40 µM dTTP, 4 pg/µl template DNA, Taq DNA polymerase, 10 mM Tris-HCl pH 8.3 25° C., 40 mM KCl, 1.5 mM MgCl$_2$, and 0.01% (w/v) gelatin.

The reaction mixture (100 µl total volume) is overlaid with 100 µl mineral oil. Dip tube in mineral oil and place in heat block, forcing out air bubbles. Parameters: 94° C. 2 minutes, 42° C. 1 minute, 72° C. 1 minute, 2 sec autoextension. Remove as much oil top layer as possible. Add 100 µl TE and extract with CHCl3, then phenol/CHCl3, and finally with CHCl3. Add 30 µl 3 M NaOAc. Add 600 µl ice-cold EtOH and let stand at −20° C. for several hours. Spin 30 minutes at 14 K rpm in microfuge, then resuspend in 5 µl H$_2$O.

C. Preparation of Internally Labeled IRES RNA for Filter Binding and UV Cross-Linking Assays Reaction mixture contains the following components: 5 µl PCR fragment (5 µl) 0.1% DEPC H$_2$O (10 µl), 10 mM ATP (5 µl), 10 mM GTP (5 µl), 1 mM UTP (2.5 µl), 10 mM CTP (5 µl), [a-$^{32}$P]-NTP (100 µCi), RNasin (1 µl), and 5× buffer (10 µl; 200 mM Tris pH 8.0 37° C., 50 mM MgCl$_2$, 25 mM DTT, 1 mM spermidine, 40% PEG, 0.5% Triton X-100). The mixture is incubated at 37° C. for 5 minutes, prior to addition of 4 µl T7 polymerase (1 mg/ml). The reaction mixture is then incubated at 37° C. for 60 minutes. 2 µl RNase-free DNase is then added, and incubation continued at 37° C. for 1 minute. The reaction is then terminated by the addition of 2 µl 500 mM EDTA and extracted with phenol/CHCl$_3$. Load transcription reaction on column (Stratagene NucTrap push column with 70 µl elution buffer (5 mM Hepes pH 7.6, 25 mM KCl, 5 mM MgCl$_2$). Elute RNA from push column with 70 µl elution buffer. Determine cpm/µl with scintillation counter, and store at −20° C. Check integrity of RNA on 6% acrylamide TBE 7M urea gel.

D. Preparation of End-Labeled IRES RNA for Footprint Assay

A 500 µl T7 transcription reaction contains: PCR product (50 µl), 0.1% DEPC H$_2$O (320 µl), 100 mM ATP (5 µl), 100 mM GTP (5 µl), 100 mM UTP (5 µl), 100 mM CTP (5 µl), RNasin (5 µl), 5× buffer (100 µl: 200 mM Tris pH 8.0 37° C., 50 mM MgCl$_2$, 25 mM DTT, 5 mM spermidine, 40% PEG, 0.05% triton X-100), 5' 37° C., T7 polymerase (1 mg/ml) and 5 µl 60' 37° C. 5 µl RNase-free DNase, 37° C. 1 minute. Add 10 µl 500 mM EDTA phenol/CHCl$_3$ extract. Wash Stratagene NucTrap and push column with 70 µl elution buffer (5 mM Hepes pH 7.6, 25 mM KCl, 5 mM MgCl$_2$). Load transcription reaction on column. Elute RNA from Stratagene NucTrap, push column with 70 µl elution buffer. Add H2O to 180 µl and 20 µl 3M NaOAc pH 5.2. Add 600 µl ice-cold EtOH, then store at −20° C. overnight. Spin down 14 K rpm in microfuge at 4° C.; read A260, then determine concentration. Store at −20° C.

To 5'-end-label RNA: dephosphorylate cold RNA with calf intestine alkaline phosphatase (0.1 unit/pmol end) in 50 mM NaCl, 10 mM Tris-HCl pH 7.9 (25° C.), 10 mM MgCl$_2$, and 1 mM DTT. Incubate at 37° C. for 60 minutes. Extract with phenol/CHCl$_3$, then CHCl$_3$ and EtOH precipitate. Phosphorylate RNA with T4 polynucleotide kinase and $^{32}$P-ATP in 70 mM Tris-HCl pH 7.6 (25° C.), 10 mM MgCl2, and 5 mM DTT, 37° C. for 30 minutes. Extract with phenol/CHCl$_3$ then CHCl$_3$ EtOH precipitate, and resuspend in TE. Determine cpm/µl.

To 3'-end-label RNA: phosphorylate Cp with T4 polynucleotide kinase and $^{32}$P-ATP in 70 mM Tris-HCl pH 7.6 (25° C.), 10 mM MgCl$_2$, and 5 mM DTT, 37° C. for 30 minutes. Ligate $^{32}$P-pCp with cold RNA using T4 RNA ligase in 50 mM Tris-HCl pH 7.8 (25° C.), 10 mM MgCl$_2$, 10 mM mercaptoethanol, and 1 mM ATP, 37° C. 60 minutes. Extract with phenol/CHCl$_3$, then CHCl$_3$ EtOH precipitate, and resuspend in TE. Determine cpm/µl.

E. Construction of pBL and pBCRL Plasmids

Transcription template pBL was constructed by ligating PCR amplication products of β-globin and luciferase sequences into plasmid vector pUC19. β-globin PCR primers (SEQ. ID NO. 18, SEQ. ID NO. 19) were designed to amplify the 5' non-translated region ("NTR" also referred to as untranslated region, "UTR") of β-globin and introduce a 5' EcoR I restriction site, a 5' T7 promoter, and a 3' Kpn I restriction site. The EcoR I and Kpn I restriction sites were used for ligation into pUC19 to generate the intermediate plasmid pB. Luciferase PCR primers (SEQ. ID NO. 20, SEQ. ID NO. 21) were designed to amplify the luciferase coding sequence and introduce a 5' Pst I restriction site and a 3' Hind III restriction site, for ligation into pB to generate pBL. CAT PCR primers (SEQ. ID NO. 22, SEQ. ID NO. 23) were designed to amplify the CAT coding sequence and introduce a 5' Kpn I restriction site and a 3' Bam HI restriction site, for ligation into pBL to generate pBCL. Rhinovirus 14 5' NTR PCR primers (SEQ. ID NO. 24, SEQ.

ID NO. 25) were designed to amplify the rhinovirus 5' NTR and introduce a 5' Bam HI restrictions site and a 3' Pst I restriction site which were used to ligate the amplification product into pBCL. Rhinovirus and luciferase start codons are aligned by transforming the resultant plasmid containing β-globin 5' NTR, CAT, rhinovirus IRES and luciferase sequences into *E. coli* DMI cells. Unmethylated plasmid DNA is isolated and digested with Bcl I, the digested plasmid was religated and transformed into *E. coli* DH5 cells to produce pBCRL.

F. Ligation Reaction, Plasmid Screening, and Purification

DNA fragments were purified on low melting point agarose gels (Maniatis et al., 1989, In: Molecular Cloning: A Laboratory Manual, Cold Spring Harbor, N.Y.) and ligated with T4 DNA ligase in a 10 µl reaction in 10 mM Tris-HCl pH 7.9 (25° C.), 10 mM MgCl$_2$ 50 mM NaCl, 1 mM DTT, and incubated overnight at 16° C. Ligated plasmids are transformed into *E.coli* DH5 or DMI bacterial host cells using rubidium chloride treatment. Transformants harboring plasmid DNA were screened by ampicillin resistance and restriction analysis of minilysate plasmid DNA (Maniatis et al., 1989, In: Molecular Cloning: A Laboratory Manual, Cold Spring Harbor, N.Y.). Plasmids were sequenced in the region of interest with T7 DNA polymerase using $^{35}$S-labeled dATP.

G. Purification of DNA from LMP Agarose

Load cut DNA onto 1% LMP agarose gel in TAE with 0.5 ug/ml EtBr. Run gel slowly (25 mA for several hours) for maximum resolution and to avoid melting. Take picture and locate bands to cut out. Quickly cut out band of right size and put in Eppendorf tube. Add 10 µl 1 M Tris-HCl pH 8.0, 10 µl 8 M LiCl, bring volume to approximately 200 µl with H$_2$O. Add 200 µl phenol (not phenol/CHCl$_3$). Melt agarose 70° C. for 5 minutes. Spin 14 K rpm 5 minutes (white interphase appears). Remove aqueous phase and phenol extract again at 70° C. (clear interphase). Extract with 200 µl CHCl$_3$ twice at 25° C. Add 400 µl EtOH and keep −20° C. 1 hour. Spin down, dry pellet, dissolve in 10 µl TE. 10× TAE buffer: 24.2 g Trizma Base, 5.7 ml glacial acetic acid, 12.5 ml 0.4 M EDTA, bring up to 500 ml with H$_2$O.

H. Ligation pBLuc Construction: Ligate 0.1 ug pUC18 (digested with KpnI and SalI) with PCR1 (digested with KpnI and ApaI) and PCR2 (digested with ApaI and SalI).

pBCATIRESLuc Construction: Ligate 0.1 ug pBLuc (digested with XhoI and BclI) with PCR3 (digested with XhoI and NheI) and PCR4 (digested with NheII and BclI).

I. Transformation

Preparation of Competent Cells: Grow 5 ml of DH5 cells overnight 37° C. 2 mls overnight into 100 mls LB in 500 ml flask. Grow to OD=0.48 A600 (around 2 hours). Split into two 50 ml fractions and spin in SS34 rotor 5 minutes at 4800 rpm, 4° C. Decant supernatants and resuspend by vortexing each fraction in 16 mls Rb1. Combine tubes, then spin in SS34 rotor 10 minutes at 4800 rpm, 4° C. Decant supernatant. Gently resuspend cell pellet in 3.2 mls of Rb2 15 minutes 4° C. Quick freeze 200 µl aliquots and store −80° C.

| Rb1 | MW | for 200 mls |
|---|---|---|
| 30 mM KOAc | 98.14 | 589 mg |
| 100 mM RbCl$_2$ | 120.9 | 2.42 g |
| 10 mM CaCl$_2$—H$_2$O | 147.02 | 294 mg |
| 50 mM MnCl$_2$—4H$_2$O | 197.9 | 1.98 g |
| 15% glycerol | | 30 mls |

Adjust pH to 5.8 with 0.2 M acetic acid (5.75 mls in 500 mls). Filter sterilize.

| Rb2 | MW | for 200 mls |
|---|---|---|
| 10 mM MOPS | 209.3 | 9 mg |
| 10 mM RbCl$_2$ | 120.9 | 120 mg |
| 75 mM CaCl$_2$—H$_2$O | 147.02 | 1.1 g |
| 15% glycerol | | 30 mls |

Adjust pH to 6.5 with 1M KOH. Filter sterilize.

Transformation: 100 µl competent cells plus DNA. 30 minute 4° C. Heat shock 2 minutes 42° C. Place back on ice, and add 1 ml LB broth (best to transfer to culture tube containing 2 ml LB broth). 37° C. 1 hr with shaking plate 100 µl on selective plate. Spin down remaining cells, decant, resuspend, and plate on selective plate.

J. DNA Sequencing with USB Sequenase Kit

Extract (mini-prep) DNA from 1.5 ml overnight (or 1 ug purified DNA). Resuspend in 25 µl TE with RNase A. Put 8 µl of DNA into new tube, and add 2 µl 2M NaOH; 2 mm EDTA 5 minutes 25° C. Add 7 µl primer DNA (2 pmol/µl). Add 3 µl 2M NaOAc pH 4.6. Mix gently, then add 75 µl EtOH. 45 minutes −80° C. (overnight OK). Spin 15 minutes in microfuge. Dry pellet. Dissolve pellet in 8 µl dH$_2$O, add 9 µl sequence cocktail and incubate 2 minutes 25° C. Dispense 3.5 µl of mixture into four tubes, each containing 2.5 µl ddNTP termination mix. 15 minutes 37° C. Add 4 µl stop solution. Boil 3 minutes. Load 3 µl on 6% acrylamide, 7 M urea gel.

| Cocktail | 2 rxns-far | 3 rxns-far | 5 rxns-far | 5 rxns-close |
|---|---|---|---|---|
| seq buffer | 4 | 6 | 10 | 10 |
| 0.1 M DTT | 2 | 3 | 5 | 5 |
| dGTPlabel mix | 0.8 | 1.2 | 2 | 10 (1/20) |
| 35S-dATP | 2 | 3 | 5 | 5.0 |
| H2O | 13 | 14.4 | 26 | 12.0 |
| Sequenase ® | 0.5 | 0.8 | 1.1 | 1.1 |
| Mn buffer | | | | 5.0 |

K. Preparation of Capped RNA for Translation Reactions

T7 polymerase transcription from plasmid DNA was as follows.

A 200 µl reaction contains: 5 ug plasmid, 1 mM each NTP, 5 ug cut plasmid DNA (20 µl), 0.1% DEPC H$_2$O (128 µl), 100 mM ATP (2 µl), 10 mM GTP (2 µl), 100 mM UTP (2 µl), 10 mM m$^7$GpppG (20 µl), RNasin (1 µl), 5× plasmid buffer (40 µl), incubate 5' 37° C. Add 4 µl polymerase (2–4 µl), incubate 60' 37° C. Add 10 µl RNase-free DNase, incubate 37° C. for 1 minute. Add 5 µl 500 mM EDTA. Phenol/CHCl$_3$ extract. CHCl$_3$ extract. Add 70 µl 0.1% DEPC H$_2$O. Add 30 µl 3M NaOAc pH 5.2. 900 µl EtOH. −20° C. overnight or −80° C. 30 minutes, resuspend in 25 µl TE. Read A$_{260}$ Transcription Buffer: 200 mM Tris pH 8.0 at 37° C., 50 mM MgCl$_2$, 25 mM DTT, 5 mM spermidine, 250 ug/ml BSA, 0.1% DEPC H$_2$O (650 µl), 1M Tris (200 µl), (pH 8.0 @ 37° C., pH 8.4 @ 25° C.), 1M DTT (25 µl), 100 mM spermidine (50 µl), 10 ug/µl BSA (25 µl), 1M MgCl$_2$ (50 µl), store −20° C. (1000 µl).

L. Construction of Mono- and Dicistronic Plasmids for Transfection Assays

A dicistronic plasmid (pCMV-Luc-IRES-SEAP) is used to transfect cells and assay for translation in vivo in the presence and absense of test compounds. pCMV-Luc-IRES-SEAP contains, in order, the SV40 replication origin, cytomegalovirus (CMV) promoter, luciferase reporter gene, selected IRES element, secreted alkaline phosphatase (SEAP) reporter gene, SV40 splice sites, and SV40 polyA signal. Two pUC118-based constructs (pB-SEAP and pB-Luc-IRES-SEAP) are used to construct pCMV-Luc-IRES-SEAP. pB-SEAP contains, in order, a T7 polymerase promoter, β-globin 5' nontranslated region, and SEAP reporter gene. pB-Luc-IRES-SEAP is constructed from pB-SEAP and contains, in order, a T7 polymerase promoter, β-globin 5' nontranslated region, luciferase reporter gene, selected IRES element, and SEAP reporter gene. Construction of pB-SEAP and pB-Luc-IRES-SEAP is performed by PCR amplification of β-globin 5' NTR, luciferase coding sequence, IRES element, and SEAP coding sequence from available plasmids using primers containing unique 5' restriction sites. PCR products containing the β-globin 5'NTR and SEAP coding region are restriction digested and inserted into pUC118 to produce the monocistroic construct pB-SEAP. The dicistronic plasmid pB-Luc-IRES-SEAP is created by ligating the restriction digested monocistronic plasmid and restriction digested PCR products containing the selected IRES element and luciferase coding region. The dicistronic plasmid used to transfect cells (pCMV-Luc-IRES-SEAP) is constructed by ligating a blunt-ended Kpn I and Apa I fragment containing the LUC-IRES-SEAP coding region of pB-LUC-IRES-SEAP and Eco RV-digested plasmid vector pcDNAI-neo (InVitrogen) containing cytomegalovirus (CMV) promoter, containing SV40 replication origin, splice sites, and polyA signal.

M. PCR

Amplify T7 promoter, β-globin 5' NTR, luciferase reporter gene, IRES element, and SEAP reporter gene using polymerase chain reaction (PCR) described above and primers shown below.

| PCR Product | 5' Primer | 3' Primer | Sequence |
| --- | --- | --- | --- |
| 1 | GW2 | GW3 | T7-β-globin 5'NTR |
| 5 | GW10 | GW11 | SEAP |
| 4 | GW8 | GW9 | IRES element |
| 6 | GW12 | GW13 | luciferase |

EXAMPLE 20

Filter Binding Assays for IRES-Binding Proteins

Polypyrimidine tract binding protein (pPTB, p57; Jang and Wimmer, 1990, Genes Dev. 4, 1560–1572; Pestova et al., 1991, J. Virol. 65, 6194–6204.; Luz and Beck, 1991, J. Virol. 65, 6486–6494.; Borovjagin et al., 1990, FEBS Lett. 2, 237–240.), La (p52), eIF2/2B (Scheper et al., 1991, Biochem. Biophys. Acta 1089, 220–226.), and p70 and p100 have been identified as IRES binding proteins. Filter binding assays for pPTB have been established and are described below. Filter binding conditions for the other purified proteins must be determined. IRES elements targeted include those from rhinovirus, coxsackievirus, poliovirus, echovirus, hepatitis A virus, hepatitis B virus, hepatitis C virus, mengo virus, encephalomycarditis virus, foot and mouth disease virus, theiler's murine encephalomyelitis virus, infectious bronchitis virus, vesicular stomatitis virus, and sendai virus.

Polypyrimidine Tract Binding Protein (pPTB) is purified from E. coli as a recombinant product which contains 12 amino acids from the expression vector fused to the pPTB amino terminus. Protein-excess filter binding assays are performed as follows: typical 25 μl reactions contain $^{32}$P-internally labeled IRES element, pPTB, and MMK buffer (50 mM MES, pH 5.5, 10 mM KCl, 5 mM MgOAc) and are incubated at 25° C. for 10–30 min before filtration in the presence or absense of test compound. Reactions are filtered through Schleicher and Schuell nitrocellulose filters (0.45 μm pore size) presoaked in MMK buffer. The filters are then washed with 200 μl of MMK buffer, dried in scintillation vials for 20 min at 190° C., and counted in Econolume. All RNAs are heated to 95° C. for 3 min and quick cooled on ice just before use. Backgrounds obtained in the absence of protein are less than 5% of the input radioactivity and subtracted in all cases. Filtration assays contain $^{32}$P-labeled RNA (~10 pM) and pPTB concentrations from 5 nM to 100 nM. Retention efficiencies of the RNA range from 40% to 60%. Equilibrium binding constants vary less than a factor of two for independent replicates.

Establishment of Filter Binding Assays for Other IRES Binding Proteins

Purified La, eIF2/2B, p70, and p97 are incubated with 32P-internally labeled IRES elements under various solution conditions with pH ranges from 4–9, temperature ranges from 4–50° C., monovalent salt ($Li^+$, $Na^+$, $K^-$, $R^b+$) concentrations from 0–500 mM, divalent salt $Be^{++}$, $Mg^{++}$, $Ca^{++}$, $Ba^{++}$) concentrations from 0–50 mM, with counter anion F—, Cl—, Br—, I—, and OAc—.

EXAMPLE 21

Chemical Methods for Detecting IRES-Binding Proteins

Footprint Assays

5' or 3' end labeled RNA is incubated with purified pPTB, La, eIF2a, p70 or p97 protein under conditions which allow binding and nuclease activity. Ribonuclease T1 or S1 is added at a determined concentration, temperature, and time to give 1 hit/molecule RNA. Reactions are quenched by adding 7 M urea and quick freezing in dry ice-EtOH bath. Digested RNA fragments are separated on a 6% acrylamide, 7 M urea slab gel. Digestion in absence of protein produces a ladder of RNA digestion products; protection of RNA from nuclease by protein is observed as missing bands in ladder. Test compounds which interfere with interaction will restore ladder of RNA digestion products.

Cross-Linking Assays

Ultra-violet light cross-linking assays were performed as described previously (Jang and Wimmer, 1990, Genes Dev. 4, 1560–1572). $^{32}$P-labeled RNAs were incubated with 50 μg of HeLa extract in 30 μl of cross-link buffer (5 mM Hepes pH 7.6, 25 mM KCl, 5 mM $MgCl_2$, 3.8% glycerol) containing 1 μg rRNA at 30° C. for 20 minutes. Reactions were cross-linked in a Stratagene cross linker for 40 minutes. RNAs were digested by incubation with 20 μg RNaseA and 200 units of RNase T1. Cross-linked proteins were separated on 12.5% sodium dodecyl sulfate (SDS) polyacrylamide gels using the buffer system of Laemmli (1970, Nature 227, 680–685.), as modified by Nicklin et al., (1987, Proc. Natl. Acad. Sci. USA 84, 4002–4006.). Gels were electrophoresed at 5–10 volts/cm at constant current (70 mA), dried, and autoradiographed. The intensity of the cross-linking signal was quantitated by scanning densitometry.

EXAMPLE 22

In vitro Translation Screening Assays

Test compounds are screened for their ability to inhibit viral IRES-directed protein translation in a cell-free system containing an IRES element-protein coding region-containing construct, the selected cellular binding protein required for viral translation, and cellular translation components (ribosomes, etc.).

A. In Vitro Translation Assay

Two pUC118-based constructs (pBL and pBCRL, described above) are used to assay for translation in the presence and absense of test compounds. pBL contains, in order, a T7 polymerase promoter, β-globin 5' nontranslated region, and luciferase reporter gene. pBCRL contains, in order, a T7 polymerase promoter, β-globin 5' nontranslated region, CAT reporter gene, IRES element, and luciferase reporter gene. Test compounds are screened for their ability to inhibit luciferase synthesis driven by an IRES element using construct pBCRL, but not CAT synthesis driven by a β-globin 5'NTR using construct pBCRL and not luciferase synthesis driven by β-globin 5'NTR using construct pBL.

IRES elements targeted include those from rhinovirus, coxsackievirus, poliovirus, echovirus, hepatitis A virus, hepatitis B virus, hepatitis C virus, mengo virus, encephalomyocarditis virus, foot and mouth disease virus, theiler's murine encephalomyelitis virus, infectious bronchitis virus, vesicular stomatitis virus, and sendai virus.

B. Preparation of S10 of Hela S3 for Translation: Materials/Preparations

Rinse Type B homogenizer with EtOH and DEPC $H_2O$ in hood. Hypotonic Lysis Buffer: 0.119 g Hepes (500 µl 1M), 0.049 g KOAc (250 µl 2M), 0.016 g MgOAc (74 µl 1M), DEPC $H_2O$ to 50 mls, adjust pH to 7.4 with 1 M KOH. Add 25 µl 1 M DTT in 10 ml Hepes buffer, prepare fresh. Dialysis Buffer: 2.383 g Hepes, 8.833 g KOAc, 1.5 ml 1 M MgOAc, $H_2O$ to 1 L (non-DEPC $H_2O$ will suffice). Adjust pH to 7.4 with 1 M KOH, add 25 ml 1 M DTT in 10 ml Hepes buffer. Autoclave or filter sterilize and store 4° C. Dialysis tubing 12000–14000 cutoff. 2× Load Dye: 125 µl 1 M Tris-HCl pH 6.8, 400 µl 10% SDS, 100 µl mercaptoethanol, 375 µl 50% glycerol. Add trace bromophenolblue.

Obtain 2L HeLa S3 cells that are in log-phase (5×105 cells/ml). Wash cells 3 times with ice-cold PBS: (20 ml PBS (10 ml PBS/L cells) for 1st wash, 15 ml PBS/L cells for 2nd wash, and 10 ml PBS/L cells for 3rd wash. Spin 2 K rpm 10 minutes. Use 30 ml corex tube and HB4 rotor for third spin. Resuspend to 1.5× packed cell volume with hypotonic buffer and swell on ice 10'. Hypotonic buffer (RNase free): 10 mM K-HEPES pH 7.4 1 M stock, 10 mM KOA 4 M stock, 1.5 mM MgOAc (1 M), stock 2.5 mM DTT (add just before use). Homogenize with 15–45 strokes of type B homogenizer. Check cell disruption either visually or by dye exclusion assay after 10, 15, 20, 25 etc. strokes. If cells disrupted will see debris. Spin 5 minutes 2 K rpm (remove nuclei). Take supernate and spin 20' at 10 K rpm. Use sterile corex tubes. Dialyze 2 hours against 1 L (100 volumes) dialysis buffer (10 mM K-Hepes, pH 7.5, 90 mM KOAc, 1.5 mM MgOAc, 2.5 mM DTT) to clean and replace buffer. Add 2.5 ml 1 M DTT just before use. Freeze at −80° C. overnight, thaw at 25° C. approximately 30 minutes, immediately place on ice. Spin 10 K rpm for 10 minutes in microfuge. Add 200 µl 50% glycerol/800 µl lysate supernatant. Add 7.5 µl (2 mg/ml) micrococcal nuclease and 7.5 µl 100 mM $CaCl_2$ per 1 ml extract. Incubate 25° C. 15 minutes. Add 15 µl 200 mM EGTA/ml extract. Aliquot 150 µl/tube, store −80° C.

C. Translation Reaction

10×Translation Mix: 1 mM ATP, 50 µM GTP, 10 mM creatine phosphate, 24 µg/ml CPK, 18 mM Hepes, 2 mM DTT, 24 µg/ml tRNA, 12 µM amino acid mix, 240 µM spermidine. Aliquot and store at −80° C. Mixture contains the following: 40 µl 100 mM ATP, 6 µl 40 mM GTP, 40 µl 1 M creatine phosphate (store −20° C.), 10 µl 10 mg/ml creatine phosphokinase in Hepes (store −20° C.), 76 µl K-Hepes pH 7.6, 8 µl 1 M DTT (thaw at 37° C.), 10 µl 10 mg/ml calf liver tRNA (Boehringer), 50 µl amino acid mix-methionine, 10 µl 100 mM spermidine, and 250 µl H2O to 500 µl.

Master Mix (Prepare Fresh): Mixture contains: 150 µl micrococcal nuclease treated HeLa extract, 50 µl translation mix, 22 µl 2 M KOAc, 3 µl 50 mM MgOAc, 16 µl 20 mM MgCl2, 25 µl 35S-met (20 µCi/µl), sufficient for 28 translations, for fewer samples take less.

Translation: Mixture contains: 8.0 µl master mix, 4.5 µl 1 uM RNA in DEPC $H_2O$, +/−10 µl test compound, incubate 30° C. 3 hours. Add 40 µl 2× load dye, 28 µl $H_2O$, boil 5 minutes, load 20 µl on 12% gel, fix, enhance, expose to XRP film. Try 1M sodium salicylate 16 g/100 ml to enhance.

D. Luceriferase Assay

As described by DeWet et al., (1987, Mol. Cell Biol. 7, 725–737.). Prepare 1 mM stock solution of D-Luciferin by adding 2.8 mg luciferin (free acid—keep on ice and dark) to 9.8 ml $H_2O$, vortex to remove clumps, add 100 µl 1M $Na_2HPO4$ (gives yellow-green color, some precipitate maybe) add 100 µl 1M $NaH_2PO4$—$H_2O$ (solution clears); aliquot and store at −20° C. Prepare stock of luciferase in $H_2O$ at 1–10 mg/ml, aliquot, store −20° C. Commercial luciferase dissolved at <1 mg/ml in tricine buffer, DTT, $MgSO_4$, and 0.1% BSA, aliquot, store −20° C. Store transfected cells (not lysed) at −20° C. 100 µl lysate aliquot, store 4° C. 2–4 weeks. In vitro translation, store −20° C. To perform assays, use 350 µl assay buffer at 25° C., add 10–50 µl cold cell supernatant from 100 µl lysate, or 1–10 µl from 20 µl in vitro translation reaction. Inject 100 µl luciferin solution. Assay Buffer (use fresh): 125 µl 100 mM ATP, 75 µl 1M MgSO4, 4675 µl sonication buffer (100 mM $K_2HPO4$ [dibasic] pH 7.8, 1 mM DTT).

E. Cellular Assay

A dicistronic construct directing synthesis of two different reporter proteins is transfected into cells; cells are exposed to test compounds, then are tested for their ability to produce each of the reporter proteins. Production of both reporter proteins is visualized or detected in the same cell preferably simultaneously or alternatively sequentially. The reporter proteins may be any of luciferase, β-galactosidase, secreted embryonic alkaline phosphatase, CAT, β-glucuronidase or other suitable protein as is known in the art.

Compounds that selectively inhibit viral translation inhibit production of reporter protein 2, but not reporter protein 1; compounds that are generally toxic to cells inhibit the synthesis of reporter protein 1 and possibly reporter protein 2.

EXAMPLE 22a

Inhibiting Rhinovirus Translation with Antisense DNA Oligonucleotide Inhibitors.

The rhinovirus IRES-dependent translation system is an excellent target for antiviral compounds since it is essential for rhinovirus infection and very different than conventional human cellular translation systems. A screening assay for rhinovirus IRES-dependent translational inhibitors has been established by Applicant and the rhinovirus 14 IRES has been shown to be functional in vitro. Using this assay system, Applicant has identified antisense deoxyoligonucleotides that specifically inhibit rhinovirus IRES-dependent translation.

A. Rhinovirus Translation

Translational initiation of rhinovirus mRNA has been shown to occur by a cap-independent non-scanning mechanism, in which the 40S ribosome locates the correct start codon by binding directly to a region of the viral 5' NTR, termed the internal ribosomal entry site (IRES) (Borman and Jackson, 188 *Virology* 685, 1992). Similar IRES-dependent translational initiation mechanisms have been proposed for other picornaviruses including poliovirus (Pelletier and Sonenberg, 334 *Nature* 320, 1988, and 63 *J. Virol.* 441, 1989), EMCV (Jang et al., 62 *J. Virol.* 2636, 1988, and 63 *J. Virol.* 1651, 1989; Molla et al., 356 *Nature* 255, 1992), FMDV (Kuhn et al., 64 *J. Virol.* 4625, 1990), HAV (Brown et al., 65 *J. Virol.* 5828, 1991), and an enveloped plus-strand RNA virus, hepatitis C virus (Tsukiyama-Kohara et al., 66 *J. Virol.* 1476, 1992).

Rhinovirus belongs to the picornavirus family. The secondary structures of several picornavirus IRES elements, as well as the hepatitis C virus IRES element, have been proposed (Pilipenko et al., 168 *Virology* 201, 1989a, and 17 *Nucleic Acids Res.* 5701, 1989b; Tsukiyama-Kohara et al., 66 J. Virol. 1476, 1992). On the basis of their nucleotide sequences and proposed secondary structures, IRES elements of picornaviruses can be divided into three groups; group I belonging to the genera Enterovirus and Rhinovirus, group II belonging to the genera Cardiovirus and Aphthovirus, and group III belonging to the genus Hepatovirus of the Picornaviridae family (Jackson et al., 15 *Trends Biochem. Sci.* 477, 1990). Remarkably, the IRES elements between the three groups share little sequence or structural homology, and none of the IRES elements from the three picornavirus groups resemble the IRES element of hepatitis C virus. The boundaries of the rhinovirus 2, poliovirus 2, and EMCV IRES elements have been determined by making 5' and 3' deletions of the IRES elements and assaying for cap-independent translation (Borman and Jackson, 188 *Virology* 685, 1992; Nicholson et al., 65 *J. Virol.* 5886, 1991; Jang and Wimmer, 4 *Genes Dev.* 1560, 1990). The boundaries determined indicate that all picornavirus IRES elements are approximately 400 nucleotides ("nts") long. Although the boundaries of the rhinovirus 14 IRES have not yet been determined, by extrapolating from the above results, it is likely that the 5' border is near nt 117 and the 3' border is near nt 577 (FIG. 5).

Figure 5A:
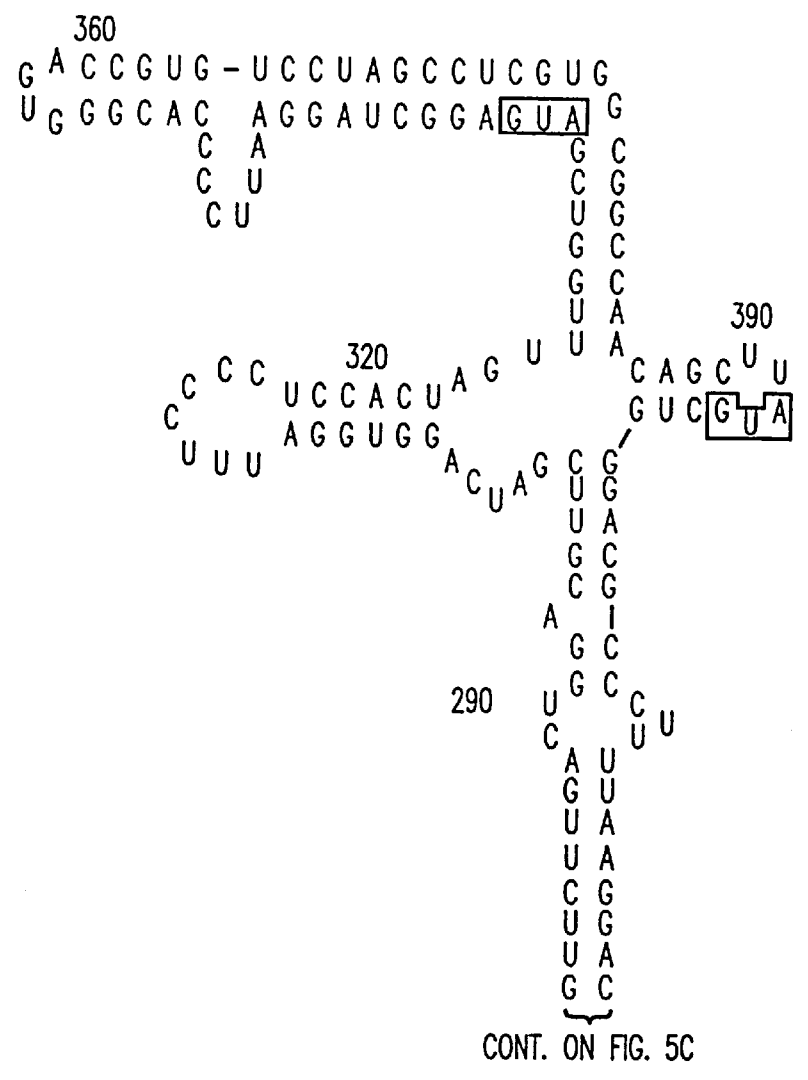
Figure 5B:
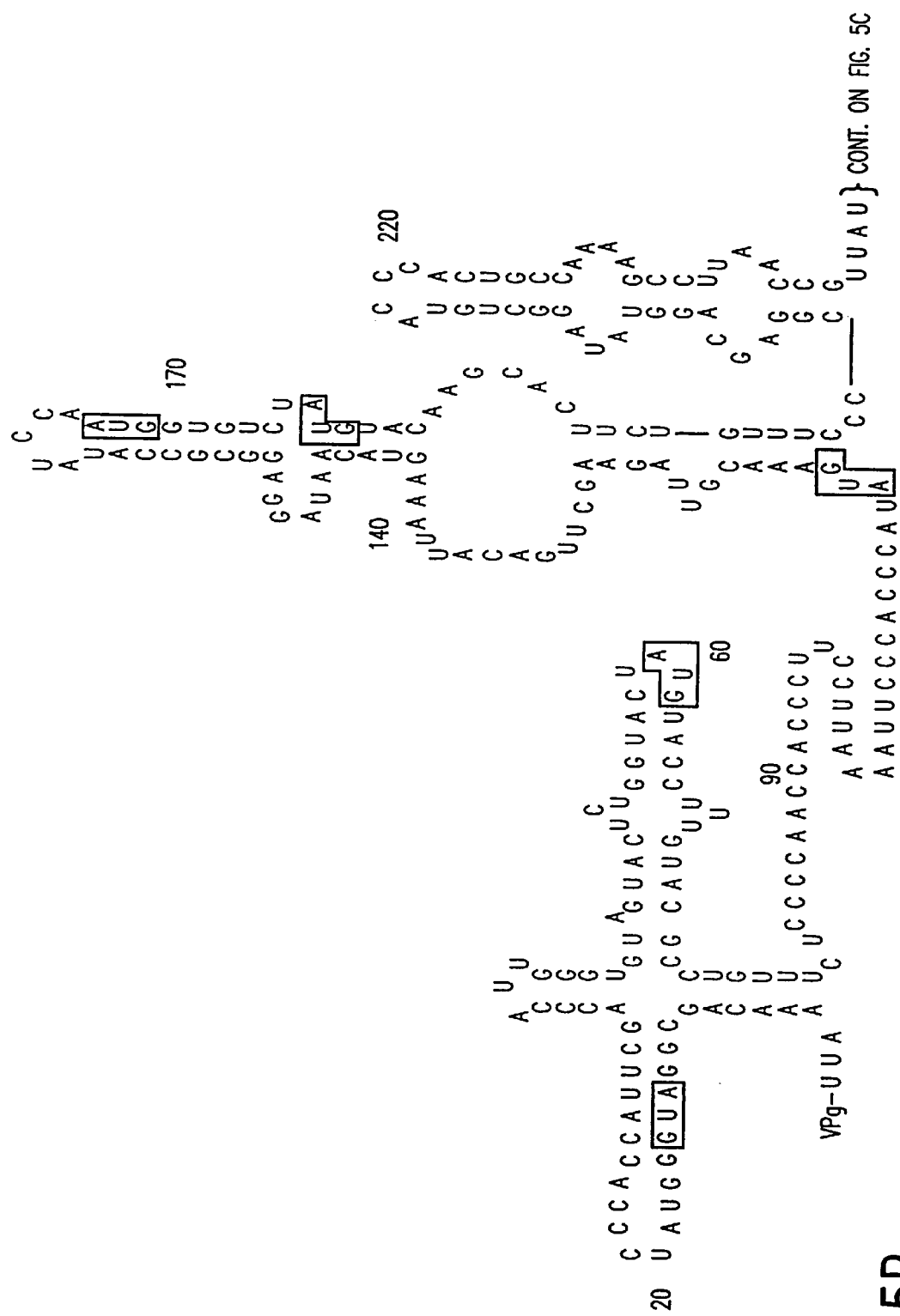
Figure 5C:
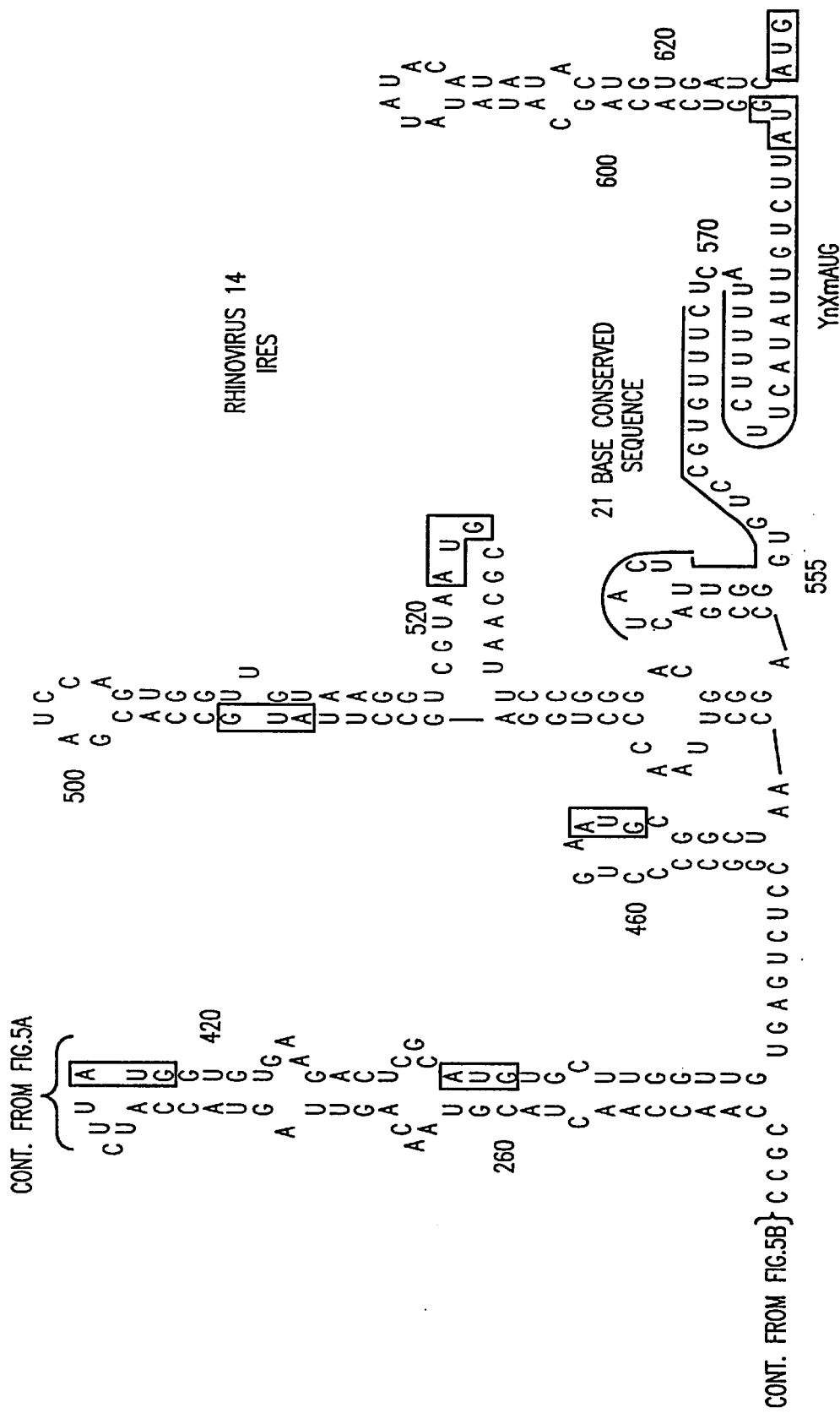

Oligopyrimidine tracts have been found near the 3' border of all picornavirus IRES elements (FIG. 5, nt 572–580). Closer inspection of the various oligopyrimidine tracts revealed the presence of a downstream AUG triplet (FIG. 5, nt 591–593). This conserved element has been termed the "$Y_nX_mAUG$" motif, with $Y_n$ corresponding to a pyrimidine tract of length n, wherein n may vary from 4 to 12 and most preferably from 5–9 nucleotides, and $X_m$ corresponding to a random spacer sequence of length m, wherein m may vary from 5 to 30 and most preferably 10–20 nucleotides (Jang et al., 44 Enzyme 292, 1990). Site directed and genetic alterations of the "$Y_nX_mAUG$" motif suggest that the sequence of the pyrimidine tract and AUG sequence are important for IRES function, as well as proper spacing between the pyrimidine tract and the AUG (Pelletier et al., 62 *J. Virol* 4486, 1988; Pestova et al., 65 *J. Virol.* 6194, 1991; Pilipenko et al., 68 *Cell* 1, 1992). The "$Y_nX_mAUG$" motif has been proposed to unify cap-independent translation among picornaviruses and may be involved in 18S ribosomal RNA binding (Jang et al., 44 *Enzyme* 292, 1990; Pilipenko et al., 68 *Cell* 1, 1992). In rhinoviruses and enteroviruses there is also a conserved 21 base sequence found upstream of the "$Y_nX_mAUG$" motif. It will be evident to one skilled in the art that in the design of an antisense oligonucleotide effective in inhibiting translation the oligonucleotide will be complementary to sequences at least partly within the IRES, and such sequences will be attractive targets for antisense oligonucleotides. The importance of this sequence in IRES-dependent translation is unknown.

The start codon used by the rhinovirus IRES element is located approximately 31 nucleotides downstream of the "$Y_nX_mAUG$" motif. It has been proposed that for rhinoviruses the ribosome binds the IRES element and then scans to the authentic start codon of the polyprotein (Jackson et al., 15 *Trends Biochem. Sci.* 477, 1990; Jang et al., 44 *Enzyme* 292, 1990).

Several cellular proteins have been observed to bind IRES elements or fragments of IRES elements (Witherell et al., 32 *Biochemistry* 8268, 1993; Borman et al., 74 *J. Gen. Virol.* 1775, 1993; Meerovitch and Sonenberg, 4 *Seminars Virol.* 217, 1993; Witherell and Wimmer, *J. Virol.*, in press 1994). For some of these proteins there is also evidence of a functional role in cap-independent translation (Jang and Wimmer, 4 *Genes Dev.* 1560, 1990; Borman et al., 74 *J. Gen. Virol.* 1775, 1993; Meerovitch et al., 67 *J. Virol.* 3798, 1993). Two cellular proteins have been found to act synergistically to stimulate cap-independent translation directed by the rhinovirus IRES element (Borman et al., 74 *J. Gen. Virol.* 1775, 1993).

B. In vitro Translation Assay

Figure 6A:
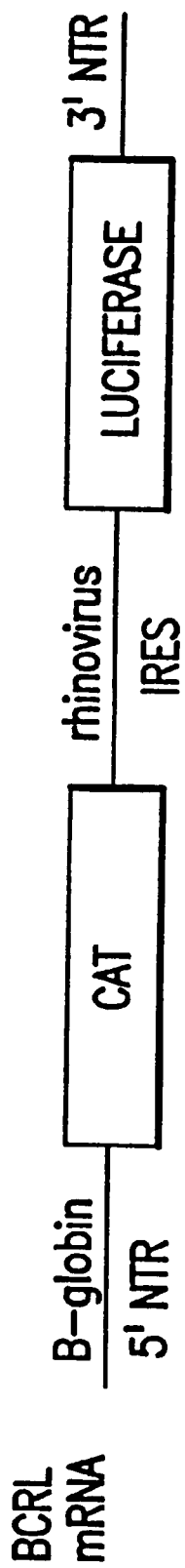
FIG. 6 shows a schematic diagram of mRNAs used for in vitro translation studies. A) bCRL mRNA containing the β-globin 5' NTR driving translation of the CAT reporter gene, and rhinovirus IRES driving translation of the luciferase reporter gene. B) bL mRNA containing the β-globin 5' NTR driving translation of the luciferase reporter gene. Lines represent β-globin 5' non-translated region (NTR), rhinovirus IRES, or 3' NTRs, as indicated. Boxes represent reporter-genes CAT (chloramphenicol acetyl transferase) and luciferase.
Figure 6B:
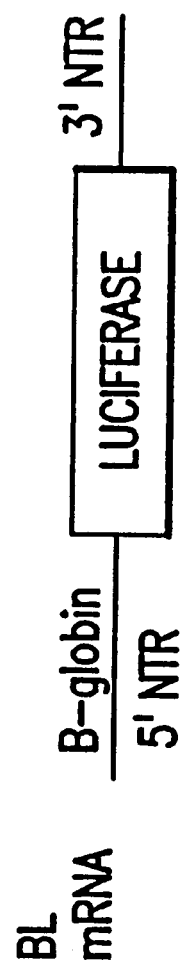

To assay translation that is dependent upon the rhinovirus IRES element in vitro, the dicistronic mRNA (bCRL) is prepared containing the β-globin 5' NTR driving translation of the CAT reporter gene and rhinovirus IRES driving translation of the luciferase reporter gene (FIG. 6A). Translational initiation of the CAT reporter in the dicistronic mRNA will be cap-dependent, whereas translational initiation of the luciferase reporter is dependent on the rhinovirus IRES. A compound that inhibits luciferase expression, without concomitant inhibition of CAT expression, indicates a selective block of IRES-dependent translational initiation. A control monocistronic mRNA is prepared (bL) containing the β-globin 5' NTR driving translation of the luciferase reporter gene (FIG. 6B). bL mRNA is used as a control to screen out compounds that inhibit luciferase activity by inhibiting translational elongation or termination of the luciferase reporter gene, shifting the ribosome out of frame, or directly inhibiting enzymatic activity of the luciferase gene product. bL and bCRL mRNAs are produced by in vitro transcription from plasmids pBL and PBCRL (not shown) using T7 RNA polymerase (Milligan et al., 15 *Nucleic Acids Res.* 8783, 1987).

There are several different ways to quantitate luciferase activity. Translation reactions can be performed in HeLa extract, or other cell lines, as described by Sonenberg and co-workers (Lee and Sonenberg, 79 *Proc. Natl. Acad. Sci. USA* 3447, 1982). Translations are performed with or without micrococcal nuclease treatment of the extracts under optimal conditions for rhinovirus IRES-dependent translation. All components of the reaction, including antisense deoxyoligonucleotides, are added to the translation reaction prior to the mRNA. No artificial annealing conditions for binding the antisense deoxyoligonucleotides and mRNA (i.e., high DNA and RNA concentrations, high salt concentrations, or heating and cooling steps) are required. An enhanced luciferase assay kit (available from Analytical Luminescence Laboratory, Promega, or other companies) is used to quantitate luciferase activity. In this assay, the translation reaction is performed in a well of the microtiter plate at 30° C. for 3 hrs. Buffer(s) from the enhanced luciferase assay kits are added, the sample mixed, and the light emitted from the reaction quantitated by a luminometer or scintillation counter. The luciferase signal from translation of mRNA is typically >10,000-fold above the background signal (-mRNA). As an alternative to a commercial luciferase assay kit, a non-enhanced assay described by DeWet et al (1987) could be used. Luciferase and CAT expression, from in vitro translation reactions with HeLa extract, can also be quantitated by a [$^{35}$S]-methionine incorporation assay. [$^{35}$S]-Methionine incorporation is measured by translating bCRL and bL mRNA in the presence of [$^{35}$S]-methionine, separating the proteins by SDS-PAGE, and visualizing the bands by autoradiography.

A transient transfection assay can also be employed using bCRL mRNA and bL mRNA or pCMV-LUC and pCMV-LUC-IRES-SEAP plasmid DNA. bCRL and bL mRNA or pCMV-LUC and pCMV-LUC-IRES-SEAP plasmid DNA is introduced into HeLa cells, or otner cell lines such as 293 or Jurkat, using lipofectin (Gibco, Inc.), electroporation, or DEAE dextran methods. Luciferase activity from in vivo translation of bCRL and bL mRNA is measured by preparing cell extracts using either the triton X-100 or freeze/thaw method and quantitating light emission. Alternatively, luciferase assays may be performed by growing transiently transfected cells in a microtiter plate and using a 1-(4,5-dimethoxy-2-nitrophenyl)diazoethane (DMNPE) caged luciferin substrate (Yang and Thomason, 15 *BioTechniques* 848, 1993). DMNPE caged luciferin is generated in a simple one-tube synthesis and requires no further purification. The caged luciferin readily crosses the cell membrane and is cleaved by endogenous esterases, trapping the luciferin substrate in the cell. Light output from the cells is proportional to luciferase expression and is quantitated with the luminometer.

Figure 7:
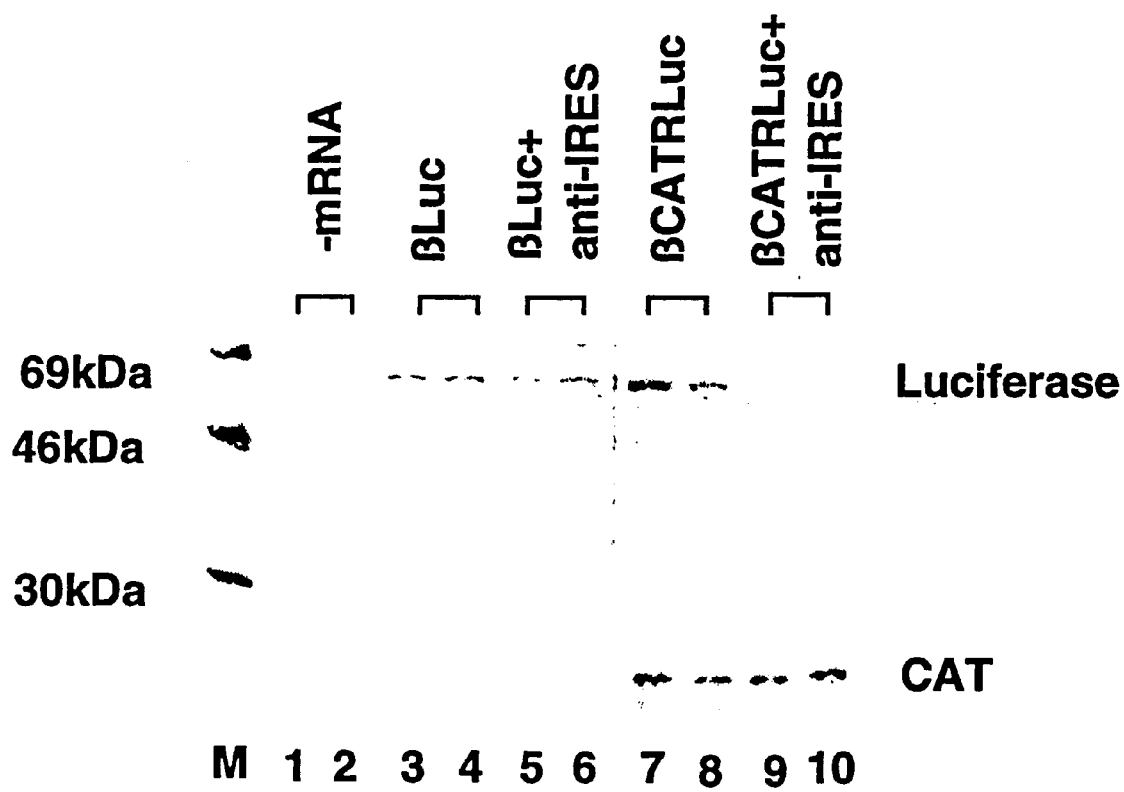
FIG. 7 shows in vitro translation of bLuc and bCRL mRNAs. Translation reactions were performed in duplicate as described by Lee, K. A. W., and Sonenberg, N. (1982) *Proc. Natl. Acad. Sci. USA* 79, 3447. Lane M, marker proteins; lanes 1–2, no mRNA; lanes 3–4, bL mRNA; lanes 5–6, bL mRNA with anti-IRES-oligo; lanes 7–8, bCRL mRNA; lanes 9–10, bCRL mRNA with anti-IRES-oligo. Bands corresponding to luciferase and CAT translation products are indicated, along with protein markers of 30, 46, and 69 kDa.

The rhinovirus 14 IRES of bCRL was shown to be functional in the HeLa extract translation system using a $^{35}$S-methionine incorporation assay. Translation of dicistronic bCRL mRNA was compared to translation of a dicistronic mRNA, bCXL, containing a reversed and complementary sequence to the rhinovirus IRES. The translation efficiency of luciferase from bCRL mRNA (driven by the rhinovirus IRES) is as great as the translation efficiency of CAT driven by the β-globin 5' NTR (FIG. 7, compare luciferase translation and CAT translation in lanes 7 and 8). Translation of luciferase from dicistronic bCXL mRNA, containing a reversed and complementary IRES, is however barely detectable. As an internal control, translation of CAT (driven by the b-globin 5' NTR) from bCXL is equivalent to translation of CAT from bCRL. Like the rhinovirus IRES element, the reversed and complementary IRES is predicted to form a high degree of secondary structure that would make scanning through this region unlikely (Jackson et al., 15 *Trends Biochem. Sci.* 477, 1990). Luciferase translation from bCRL is therefore dependent on the presence of the IRES in the correct orientation and cannot be due to RNA degradation or alternative translational initiation mechanisms such as termination-reinitiation, leaky scanning, or ribosome jumping. These results provide strong evidence that the rhinovirus IRES in bCRL is functional.

C. Antisense Oligodeoxynucleotide Results

Figure 8:
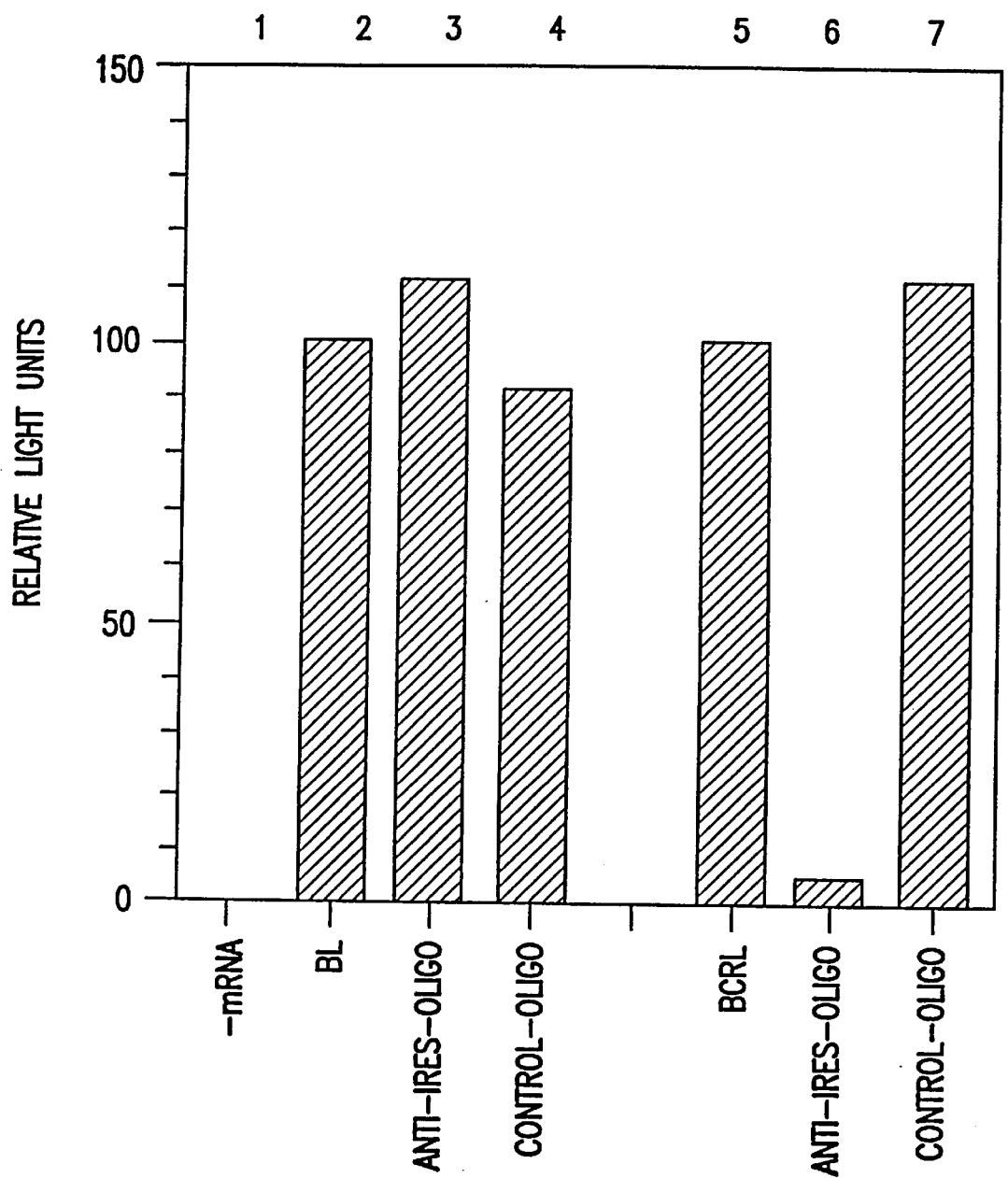
FIG. 8 shows luciferase activity assay of bL and bCRL mRNA translation reactions in the absence and presence of antisense (anti-IRES-oligo) and control (control-oligo) deoxyoligonucleotides. Translation reactions and luciferase activity assays were performed as described in text. Relative light units from two independent replicates were averaged and luciferase activity from bL and bCRL translations normalized to 100 for comparison. Translation reactions contained: lane 1, no mRNA; lane 2, bL mRNA; lane 3, bL mRNA and anti-IRES-oligo; lane 4, bL mRNA and control-oligo; lane 5, bCRL mRNA; lane 6, bCRL mRNA and anti-IRES-oligo; lane 7, bCRL mRNA and control-oligo.

Applicant has designed antisense deoxyoligonucleotides that target the 3' end of the rhinovirus IRES element and inhibit rhinovirus IRES-dependent translation. This region of the IRES was chosen since it contains both the "$Y_nX_m$ AUG" motif and the conserved 21 base sequence described above and shown in FIG. 1. Antisense deoxyoligonucleotide inhibition of the rhinovirus IRES element was assayed using the [$^{35}$S]-methionine incorporation assay (FIG. 7) and luciferase activity assay (FIG. 8). An example of an antisense oligonucleotide that targets this region is anti-IRES-oligo, which anneals to nts 518–551 of the rhinovirus 14 IRES. The sequence of anti-IRES-oligo (SEQ. ID NO. 10) is

5' AGTAGTCGGTCCCGTCCCGGAATTGCG-CATTACG 3'

Translation of monocistronic bLuc mRNA (FIG. 6A) and dicistronic bCRL mRNA (FIG. 6B) in the presence and absence of anti-IRES-oligo was determined. As expected, anti-IRES-oligo did not inhibit luciferase translation from bLuc mRNA (FIG. 7, compare luciferase translation in lanes 3–4 to lanes 5–6) or CAT from bCRL (FIG. 7, compare CAT translation in lanes 7–8 with lanes 9–10). Anti-IRES did however dramatically inhibit luciferase translation from bCRL mRNA (FIG. 7, compare luciferase translation in lanes 7–8 with lanes 9–10). Thus, anti-IRES-oligo specifically inhibits rhinovirus IRES-dependent translation. In addition, modified nucleic acid or nucleic acid analogs as defined in Example 8a may also be utilized in the method of this example.

Luciferase activity assays were performed to quantitate the translational inhibition of luciferase from bL and bCRL mRNAs by anti-IRES-oligo. In agreement with the $^{35}$S-methionine incorporation assay results, anti-IRES-oligo did not inhibit luciferase translation from bL mRNA (FIG. 8, compare lanes 2 and 3) while it inhibited luciferase translation from bCRL mRNA approximately 95% (FIG. 8, compare lanes 5 and 6). A control deoxyoligonucleotide (control-oligo, not shown) was synthesized with a reversed and complementary sequence to anti-IRES-oligo. The control deoxyoligonucleotide therefore contains approximately the same G-C and A-T composition, but cannot anneal nts 518–551 of the rhinovirus 14 IRES. Control-oligo had no effect on bL or bCRL mRNA translation (FIG. 8, compare lane 4 with lane 2 and lane 7 with lane 5). Anti-IRES-oligo thus appears to specifically inhibit translation driven by the rhinovirus IRES.

EXAMPLE 23

Reporter Gene Assays CAT Spectrophotometric Assay

The most convenient technique for quantitating the rate of CM acetylation takes advantage of the generation of a free CoA sulfhydryl group coincident with transfer of the acetyl group to CM. Reaction of the reduced CoA with 5,5'-dithiobis-2-nitrobenzoic acid (DTNB) yields the mixed disulfide of CoA and thionitrobenzoic acid and a molar equivalent of free 5-thio-2-nitrobenzoate (Habeeb). The latter has a molar extinction coefficient of 13,600 at 412 nm. The assay is best carried out with a recording spectrophotometer equipped with a temperature-controlled cuvette chamber set at 37° C.

Reagents: Tris.hydrochloride, 1.0 M, pH 7.8, acetyl-CoA, 5 mM, chloramphenicol (D-threo) 5 mM, 5,5'-Dithiobis-2-nitrobenzoic acid (DTNB). The only reagent solution that must be stored frozen in acetyl-CoA. The reaction mixture is freshly prepared from the individual reagents by dissolving 4 mg of DTNB in 1.0 ml of Tris-HCl buffer, after which 0.2 ml of the acetyl-CoA stock solution is added and the total volume is made up to 10 ml. The final concentrations of each component are as follows: Tris.HCl (100 mM), acetyl-CoA (0.1 mM), and DTNB (0.4 mg/ml). After the cuvette (1 cm light path) containing enzyme and the reaction mixture has been allowed to equilibrate with the waterbath, the reaction is started by the addition of CM at a final concentration of 0.1 mM. The rate of increase in absorption at 412 mM prior to the addition of CM is subtracted from the observed rate after the start of the reaction, and net change in extinction per minute is divided by 13.6 to give the result in micromoles per minute of CM-dependent DTNB reacted. Since the latter is equal to the rate of acetylation and since 1 unit of CAT=1 μmole of CM acetylated per minute (37° C.), the calculation also yields the number of units of enzyme in the cuvette.

An alternative spectrophotometric method can be used if a high concentration of competing mercaptans interferes with the DTNB assay. The loss of an acyl group from thioesters such as acetyl-CoA is accompanied by a decrease in absorption in the ultraviolet. The difference in molar extinction coefficients of acetyl-CoA and reduced CoA plus acetate is 4500 at 232 nm. Special care must be taken to remove interfering ultraviolet absorbing material from the enzyme preparation by gel filtration or dialysis. The contribution of the absorption due to protein added to the cuvette becomes a more serious obstacle in crude extracts, especially those with low levels of CAT activity. Apart from the inconvenience of measurements in the far ultraviolet region and the fact that the method is intrinsically less sensitive than the DTNB procedure, the assay of thioester cleavage at 232 nm suffers from being a difference method. The absolute decreases in absorbance per unit time due to the presence of CM and low levels of CAT may be impossible to quantitate without recourse to the use of a dual beam recording spectrophotometer.

Radioisotopic CAT Assay: In this assay chloramphenicol acetyl transferase (CAT) transfers the $^3$H-labeled acetyl group from acetyl CoA to chloramphenicol bound beads. The beads are washed and counted to determine CAT activity. This assay is approximately 2–5× more sensitive than the spectrophotometric assay and will detect CAT in RRL. Materials: chloramphenicol-caproate-agarose (Sigma #C8899), [$^3$H] acetyl-CoA (Amersham TRK.688; specific activity >3Ci/mmol, 250 uCi/ml), acetyl-CoA (Sigma C0378; 100 mM in 50% DMSO [25 mg in 3.1 ml]), chloramphenicol (Sigma C0378; 100 mM in 50% DMSO), CAT (Sigma C8413), 0.10XTBS (50 mM Tris-HCl (pH 7.53, 150 mM NaCl), wash buffer: TBS containing 5 mM chloramphenicol and 1% SDS. Protocol: Thoroughly resuspend beads inside bottle and pipet 5 ml into Falcon tube. Rinse pipet with 8.5 mls $H_2O$ and put in tube. Add 1.5 ml 10×TBS and spin 5 K rpm in Sorvall RC6000 rotor. Decant supernatant, refill tube with 1× TBS, respin, and decant supernatant. Add 1× TBS to 5 ml, and store excess beads at 4° C. To 100 µl rinsed beads and 2 µl substrate solution (15 mM cold acetyl COA, 0.65 mM [$^3$H] acetyl CoA), add 2 µl CAT standard (dilutions 1:2 to 1:128 in TBS) or 5 µl translation reaction and incubate 20 minutes at 25° C. Add 1.25 ml wash buffer to quench reaction, then spin in centrifuge for 5 minutes at 14 K rpm. Carefully remove supernatant, leaving some liquid on beads. Repeat wash two more times, then add 100 µl $H_2O$ and vortex. Immediately add scintillation fluid, cap, vortex upside down (to avoid clump of beads at bottom of tube which won't resuspend properly). Measure radioactivity in liquid scintillation spectrometer.

SEAP Assay: SEAP levels are determined by two distinct assays. The first assays measures the increase in light absorbance at 405 nm which accompanies the hydrolysis of p-nitrophenylphosphate (McComb and Bowers, 1972, Clin. Chem. 18, 97–104.). This assay is performed essentially as described in Example 16 above.

The bioluminescence-based assay for SEAP is performed essentially as described (Miska and Geiger, 1987, J. Clin. Chem. Clin. Biochem. 25, 23–30.). Fifty µl of freshly prepared substrate solution (0.1 mM D-luciferin-O-phosphate in LUPO buffer (10 mM diethanolamine, 0.5 mM $MgCl_2$, 10 mM L-homoarginine pH 9.8) and prewarmed to 37° C. for 5 minutes in the dark. To this is added 50 µl of heated, clarified medium, prepared as described above, or a medium sample diluted in LUPO buffer. After a 30-minute incubation at 37° C. in the dark, 100 µl of the reaction mixture are transferred into a tube containing 400 µl of bioluminescence buffer (30 mM Hepes pH 7.75, 5 mM $MgCl_2$, 0.66 mM EDTA, 0.1 mM DTT, 5 mM ATP) containing 1 µg ($10^4$ units) of luciferase. Light impulses are measured at 37° C. in a luminometer (Berthold Biolumat, Model 9500T-10-s peak-measuring mode). All the chemicals used for the SEAP assays are obtained from Sigma (St. Louis, Mo.) except for luciferase, which is obtained from Boehringer-Mannheim (Indianapolis, Ind.) and D-luciferin-O-phosphate, which can be obtained from Novabiochem AG, CH-4448, Laufelfingen, Switzerland.

EXAMPLE 24

Cellular Assays

A dicistronic construct directing synthesis of two different reporter proteins is transfected into cells; cells are exposed to test compounds, then are tested for ability to produce reporter proteins. Production of both reporter proteins is preferably simultaneously or sequentially visualized or detected in same cell (luciferase, β-galactosidase).

A. Appropriate IRES-Reporter Gene Constructs

A monocistronic plasmid (pCMV-B-SEAP) and disistronic plasmid (pCMV-Luc-IRES-SEAP) are used to transfect cells and assay for translation in vivo in the presence and absence of test compounds. pCMV-B-SEAP contains, in order, the SV40 replication origin, cytomegalovirus (CMV) promoter, β-globin 5' nontranslated region, secreted alkaline phosphatase (SEAP) reporter gene, SV40 splice sites, and SV40 polyA signal. pCMV-Luc-IRES-SEAP contains, in order, the SV40 replication origin, cytomegalovirus (CMV) promoter, β-globin 5' nontranslated region, luciferase reporter gene, selected IRES element, SEAP reporter gene, SV40 splice sites, and SV40 polyA signal.

Test compounds are screened for their ability to inhibit SEAP synthesis driven by the IRES element from pB-luc-IRES-SEAP, but not inhibit luciferase synthesis dried by β-globin 5'NTR from pCMV-Luc-IRES-SEAP, but not inhibit luciferase synthesis driven by β-globin 5'NTR from pCMV-Luc-IRES-SEAP and not inhibit SEAP synthesis driven by β-globin 5'NTR from pCMV-B-SEAP. This screen selects test compounds which specifically inhibit translation from IRES elements without affecting normal cellular translation (from β-globin 5'NTR) or inhibiting SEAP activity.

IRES elements targeted include those from rhinovirus, coxsackievirus, poliovirus, echovirus, hepatitis A virus, hepatitis B virus, hepatitis C virus, mengo virus, encephalomycarditis virus, foot-and-mouth disease virus, theiler's murine encephalomyelitis virus, infectious bronchitis virus, vesicular stomatitis virus, and sendai virus.

B. Transfecting Cells with Dicistronic Plasmid

To denature DNA, mix DNA with 15 µl 20× HBSS (5.0 g Hepes, 8.0 g NaCl, 0.36 g KCl, 0.125 g $Na_2HPO_4$—$H_2O$, 1.0 g dextrose, $H_2O$ to 50 ml), and bring up to 300 µl with $H_2O$, add 300 µl 1 mg/ml DAE dextran and incubate 4° C. for 30 minutes. Grow COS1 cells on 6 cm plate to 50–70% confluent (100% confluent=complete), wash cells with 2 ml MEM media (+pen-strep, −serum) added to side of plate, tilt plate to cover cells, aspirate off medium by tipping plate and aspirating from side of plate. Repeat wash two more times. Transfect cells by adding 600 µl denatured DNA to cells at 25° C. for 30 minutes with gentle rocking. Aspirate off dextran from cells, add 2 ml MEM (+2% fetal calf serum at 37° C.) and incubate 37° C. To assay translation, prepare cell extract using Triton X-100 or freeze/thaw method and assay for SEAP and luciferase activity as described above.

EXAMPLE 25

Animal Model(s) of Picornavirus Infection

Described below are appropriate animal models which may be used to test potential drugs further. A model in which the infection is "exposed" such as a dermal, buccal, ocular or vaginal model is preferred.

A. Infection in Experimental Animals

A major characteristic of rhinoviruses is a high degree of species specificity. Chimpanzees have been infected with types 14 and 43 and gibbons with types 1A, 2, and 14; no overt illnesses were observed in the infected animals (Dick, 1968 Proc. Soc. Exp. Biol. Med. 127, 1079–1081; Pinto and Haff, 1969, Nature 224, 1310–1311). Inoculation of vervent and rhesus monkeys with M (monkey kidney grown) strains of virus did not produce infection. Infection was not produced in rabbits, guinea pigs, weanling mice, or 1-day-old mice injected with human rhinoviruses by the subcutaneous, intraperitoneal, or intravenous route. Similarly, intracranial injections of monkeys, hamsters, or baby mice did not induce either infection or disease (Hamparian et al., 1961, Proc Soc. Exp. Biol. Med. 108, 444–453; Jackson and Muldoon, 1973, J. Infect. Dis. 127, 328–355; Kisch et al., 1964, Am. J. Hyg. 79, 125–133). Intranasal inoculation of ferrets, hamsters, and newborn mice was also without effect. One of the animal rhinoviruses, equine rhinovirus, can infect other species including humans (Plummer, 1963, Arch. Ges. Virusforshchr 12 694–700.); a hamster model for use in screening of antiviral compounds has been developed that utilizes this virus. One of the human rhinoviruses, type 2, was recently adapted to grow in L cells (195); this virus was then used in a mouse model of rhinovirus infection where in vitro growth was demonstrated (196).

The cardioviruses (Columbia SK virus, EMC virus, ME virus, MM virus, and mengovirus) all belong to a single serotype and are here all considered to be strains of EMC virus. They are generally regarded as murine viruses although their host range includes humans, pigs, elephants, and squirrels among others.

The Theiler's murine encephalomyelitis viruses (TMEV), also representing a single serotype, are divided into two groups, typified by strains called GDVII and TO. the GDVII group causes an acute polio-like disease in mice. The TO group are less virulent and cause a chronic demyelinating disease resembling multiple sclerosis and have thus become important models for study of this and other motor neuron diseases (Lipton and Rozhan, 1986, Bhatt, ed., Viral and Mycoplasma Infection of Laboratory Rodents, pp. 253–276, Academic Press, Orlando.217).

Apthoviruses (foot-and-mouth disease viruses) infect cloven-footed animals, especially cattle, goats, pigs, sheep, and, rarely, even humans.

Some picornaviruses, such as cricket paralysis virus (Tinsley et al., 1984, Intervirology 21, 181–186.) infect insects (Longworth, 1978, Adv. Virus Res. 23, 103–157.; Moore and Tinsley, 1982, Arch. Virol. 72, 229–245.; Scotti et al., 1981, Adv. Virus Res. 26, 117–142.).

B. Experimental Infection, Host Range

The host range of the enteroviruses varies greatly from one type to the next and even among strains of the same type. They may readily be induced, by laboratory manipulation, to yield variants that have host ranges and tissue tropisms different from those of wild strains; this has led to the development of attenuated poliovaccine strains.

Polioviruses have a very restricted host range among laboratory animals (Bodian, 1959, In: Rivers and Horsfall, eds., Viral and Rickettsial Infections of Man, Third ed., pp. 430–473, 479–518, Lippincott, Philadelphia). Most strains will infect and cause flaccid paralysis only in monkeys and chimpanzees. Infection is initiated most readily by direct inoculation into the brain or spinal cord. Chimpanzees and cynomolgus monkeys can also be infected by the oral route; in chimpanzees, the infection thus produced is usually asymptomatic. The animals become intestinal carriers of the virus; they also develop a viremia that is quenched by the appearance of antibodies in the circulating blood. Unusual strains have been transmitted to mice or chick embryos.

The original criteria for classification as a member of the echovirus group included the provision that the prototype strains fail to produce disease in suckling mice or in monkeys. However, different strains can produce variants that exhibit animal pathogenicity. A number of echoviruses have produced inapparent infections in monkeys, with mild lesions in the CNS (Wenner, 1962, Ann NY Acad. Sci. 101, 398–412.). In the chimpanzee, no apparent illness is produced, but infection can be demonstrated by the presence and persistence of virus in the throat and in the feces and by type-specific antibody responses (Itoh and Melnick, 1957, J. Exp. Med. 106, 677–688.). Initially, echoviruses were distinguished from coxsackieviruses by their failure to produce pathological changes in newborn mice; this led to the early classification of these strains as coxsackievirus A23. Conversely, strains of some coxsackievirus types (especially A9) lack mouse pathogenicity and thus resemble echoviruses. This variability in biological properties is the chief reason why new members of the genus are no longer being sub-classified as echoviruses or coxsackieviruses but are simply called enteroviruses.

The cardinal feature of coxsackieviruses is their infectivity for newborn mice (Daldorf and Melnick, 1965, In: Horsfall and Tamm, eds., Viral and Rickettsial Infections of Man, Fourth ed., pp. 474–512, Lippincott, Philadelphia). Chimpanzees and cynomolgus monkeys can be infected subclinically; virus appears in the blood and throat for short periods and is excreted in the feces for 2–5 weeks. Type A14 produces poliomyelitis-like lesions in adult mice and in monkeys, but in suckling mice this type produces only myositis. Type A7 strains produce paralysis and severe CNS lesions in monkeys (Dalldorf, 1957, J. Exp. Med. 106, 69–76, 268), and at one time this serotype was considered to be a fourth type of poliovirus.

Group A coxsackieviruses characteristically produce widespread myositis in the skeletal muscles of newborn mice, resulting in flaccid paralysis without other observable lesions (Daldorf and Melnick, 1965, In: Horsfall and Tamm, eds., Viral and Rickettsial Infections of Man, Fourth ed., pp. 474–512, Lippincott, Philadelphia). In addition to being able to infect the immature skeletal muscles of newborn mice, coxsackieviruses of the A group also can infect surgically denervated muscles of adult mice, whereas mature innervated muscles are relatively resistant. Leg muscles of adult mice in which quantal release of acetylcholine had been blocked with botulinum toxin were susceptible when subsequently injected with coxsackievirus A2 (Andrew et al., 1984, Science 223, 714–716.). Since the only known action of the toxin is the effect on acetylcholine release, the findings suggest that synaptic transmission has a role in preventing the susceptibility of skeletal muscles to coxsackievirus infection.

Group B viruses can produce a myositis that is more focal in distribution than that produced by viruses of group A, but they also give rise to a necrotizing steatitis involving principally the natural fetal fat lobules (e.g., intrascapular pads, cervical and cephalic pads). Encephalitis is found at times; the animals die with paralysis of the spastic type. Some B strains also produce pancreatitis, myocarditis, endocarditis, and hepatitis in both suckling and adult mice. The corticosteroids may enhance the susceptibility of older mice to infection of the pancreas. Normal adult mice tolerate infections with group B coxsackieviruses, but in mice subjected to sustained postweaning undernutrition (marasmus), coxsackievirus B3 produces severe disease, including persistence of infective virus in the heart, spleen, liver, and pancreas. Lymphoid tissues are markedly atrophic in marasmic animals. Transfer of lymphoid cells from normal mice immunized against the virus provides virus-infected marasmic mice with significant protection against severe sequelae (Woodruff and Woodruff, 1971, Proc. Natl. Acad. Sci. USA 68, 2108–2111). These observations support the hypothesis that lymphocyte-mediated defense mechanisms may play an important role in normal recovery from primary viral infections (Paque, 1981, Infect. Immun. 31, 470–479.; Woodruff, 1980, Am J. Pathol. 101, 427–478.205,283). Athymic mice exposed to coxsackievirus B3 develop a persistent infection in which the myocardium is affected in a disseminated, multifocal way. The RNA viral genome can readily be detected in the myocardium by the use of radioactively labeled cloned coxsackie B3 cDNA (Kanbdolf et al., 1987, Proc. Natl. Acad. Sci. USA 84, 6272–6276).

C. Experimental Infection in Animals and Host Range

Attempts to transmit HAV to experimental were generally unsuccessful until the 1960s. An outbreak of infectious hepatitis among chimpanzee handlers at a United States Air Force base during 1958–1960 (Hills, 1961, Am. J. Hyg. 73, 316–328.; Hills, 1963, Transfusion 3, 445–453.) restimulated interest in subhuman primates as possible models for human hepatitis. In 1962, Deinhardt et al. (Dienhardt et al., 1962, Am. J. Hyg. 75, 311–321.) described the development of mild liver enzyme abnormalities and histopathologic changes in about two-thirds of 37 chimpanzees inoculated with acute-phase serum or feces. Expectations of jaundice (which rarely occurs in subhuman primates), as well as the assay of aspartate aminotransferase instead of the more sensitive and specific aminotransferase, served to minimize the significance of these results.

In 1967, Deinhardt, et al. (J. Exp. Med. 125, 673–688.) successfully transmitted and passaged hepatitis in marmosets by using acute-phase sera from patients with disease that had the epidemiologic characteristics of hepatitis A. Interpretation of the results was initially hampered by the presence of a latent marmoset agent (or an agent of non-A, non-B hepatitis) in some Saguinus species that was reactivated by experimental manipulations, resulting in hepatitis (Parks and Melnick, 1969, J. Infect. Dis. 120, 539–547, 548–559.). Their results were subsequently confirmed when coded control sera and acute-phase sera from HAV-infected human volunteers were correctly identified upon inoculation into marmosets (Holmes et al., 1971, J. Infect. Dis. 124, 520–521.; Holmes et al., 1969, Science 165, 816–817.). Further evidence for transmission to marmosets and eventually to chimpanzees soon followed (Dienstag et al., 1975, J. Infect. Dis. 132, 532–545.; Lorenz et al., Proc. Soc. Exp. Biol. Med. 135, 348–354.; Lundquist et al., 1974, Proc. Natl. Acad. Sci. USA 71, 4774–4777.; Maynard et al., 1975, J. Infect. Dis. 131, 194–196.; Maynard et al., 1975, Am. J. Med. Sci. 270, 81–85.; Provost et al., 1977, Proc. Soc. Exp. Biol. Med. 155, 283–286.).

HAV produces disease in humans, chimpanzees (*Pan troglodytes*) (Dienstag et al., 1975, J. Infect. Dis. 132, 532–545.; Lundquist et al., 1974, Proc. Natl. Acad. Sci. USA 71, 4774–4777.; Maynard et al., 1975, J. Infect. Dis. 131, 194–196.; Maynard et al., 1975, Am. J. Med. Sci. 270, 81–85.), owl monkeys (*Aotus trivirgatus*) (LeDuc et al., 1983, Infect. Immun. 40, 766–772.; Lemon, 1982, J. Med. Virol. 10, 25–36.), stump-tailed monkeys (*Macaca speciosa*) (Mao et al., 1981, J. Infect. Dis. 144, 55–60.), and several species of South American marmoset (tamarin) monkeys (most notably *Saquinus mystax* and *S. labiatus*) (Deinhardt et al., 1967, J. Exp. Med. 125, 673–688.; Holmes et al., 1971, J. Infect. Dis. 124, 520–521.; Holmes et al., 1969, Science 165, 816–817; Lorenz et al., Proc. Soc. Exp. Biol. Med. 135, 348–354.; Mascoli et al., 1973, Proc. Soc. Exp. Biol. Med. 142, 276–282.; Provost et al., 1977, Proc. Soc. Exp. Biol. Med. 155, 283–286.; Purcell et al., 1975, Am. J. Med. Sci. 270, 61–71.). Disease in nonhuman primates resembles that in humans but is usually milder. After infecting these animals, HAV or viral antigen can usually be detected in serum, liver, bile, and feces.

Other primate species are susceptible to infection but do not develop disease; this limits their usefulness for laboratory studies of human HAV strains (Burke et al., 1981, Lancet, 2, 928.; Burke et al., 1984, AM J. Trop. Med. Hyg. 33, 940–944,; Eichberg et al., 1980, Lab Anim. Sci. 30, 541–543.). Cynomolgus monkeys (*Macaca fascicularis*) were found to have been infected with HAV in the wild (Burke and Heisey, 1984, Am. J. Trop. Med. Hyg. 33, 940–944.). In the laboratory, hepatitis was induced in *M. fascicularis* and *M. arctoides* by experimental inoculation with the YaM-55 strain of HAV isolated from cynomolgus monkeys but not by human HAV strain HAS15 (Andzhaparidze et al., 1987, Vopr Virus 2, 440–448.). These data, along with the demonstration of genomic differences between the PA21 strain of the HAV isolated from owl monkeys and the human HAV strain HM175, suggest that host range variants of HAV may have been selected in subhuman primates (Lemon et al., 1987, J. Virol. 61, 735–742.). In addition, it appears that a host range alteration can be experimentally induced. After 20 passages in marmosets, HAV strain MS-1 was more virulent for marmosets but was attenuated for chimpanzees (Bradley et al., 1984, J. Med. Virol. 14, 373–386.).

Administration of Agents

In practicing the methods of the invention, the compositions can be used alone or in combination with one another, or in combination with other therapeutic or diagnostic agents. These compositions can be utilized in vivo, ordinarily in a mammal, preferably in a human, or in vitro. In employing them in vivo, the compositions can be administered to the mammal in a variety of ways, including parenterally, intravenously, subcutaneously, intramuscularly, colonically, rectally, vaginally, nasally, orally, transdermally, topically, ocularly, intraperitoneally, or as suitably formulated surgical implants employing a variety of dosage forms. As will be readily apparent to one skilled in the art, the useful in vivo dosage to be administered and the particular mode of administration will vary depending upon the mammalian species treated, the particular composition employed, and the specific use for which these compositions are employed. The determination of effective dosage levels, that is the dosage levels necessary to achieve the desired result, will be within the ambit of one skilled in the art. Typically, applications of compositions are commenced at lower dosage levels, with dosage level being increased until the desired effect is achieved.

The dosage for the compositions of the present invention can range broadly depending upon the desired affects and the therapeutic indication. Typically, dosages will be between about 0.01 μg and 100 mg/kg, preferably between about 0.01 and 10 mg/kg, body weight. Administration is preferably per os on a daily or as-needed basis.

Orally-administered formulations can be prepared in conventional forms, including capsules, chewable tablets, enteric-coated tablets, syrups, emulsions, suspensions, or as solid forms suitable for solution or suspension in liquid prior to administration. Suitable excipients are, for example, water, saline, dextrose, mannitol, lactose, lecithin, albumin, sodium glutamate, cysteine hydrochloride or the like. In addition, if desired, the pharmaceutical compositions may contain minor amounts of nontoxic auxiliary substances, such as wetting agents, pH buffering agents, and the like. If desired, absorption enhancing preparations (e.g., liposomes) may be utilized.

In selected cases, drug delivery vehicles may be employed for systemic or topical administration. They can be designed to serve as a slow release reservoir, or to deliver their contents directly to the target cell. An advantage of using direct delivery drug vehicles is that multiple molecules are delivered per vehicle uptake event. Such vehicles have been shown to also increase the circulation half-life of drugs which would otherwise be rapidly cleared from the blood stream. Some examples of such specialized drug delivery vehicles which fall into this category are liposomes, hydrogels, cyclodextrins, biodegradable polymers (surgical implants or nanocapsules), and bioadhesive microspheres.

For example, a liposome delivery vehicle originally designed as a research tool, Lipofectin, has been shown to deliver intact molecules to cells. Liposomes offer several advantages: They are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

Other controlled release drug delivery systems, such as nanoparticles and hydrogels may be potential delivery vehicles for an agent. These carriers have been developed for chemotherapeutic agents.

Topical administration of agents is advantageous since it allows localized concentration at the site of administration with minimal systemic adsorption. This simplifies the delivery strategy of the agent to the disease site and reduces the extent of toxicological characterization. Furthermore, the amount of material to be administered is far less than that required for other administration routes.

Effective delivery requires the agent to diffuse into the infected cells. Chemical modification of the agent may be all that is required for penetration. However, in the event that such modification is insufficient, the modified agent can be co-formulated with permeability enhancers, such as Azone or oleic acid, in a liposome. The liposomes can either represent a slow release presentation vehicle in which the modified agent and permeability enhancer transfer from the liposome into the infected cell, or the liposome phospholipids can participate directly with the modified agent and permeability enhancer in facilitating cellular delivery.

Agents may also be systemically administered. Systemic absorption refers to the accumulation of drugs in the blood stream followed by distribution throughout the entire body. Administration routes which lead to systemic absorption include: oral, intravenous, subcutaneous, intraperitoneal, intranasal, intrathecal and ocular. Each of these administration routes exposes the agent to an accessible diseased tissue. Subcutaneous administration drains into a localized lymph node which proceeds through the lymphatic network into the circulation. The rate of entry into the circulation has been shown to be a function of molecular weight or size. The use of a liposome or other drug carrier can localize the agent at the lymph node and participate in the delivery of the agent to the cell.

A formulation which can associate agents with the surface of lymphocytes and macrophages is also useful. This will provide enhanced delivery to, for example, HSV-infected cells by taking advantage of the specificity of macrophage and lymphocyte immune recognition of infected cells.

Intraperitoneal administration also leads to entry into the circulation with the molecular weight or size of the agent-delivery vehicle complex controlling the rate of entry.

Liposomes injected intravenously show accumulation in the liver, lung and spleen. The composition and size can be adjusted so that this accumulation represents 30% to 40% of the injected dose. The rest is left to circulate in the blood stream for up to 24 hours.

All publications referenced herein are hereby incorporated by reference herein, including the nucleic acid sequences listed in each publication.

Other embodiments are within the following claims.

We claim:

1. A method of assaying for a potential antiviral agent, comprising:
   a) providing a solid support comprising a bound viral internal ribosome entry site (IRES);
   b) contacting said solid support with a library of agents to be tested, each agent comprising a label;
   c) incubating said library and said IRIES under conditions effective to allow binding of an agent of said library to said IRIS;
   d) washing said solid support; and
   e) measuring the solid support for the presence of said label.

2. A method according to claim 1 further comprising isolating said agent that binds said IRES.

3. A method of assaying for a potential antiviral agent, comprising:
   a) providing a solid support comprising a bound viral internal ribosome entry site (IRES);
   b) contacting said solid support with a library of cellular components to be tested, each comprising a label;
   c) incubating the library of cellular components and the IRES under conditions effective to allow binding;
   d) washing said solid support; and
   e) measuring the solid support for the presence of said label.

4. A method according to claim 3 further comprising isolating a cellular component of said library bound to said IRES.

5. A method according to claim 3 wherein said library of cellular components comprises a cell extract.

6. A method of assaying for a potential antiviral agent comprising:
   a) providing a solid support comprising a bound viral internal ribosome entry site (IRES);
   b) contacting said solid support with at least one cellular component and a test agent, wherein said cellular component comprises a label;
   c) incubating said cellular component, said test agent and said IRES under conditions effective to allow binding of said cellular component and said IRES;
   d) washing said solid support; and
   e) measuring the solid support for the presence of said label, whereby a decrease of said label in the presence of said test agent as compared to a control indicates that said test agent is a potential antiviral agent.

7. A method according to claim 6 further comprising isolating said potential antiviral agent.

8. A method according to claim 1, 3, or 6 wherein said IRES is from an enterovirus.

9. A method according to claim 1, 3, or 6 wherein said IRES is from a rhinovirus.

10. A method according to claim 1, 3, or 6 wherein said IRES is from a cardiovirus.

11. A method according to claim 1, 3, or 6 wherein said IRES is from an aphthovirus.

12. A method according to claim 1, 3, or 6 wherein said IRES is from a picornavirus.

13. A method according to claim 1, 3, or 6 wherein said IRES is a hepatitis A IRES.

14. A method according to claim 1, 3, or 6 wherein said IRES is a hepatitis B IRES.

15. A method according to claim 1, 3, or 6 wherein said IRES is a hepatitis C IRES.

16. A method according to claim 1, 3, or 6 wherein said label is radioactive.

17. A method according to claim 1, 3, or 6 wherein said label is biotin.

18. A method according to claim 1, 3, or 6 wherein said measuring is by fluorography.

19. A method according to claim 5 wherein said cell extract is unpurified.

* * * * *